(12) United States Patent
Drouillard et al.

(10) Patent No.: US 12,359,162 B2
(45) Date of Patent: Jul. 15, 2025

(54) MICROBIAL CELLS, METHODS OF PRODUCING THE SAME, AND USES THEREOF

(71) Applicants: KANSAS STATE UNIVERSITY RESEARCH FOUNDATION, Manhattan, KS (US); AXIOTA U.S., INC., Fort Collins, CO (US)

(72) Inventors: James Scott Drouillard, Manhattan, KS (US); Celine Caroline Aperce, Wamego, KS (US); Gina Rae Herren, Wamego, KS (US); Tara Jo Ellerman, Manhattan, KS (US); Ciana Marie Scaletti, Manhattan, KS (US); Katherine Van Jordan, Manhattan, KS (US); James Morris Lattimer, Manhattan, KS (US); Scott Beyer, Manhattan, KS (US); Solange Uwituze, Kampala (UG); Teresa Lea Douthit, Manhattan, KS (US); Christina Denise Gunkel, Broken Bow, NE (US)

(73) Assignees: Kansas State University Research Foundation, Manhattan, KS (US); Axiota U.S., Inc., Fort Collins, CO (US)

( * ) Notice: Subject to any disclaimer, the term of this patent is extended or adjusted under 35 U.S.C. 154(b) by 0 days.

(21) Appl. No.: 18/352,788

(22) Filed: Jul. 14, 2023

(65) Prior Publication Data

US 2023/0357706 A1 Nov. 9, 2023

Related U.S. Application Data

(60) Division of application No. 18/045,280, filed on Oct. 10, 2022, which is a continuation of application No. 16/481,962, filed as application No. PCT/US2018/016321 on Jan. 31, 2018, now Pat. No. 11,492,587.

(60) Provisional application No. 62/510,723, filed on May 24, 2017, provisional application No. 62/452,804, filed on Jan. 31, 2017, provisional application No. 62/452,816, filed on Jan. 31, 2017.

(51) Int. Cl.
| | | |
|---|---|---|
| A23K 50/20 | (2016.01) | |
| A23K 10/18 | (2016.01) | |
| A23K 20/00 | (2016.01) | |
| A23K 50/10 | (2016.01) | |
| A23K 50/30 | (2016.01) | |
| A23K 50/75 | (2016.01) | |
| A61K 35/744 | (2015.01) | |
| A61P 31/04 | (2006.01) | |
| C12N 1/04 | (2006.01) | |
| C12N 1/20 | (2006.01) | |

(52) U.S. Cl.
CPC ............... *C12N 1/20* (2013.01); *A23K 10/18* (2016.05); *A23K 50/10* (2016.05); *A23K 50/20* (2016.05); *A23K 50/75* (2016.05); *A61K 35/744* (2013.01); *A61P 31/04* (2018.01); *C12N 1/04* (2013.01)

(58) Field of Classification Search
CPC . C12N 1/20; C12N 1/04; A23K 10/18; A23K 50/10; A23K 50/20; A23K 50/75; A23K 50/30; A23K 20/00; A61K 35/744
See application file for complete search history.

(56) References Cited

U.S. PATENT DOCUMENTS

| | | |
|---|---|---|
| 3,713,836 A | 1/1973 | Carlsson |
| 3,956,482 A | 5/1976 | Hahn et al. |
| 4,138,498 A | 2/1979 | Das |
| 4,689,226 A | 8/1987 | Nurmi et al. |
| 5,308,615 A | 5/1994 | Deloach et al. |
| 5,380,525 A | 1/1995 | Leedle et al. |
| 5,529,793 A | 6/1996 | Garner et al. |
| 5,534,271 A | 7/1996 | Ware et al. |
| 5,939,303 A | 8/1999 | Cheng et al. |
| 5,985,605 A | 11/1999 | Cheng et al. |
| 6,960,341 B2 | 11/2005 | Viscomi et al. |
| 7,485,290 B2 | 2/2009 | Ushida et al. |
| 7,550,139 B2 | 6/2009 | Horn et al. |
| 8,114,396 B2 | 2/2012 | Horn et al. |
| 8,834,853 B2 | 9/2014 | Mazeaud et al. |
| 9,179,693 B2 | 11/2015 | Romero et al. |
| 9,351,516 B2 | 5/2016 | Nissen et al. |
| 9,476,084 B2 | 10/2016 | Brudnak et al. |

(Continued)

FOREIGN PATENT DOCUMENTS

| | | |
|---|---|---|
| AU | 2165688 A | 3/1989 |
| AU | 2018344097 B1 | 4/2020 |

(Continued)

OTHER PUBLICATIONS

Jacques S. Horsepower: Veter inary medicine student advances to global scholarship competition for her work on laminitis in horses. https://www.k-state.edu/media/newsreleases/apr12/alltechaward42412.html. 2012;1.*

(Continued)

*Primary Examiner* — Lynn Y Fan
(74) *Attorney, Agent, or Firm* — Sterne, Kessler, Goldstein & Fox P.L.L.C

(57) ABSTRACT

The present invention relates to microbial cells, including but not limited to aerobic bacteria cells and anaerobic bacteria cells, as well as yeast cells, and methods for producing the cells, feed additives and compositions comprising the cells, and uses involving administration of the cells to animals.

8 Claims, 28 Drawing Sheets

(56) References Cited

U.S. PATENT DOCUMENTS

| | | |
|---|---|---|
| 9,493,737 B2 | 11/2016 | Georgieva et al. |
| 9,546,352 B2 | 1/2017 | Mazeaud et al. |
| 9,554,583 B2 | 1/2017 | Hollard et al. |
| 9,554,590 B2 | 1/2017 | Quintens et al. |
| 10,093,894 B2 | 10/2018 | Yde et al. |
| 10,329,526 B2 | 6/2019 | Salmons et al. |
| 10,370,636 B2 | 8/2019 | Van Hee |
| 10,576,113 B2 | 3/2020 | Madhavamenon et al. |
| 10,834,942 B2 | 11/2020 | Davis et al. |
| 10,856,560 B2 | 12/2020 | Simpson et al. |
| 10,864,457 B2 | 12/2020 | Madsen et al. |
| 10,954,486 B2 | 3/2021 | Georgieva et al. |
| 11,492,587 B2 | 11/2022 | Drouillard et al. |
| 2004/0120963 A1 | 6/2004 | Ushida et al. |
| 2006/0067923 A1 | 3/2006 | Ushida et al. |
| 2006/0188550 A1 | 8/2006 | Winn |
| 2006/0257372 A1 | 11/2006 | Horn et al. |
| 2008/0138462 A1 | 6/2008 | Chan et al. |
| 2009/0028992 A1 | 1/2009 | Chan et al. |
| 2009/0246177 A1 | 10/2009 | Horn et al. |
| 2010/0136637 A1 | 6/2010 | Park et al. |
| 2013/0022575 A1 | 1/2013 | Cassity |
| 2013/0330307 A1 | 12/2013 | Millan |
| 2013/0330308 A1 | 12/2013 | Millan et al. |
| 2013/0330439 A1 | 12/2013 | Owens et al. |
| 2014/0037582 A1 | 2/2014 | Romero et al. |
| 2014/0065617 A1 | 3/2014 | Getman |
| 2014/0112897 A1 | 4/2014 | Pyne et al. |
| 2014/0234279 A1 | 8/2014 | Millan |
| 2014/0370572 A1 | 12/2014 | Van Lengerich et al. |
| 2015/0140171 A1 | 5/2015 | Nissen et al. |
| 2015/0218507 A1 | 8/2015 | Georgieva et al. |
| 2015/0291994 A1 | 10/2015 | Brudnak et al. |
| 2016/0029666 A1 | 2/2016 | Carpenter et al. |
| 2016/0213755 A1 | 7/2016 | Romero et al. |
| 2017/0020935 A1 | 1/2017 | Garner et al. |
| 2017/0202242 A1 | 7/2017 | Blom et al. |
| 2017/0224745 A1 | 8/2017 | Dart |
| 2018/0228181 A1 | 8/2018 | Villamizar et al. |
| 2019/0358272 A1 | 11/2019 | Laldas et al. |
| 2019/0376023 A1 | 12/2019 | Hollard et al. |
| 2020/0123588 A1 | 4/2020 | Mizrahi |
| 2020/0155470 A1 | 5/2020 | Rieu et al. |
| 2020/0281225 A1 | 9/2020 | Kiarie et al. |
| 2020/0352860 A1 | 11/2020 | Natu et al. |
| 2023/0128983 A1 | 4/2023 | Drouillard et al. |
| 2023/0357706 A1 | 11/2023 | Drouillard et al. |
| 2024/0018465 A1 | 1/2024 | Drouillard et al. |

FOREIGN PATENT DOCUMENTS

| | | |
|---|---|---|
| CN | 1480528 A | 3/2004 |
| CN | 1681522 A | 10/2005 |
| CN | 103533843 A | 1/2014 |
| CN | 103958664 A | 7/2014 |
| CO | 20190005965 A1 | 6/2019 |
| DE | 4024937 C1 | 4/1992 |
| EP | 0071858 A1 | 2/1983 |
| EP | 2675285 B1 | 11/2017 |
| EP | 2744888 B1 | 12/2017 |
| EP | 3287518 A1 | 2/2018 |
| EP | 3016511 B1 | 10/2019 |
| EP | 3702441 A1 | 9/2020 |
| EP | 2885395 B1 | 10/2020 |
| EP | 3007566 B1 | 12/2020 |
| IN | 235743 | 8/2009 |
| JP | H08502019 | 3/1996 |
| JP | 2013146273 A | 1/2013 |
| KR | 20130021764 | 3/2013 |
| MX | 9708793 A | 2/1998 |
| RU | 2119288 C1 | 9/1998 |
| RU | 02365621 C2 | 8/2009 |
| RU | 2650870 C1 | 4/2018 |
| WO | WO-1991013146 A1 | 9/1991 |
| WO | WO-1993013666 A1 | 7/1993 |
| WO | WO-1997048812 A2 | 12/1997 |
| WO | WO-2002080947 A1 | 10/2002 |
| WO | WO-2004009104 A1 | 1/2004 |
| WO | WO-2009024930 A2 | 2/2009 |
| WO | WO-2010047815 A2 | 4/2010 |
| WO | WO 2011018509 A1 | 2/2011 |
| WO | WO 2012098239 A1 | 7/2012 |
| WO | WO 2012110778 A2 | 8/2012 |
| WO | WO-2013024178 A1 | 2/2013 |
| WO | WO 2013083762 A1 | 6/2013 |
| WO | WO-2013186348 A1 | 12/2013 |
| WO | WO-2014020138 A2 | 2/2014 |
| WO | WO-2014029758 A1 | 2/2014 |
| WO | WO-2014029783 A1 | 2/2014 |
| WO | WO 2016011511 A1 | 1/2016 |
| WO | WO-2016019017 A1 | 2/2016 |
| WO | WO-2017015022 A1 | 1/2017 |
| WO | WO 2017025772 A1 | 2/2017 |
| WO | WO-2018144653 A1 | 8/2018 |
| WO | WO-2018154593 A1 | 8/2018 |
| WO | WO-2018179001 A1 | 10/2018 |
| WO | WO-2019079629 A1 | 4/2019 |
| WO | WO 2019079764 A1 | 4/2019 |
| WO | WO-2019118984 A2 | 6/2019 |
| WO | WO-2019215345 A1 | 11/2019 |
| WO | WO-2020176624 A1 | 9/2020 |
| WO | WO-2020176834 A1 | 9/2020 |
| WO | WO-2020212961 A1 | 10/2020 |
| WO | WO-2020243676 A1 | 12/2020 |
| WO | WO-2021055352 A1 | 3/2021 |
| WO | WO-2021151161 A1 | 8/2021 |

OTHER PUBLICATIONS

Dove et al. Foregut survivability of Megasphaera elsdenii in equine. Journal of Equine Veterinary Science. 2015;35:400-417.*

Haffner et al. Encapsulation of probiotics: insights into academic and industrial approaches. AIMS Materials Science. 2016;3(1):114-136.*

O'Brien A. Administering equine medication. https://www.horseillustrated.com/horse-health-administering-equine-medication. 2016; 1-6.*

Beard, W.L., et al., "Technical Note: A 2-Stage Cecal Cannulation Technique in Standing Horses," Journal of Animal Science, 89(8):2425-2429, American Society of Animal Science, United States (2011).

International Search Report and Written Opinion for International Application No. PCT/US2018/016321, Commissioner of Patents, Alexandria, Virginia, mailed on Jun. 6, 2018, 17 pages.

Teather, R.M., "Maintenance of Laboratory Strains of Obligately Anaerobic Rumen Bacteria," Applied and Environmental Microbiology, 44(2): 499-501, American Society for Microbiology, United States (1982).

Yanke, L.J., et al., "Phytase Activity of Anaerobic Ruminal Bacteria," Microbiology, 144 (Pt 6): 1565-1573, Minister of Public Works and Government Services Canada (1998).

International Search Report and Written Opinion for International Application No. PCT/US2018/056777, Commissioner of Patents, Alexandria, Virginia, mailed on Dec. 13, 2018, 14 pages.

Shrestha, U.T., My scientific Blog-Research and Articles, accessed at https://upendrafts.blogspot.com, 9 pages (2010).

Kailasapathy, K., et al., "Microencapsulation of Probiotic bacteria: Technology and Potential Applications," Curr. Issues Intest. Microbiol. 3:39-48, Horizon Scientific Press, United States (2002).

Leslie, S.B., et al., "Trehalose and Sucrose Protect Both Membranes and Proteins in Intact Bacteria during Drying," Applied Environmental Microbiology 61(10): 3592-3597, American Society for Microbiology, United States (1995).

Mitropoulou, G., et al., "Immobilization Technologies in Probiotic Food Production," Journal of Nutrition and Metabolism 716861:16 pages, Hindawi Publishing Corporation, India (2013).

Miyamoto-Shinohara, et al., "Survival of freeze-dried bacteria," J. Gen. Appl. Microbiol 54:9-24, J-SAGE, Japan (2008).

Jorquera, M., et al., "Current and future biotechnological applications of bacterial phytases and phytase-producing bacteria," *Microbes and Environments* 23(3):182-191, Japanese Society of Microbial Ecology, Japan (2008).

(56) References Cited

OTHER PUBLICATIONS

Weimer, P.J., et al., "Fermentation of alfalfa wet-fractionation liquids to volatile fatty acids by *Streptococcus bovis* and *Megasphaera elsdenii*," Bioresource Technology 142:88-94, Elsevier, Netherlands (2013).

Khan, T., et al., "Antioxidants Keep the Potentially Probiotic but Highly Oxygen-Sensitive Human Gut Bacterium *Faecalibacterium prausnitzii* Alive at Ambient Air," PLOS ONE:e96097, 7 pages, Public Library of Science, United States (2014).

United States Department of Agriculture, "SBIR Phase II: Innovations in Manufacturing Technology for a Probiotic Containing Megasphaera Elsdenii NCIMB 41125," retrieved from <https://reeis.usda.gov/web/crisprojectpages/1003461-sbir-phase-ii-innovations-in-manufacturing-technology-for-a-probiotic-containing-megasphaera-elsdenii-ncimb-41125.html>, 7 pages, retrieved on Jun. 9, 2021 (published after Jan. 2017).

Hagg, F., et al., "The effect of a Direct Fed Microbial (*Megasphaera elsdenii*) on the Productivity and Health of Holstein Cows," South African Journal of Animal Science 40(2): 101-112, South African Society for Animal Science, South Africa (2012).

Leeuw, K-J., et al., "Effect of *Megasphaera elsdenii* NCIMB 41125 drenching on health and performance of steers fed high and low roughage diets in the feedlot," South African Journal of Animal Science 39(4):337-348, South African Society for Animal Science, South Africa (2009).

Meissner, H.H., et al., "Ruminal acidosis: A review with detailed reference to the controlling agent *Megasphaera elsdenii* NCIMB 41125," South African Journal of Animal Science 40(2):79-100, South African Society for Animal Science, South Africa (2010).

Rossi, F., et al., "Effect of a *Saccharomyces cerevisiae* culture on growth and lactate utilization by the ruminal bacterium *Megaspahera elsdenii*" Ann Zootech 44:403-409, Elsevier, Netherlands (1995).

Third Party Observations mailed Nov. 26, 2021, against EP3577213, in the name of Kansas State University Research Foundation and MS Biotech, Inc., European Patent Office, Germany, 25 pages.

Adams, G., et al., "Cryopreservation and freeze-drying protocols: the principles of freeze-drying," Extract from Methods in Molecular Biology 368:16, 1 page, Humana Press, Inc., United States (2007).

ATCC Product Sheet, "*Megasphaera elsdenii* (ATCC 25940)," 2 pages (2019).

Bergey, D., et al., "Extract from Bergey's Manual of Systematic Bacteriology vol. 3: The Firmicutes," Genus XIII. *Megasphaera*, 1086, Springer, United States (2009).

Chaucheyras, F., et al., "Effects of a strain of *Saccharomyces cerevisiae* (Levucell® $SC^1$), a microbial additive for ruminants, on lactate metabolism in vitro," Can. J. Microbiol. 42:927-933, NRC Research Press, Canada (1996).

Elsden, S.R., et al., "The Production of Fatty Acids By a Gram-negative Coccus," Biochem J. 55(1): 183-189, Portland Press, United States (1953).

Elsden, S.R., et al., "Properties of a Fatty Acid Forming Organism Isolated From The Rumen of Sheep," J. Bacteriol. 72(5): 681-689, American Society for Microbiology, United States (1956).

Gutierrez, J., et al., "Bacterial Changes in the Rumen During the Onset of Feed-lot Bloat of Cattle and Characteristics of *Peptostreptococcus elsdenii* n. sp.," Appl Microbiol 7(1):16-22, American Society for Microbiology, United States (1959).

Langa, R.L.S., "Optimisation of cell growth and shelf life stability of *Megasphaera elsdenii* NCIMB 41125," University of Pretoria: 1-144, South Africa (2010).

Marounek, M., et al., "Metabolism and Some Characteristics of Ruminal Strains of *Megasphaera elsdenii*," Applied and Environmental Microbiology 55(6):1570-1573, American Society for Microbiology, United States (1989).

Material Safety Data Sheet, "Dehydrated Culture Media: reinforced Clostridial Medium (RCM)," Thermofisher Scientific, 2 pages, United States (2001).

National Collection of Industrial Food and Marine Bacteria, "NCIMB 702261," retrieved from <https://store.ncimb.com/page/strains%20record%20name%20display/23138>, retrieved on Oct. 13, 2020, 1 page.

National Collection of Industrial Food and Marine Bacteria, "NCIMB 702262," retrieved from <https://store.ncimb.com/page/strains%20record%20name%20display/23139>, retrieved on Oct. 13, 2020, 1 page.

National Collection of Industrial Food and Marine Bacteria, "NCIMB 702410," retrieved from <https://store.ncimb.com/page/strains%20record%20name%20display/23143>, retrieved on Oct. 13, 2020, 1 page.

Rossi, F., et al., "Effects of peptidic fractions from *Saccharomyces cerevisiae* culture on growth and metabolism of the ruminal bacteria *Megasphaera elsdenii*," Anim. Res 53:177-186, INRA/EDP Sciences, United States (2004).

Soto-Cruz, O., et al., "Stimulation of the *Megasphaera elsdenii*'s Butyrate Production in Continuous Culture by a Yeast Additive," Brazilian Archives of Biology and Technology 44(2):179-184, Instituto de Tecnologia do Paraná, Brazil (2001).

Suihiko, M.-L., et al., "Maintenance of the anaerobic beer spoilage bacteria *Pectinatus* and *Megaspahaera*," Food Microbiology 7:33-41, Academic Press, United States (1990).

Wikipedia, "Freeze-drying," retrieved from <https://en.wikipedia.org/w/index.php?title=freeze-drying&oldid=1057299009">, retrieved on Nov. 26, 2021, 13 pages (2021).

Newbold, C.J., et al., "Different strains of *Saccharomyces cerevisiae* differ in their effects on ruminal bacterial numbers in vitro and in sheep," J Anim Sci 73(6):1811-1818, American Society of Animal Science, United States (Jun. 1995).

Office Action mailed Mar. 21, 2022, in U.S. Appl. No. 16/481,962, Drouillard, J., et al., § 371(c) date: Jul. 30, 2019, 10 pages.

Office Action mailed Oct. 22, 2021, in U.S. Appl. No. 16/481,962, Drouillard, J., et al., § 371(c) date: Jul. 30, 2019, 8 pages.

Lalsiamthara, J., "Log phase vs stationary phase for storage?" ResearchGate.net, accessed at https://www.researchgate.net/post/Log_phase_vs_stationary_phase_for_storage, accessed on Apr. 5, 2024, 8 pages.

Office Action mailed Oct. 31, 2023, in U.S. Appl. No. 18/352,801, Drouillard, J., et al., filed Jul. 14, 2023, 12 pages.

Office Action mailed Feb. 8, 2024, in U.S. Appl. No. 18/352,801, Drouillard, J., et al., filed Jul. 14, 2023, 8 pages.

Dianawati, D., et al., "Stability of microencapsulated *Lactobacillus acidophilus* and *Lactococcus lactis* ssp. *cremoris* during storage at room temperature at low $a_w$," Food Research International 50(1):259-265, Elsevier, Netherlands (Jan. 2013).

Santivarangkna, C., et al., "Alternative drying processes for the industrial preservation of lactic acid starter cultures," Biotechnol Prog 23(2):302-315, Wiley, United States (Mar. 2007).

Miller, K.A., "Utilizing Lactipro (*Megasphaera elsdenii* NCIMB 41125) to Accelerate Adaptation of Cattle to High-Concentrate Diets and Improve the Health of High-Risk Calves," Ph.D Dissertation, Kansas State University, published online May 1, 2013, accessed at https://krex.k-state.edu/items/efa3fa97-48d6-4e67-8b22-ae6328787c3e, accessed on Jun. 12, 2024, 133 pages.

MS Biotec, Press Release on Apr. 1, 2015, "MS Biotec announces release of Lactipro Advance," accessed at https://www.feedstuffs.com/agribusiness-news/ms-biotec-announces-release-of-lactipro-advance, accessed on Jun. 12, 2024, 8 pages.

Receipt of Deposit *Megasphaera elsdenii* NCIMB 41125, Aberdeen, Scotland, 10 pages.

Office Action mailed May 29, 2024, in U.S. Appl. No. 18/352,801, Drouillard, J., et al., filed Jul. 14, 2023, 11 pages.

\* cited by examiner

MICROBIAL CELLS, METHODS OF PRODUCING THE SAME, AND USES THEREOF

CROSS-REFERENCE TO RELATED APPLICATIONS

This application is a divisional of U.S. application Ser. No. 18/045,280, which is a continuation of U.S. application Ser. No. 16/481,962 (now U.S. Pat. No. 11,492,587; issued: Nov. 8, 2022), which is a 35 U.S.C. § 371 National Phase Application of International Application No. PCT/US2018/016321, filed Jan. 31, 2018, which claims the priority benefit of U.S. Provisional Application No. 62/510,723, filed May 24, 2017, U.S. Provisional Application No. 62/452,816, filed Jan. 31, 2017, and U.S. Provisional Application No. 62/452,804, filed Jan. 31, 2017, each of which is incorporated herein by reference in its entirety.

STATEMENT REGARDING FEDERALLY SPONSORED RESEARCH OR DEVELOPMENT

This invention was made with government support under Grant Number 2014-33610-22112 awarded by the National Institute of Food and Agriculture. The government has certain rights in the invention.

BACKGROUND OF THE DISCLOSURE

Field of Invention

The present invention relates to *Megasphaera elsdenii* cells, methods for producing *M. elsdenii* cells, feed additives and compositions comprising the cells, and uses involving administration of the cells to animals, including, e.g., for improved growth performance and/or health. The present invention also relates to microbial cells, including but not limited to aerobic bacteria, anaerobic bacteria, and yeast cells, and methods for producing microbial cells, feed additives and compositions comprising the microbial cells, and uses involving administration of the microbial cells to animals, including, e.g., for improved growth performance and/or health.

BACKGROUND

*Megasphaera elsdenii* (i.e., *M. elsdenii*) is a non-motile, Gram-negative diplococci that utilizes lactate as a preferred carbon source and can help to prevent acidosis, which is a common digestive disorder that affects millions of beef and dairy cattle each year.

When cattle and other ruminants ingest large quantities of starchy foods (e.g., cereal grains) or simple sugars, opportunistic microorganisms in the stomach can rapidly ferment these compounds into lactic acid. Lactic acid is a potent organic acid and can lead to lactic acidosis, which can disrupt normal digestive activity and cause extensive damage to the digestive tract lining in ruminants. Affected animals have suboptimal performance. And, the most acute form of lactic acidosis can cause irreversible damage to an animal's digestive and respiratory systems, as well as increased mortality rates.

*M. elsdenii* can help to control lactic acidosis by the bacterium's ability to convert lactic acid into volatile fatty acids (VFA; e.g. butyrate, propionate, and acetate), which are harmless organic compounds. But, *M. elsdenii* populations in the gastrointestinal tract of ruminants are often at levels too low to prevent the risk of acidosis. Accordingly, a liquid culture of live cells from a strain of *M. elsdenii*, Lactipro®, was developed to increase the rate of colonization of *M. elsdenii* in the gastrointestinal tract of ruminants. See, e.g., U.S. Pat. No. 7,550,139. However, there are practical constraints that have limited the use of products containing *M. elsdenii*, including the difficulty of maintaining *M. elsdenii* products under the anaerobic conditions required by the organism and the difficulty of transporting the *M. elsdenii* products from production facility to site of end-use within 14 days, after which time the viability of *M. elsdenii* in the product decreases significantly.

While U.S. Pat. No. 4,138,498 generally discusses the potential lyophilization of *M. elsdenii*, it does not provide any methods for producing freeze-dried *M. elsdenii* that could be used on a commercial scale to overcome existing commercial limitations. Moreover, at least one group recently reported that freeze-drying microorganisms, including anaerobes such as *M. elsdenii*, is not commercially practical. See, e.g., WO 2017/015022.

Therefore, there is a need for *Megasphaera* cells, such as *Megasphaera elsdenii* cells, including methods of producing the same, that overcome existing limitations. There is also a need for other microbial cells, such as *Bifidobacterium*, such as *B. breve*, *Lactobacillus*, such as *L. plantarum*, *Bifidobacterium*, such as *B. animalis* subsp. *lactis*, *Pediococcus*, such as *P. acidilactici*, *Lactobacillus*, such as *L. casei*, *Bacillus*, such as *B. subtilis*, *Saccharomyces*, such as *S. boulardii* and *S. cerevisiae*, including methods of producing the same, that overcome existing limitations.

BRIEF SUMMARY OF THE DISCLOSURE

The present disclosure is directed to a method of producing freeze-dried *Megasphaera elsdenii* cells, comprising: (a) preparing a culture under anaerobic conditions comprising *M. elsdenii* cells and a growth media comprising at least two carbon sources selected from the group consisting of: casein, lactate, dextrose, fructose, fructan, glucose, sucrose, lactose, maltose, acetate, glycerol, sorbitol, mannitol, saccharose, xylose, molasses, fucose, glucosamine, dextran, a fat, an oil, glycerol, sodium acetate, arabinose, soy protein, soluble protein, raffinose, amylose, starch, tryptone, yeast extract and combinations thereof, (b) harvesting the cells under anaerobic conditions, (c) freezing the cells, and (d) freeze-drying the cells, wherein about $1 \times 10^3$ to about $1 \times 10^{12}$ CFU/g of freeze-dried *M. elsdenii* cells are produced.

In certain embodiments, the at least two carbon sources consist of about 50-90% of a first carbon source and about 10-50% of a second carbon source, wherein the second carbon source is different from the first carbon source, and wherein 100% of the at least two carbon sources consists of the first carbon source and the second carbon source.

The present disclosure is directed to a method of producing freeze-dried *Megasphaera elsdenii* cells, comprising: (a) preparing a culture comprising *M. elsdenii* cells and a growth media, (b) harvesting the cells under anaerobic conditions within 12 hours after the culture has ended its exponential growth phase and before the culture has begun its stationary growth phase, (c) freezing the cells, and (d) freeze-drying the cells, wherein freeze-dried *M. elsdenii* cells are produced.

In certain embodiments, the harvesting comprises at least one technique selected from the group consisting of: centrifugation, filtration, dialysis, reverse osmosis, and combinations thereof. In certain embodiments, the filtration comprises tangential flow filtration.

In certain embodiments, the culture comprises a liquid, and wherein the harvesting comprises removing about 60% to about 100% of the liquid.

In certain embodiments, the freezing is at a temperature of about −80° C. to about −210° C.

The present disclosure is directed to a method of producing freeze-dried *Megasphaera elsdenii* cells, comprising: (a) preparing a culture comprising *M. elsdenii* cells and a growth media, (b) harvesting the cells, (c) freezing the cells at a temperature of about
−80° C. to about −210° C. within 5 hours of harvesting, and (d) freeze-drying the cells,
wherein freeze-dried *M. elsdenii* cells are produced.

In certain embodiments, the freezing comprises contacting a container comprising the *M. elsdenii* cells with liquid nitrogen.

In certain embodiments, the freezing comprises contacting the cells with liquid nitrogen.

In certain embodiments, the freezing is at a temperature of about −196° C. and produces frozen pellets comprising the cells, and wherein the diameter of the frozen pellets is about 0.001 to about 0.5 inches.

In certain embodiments, the pH of the *M. elsdenii* culture prior to harvesting is between about 4.5 to about 7.0.

In certain embodiments, about $1\times10^3$ to about $1\times10^{12}$ CFU/g of the freeze-dried *M. elsdenii* cells are viable after storage at a temperature of about 25° C. for at least 2 weeks.

In certain embodiments, about $1\times10^3$ to about $1\times10^{12}$ CFU/g of the freeze-dried *M. elsdenii* cells are viable after storage at about 4° C. for at least 1 month.

In certain embodiments, the culture further comprises at least one cryoprotectant.

In certain embodiments, the at least one cryoprotectant is selected from the group consisting of: fructose, glucose, sucrose, milk powder, infant formula, skim milk, trehalose, maltodextrin, betaine, and combinations thereof.

In certain embodiments, the at least one cryoprotectant is present in an amount of about 1% to about 20% (w/v) of the culture.

In certain embodiments, the freeze-dried *M. elsdenii* is produced on a commercial scale.

In certain embodiments, the volume of the culture is at least about 50 liters.

In certain embodiments, about $1\times10^3$ to $1\times10^{12}$ CFU/g of *M. elsdenii* cells are viable after freeze-drying.

In certain embodiments, the cells in the culture consist of *M. elsdenii* cells.

The present disclosure is directed to a solid feed additive comprising the freeze-dried *M. elsdenii* cells produced by any of the above methods.

In certain embodiments, the solid feed additive further comprises another microorganism.

In certain embodiments, the solid feed additive is selected from the group consisting of: a powder, a granulate, a particulate, a pellet, a cake, or combinations thereof.

In certain embodiments, the solid feed additive is a probiotic.

The present disclosure is directed to a composition comprising the freeze-dried *M. elsdenii* cells produced by any of the above methods or any of the above solid feed additives.

In certain embodiments, the composition is a capsule.

The present disclosure is directed to a kit comprising the freeze-dried *M. elsdenii* cells produced by any of the above methods, any of the above solid feed additives, or any of the above compositions.

The present disclosure is directed to a method of administering *M. elsdenii* cells to an animal, comprising administering to the animal the freeze-dried *M. elsdenii* cells produced by any of the above methods, any of the above solid feed additives, or any of the above compositions.

The present disclosure is directed to a method for treating or preventing a condition or disorder associated with lactic acid production in the gastrointestinal tract of an animal, comprising administering to the animal an effective amount of the freeze-dried *M. elsdenii* cells produced by any of the above methods, any of the above solid feed additives, or any of the above compositions.

In certain embodiments, the condition or disorder is acidosis.

In certain embodiments, the condition or disorder is ruminal acidosis.

In certain embodiments, the condition or disorder is respiratory disease.

In certain embodiments, the condition or disorder is laminitis.

In certain embodiments, the condition or disorder is an infection.

In certain embodiments, the infection is with *Salmonella* or *Campylobacter*.

The present disclosure is directed to a method for preventing or decreasing the growth of an opportunistic microorganism in the gastrointestinal tract of an animal, comprising administering to the animal an effective amount of the freeze-dried *M. elsdenii* cells produced by any of the above methods, any of the above solid feed additives, or any of the above compositions.

In certain embodiments, the opportunistic microorganism is pathogenic.

In certain embodiments, the opportunistic microorganism is *Salmonella* or *Campylobacter*.

The present disclosure is directed to a method of improving the bioavailability of plant-derived phosphorous in the diet of an animal, comprising administering to the animal an effective amount of the freeze-dried *M. elsdenii* cells produced by any of the above methods, any of the above solid feed additives, or any of the above compositions.

The present disclosure is directed to a method of improving growth performance in an animal, comprising administering to the animal an effective amount of the freeze-dried *M. elsdenii* cells produced by any of the above methods, any of the above solid feed additives, or any of the above compositions, wherein the improved growth performance in the animal is an improvement in: feed intake, average daily gain, feed conversion ratio, carcass gain, milk production in a milk-producing animal, egg production in poultry, bone mineralization, or combinations thereof.

In certain embodiments, the freeze-dried *M. elsdenii* cells, the solid feed additive, or the composition is administered prior to, concomitantly with, or after feeding the animal with a food.

In certain embodiments, the method further comprises mixing the freeze-dried *M. elsdenii* cells or the solid feed additive with a liquid prior to administration.

In certain embodiments, the liquid is administered orally or by spraying the animal with the liquid.

In certain embodiments, the administering comprises a single administration of the *M. elsdenii* cells, feed additive, or composition.

In certain embodiments, the administering comprises a daily administration of the *M. elsdenii* cells, feed additive, or composition.

In certain embodiments, the administering comprises more than one administration of the *M. elsdenii* cells, feed additive, or composition on a single day.

In certain embodiments, the animal is a ruminant.

In certain embodiments, the ruminant is selected from the group consisting of: cattle, sheep, goats, deer, buffalo, and reindeer.

In certain embodiments, the animal is a non-ruminant.

In certain embodiments, the non-ruminant is selected from the group consisting of: equine, poultry, and swine.

In certain embodiments, the animal is a poultry animal.

In certain embodiments, the poultry animal is selected from the group consisting of: a chicken, a goose, a duck, a quail, a turkey, or a pigeon.

In certain embodiments, the poultry animal is selected from the group consisting of: a broiler, a broiler breeder, and a layer.

In certain embodiments, the poultry animal is a chicken.

In certain embodiments, the animal is an equine.

In certain embodiments, the equine is a horse, a pony, a donkey, or a mule.

The present disclosure is directed to a method for treating or preventing a condition or disorder associated with lactic acid production in the gastrointestinal tract of a poultry animal, comprising administering to the poultry animal an effective amount of *M. elsdenii* cells.

In certain embodiments, the condition or disorder is acidosis.

In certain embodiments, the condition or disorder is respiratory disease.

In certain embodiments, the condition or disorder is an infection.

In certain embodiments, the infection is with *Salmonella* or *Campylobacter*.

The present disclosure is directed to a method for preventing or decreasing the growth of an opportunistic microorganism in the gastrointestinal tract of a poultry animal, comprising administering to the poultry animal an effective amount of *M. elsdenii* cells.

In certain embodiments, the opportunistic microorganism is pathogenic

In certain embodiments, the opportunistic microorganism is *Salmonella* or *Campylobacter*.

The present disclosure is directed to a method of improving the bioavailability of plant-derived phosphorous in the diet of a poultry animal, comprising administering to the poultry animal an effective amount of *M. elsdenii* cells.

The present disclosure is directed to a method of improving growth performance in a poultry animal, comprising administering to the poultry animal an effective amount of *M. elsdenii* cells, wherein the improved growth performance in the animal is an improvement in: feed intake, average daily gain, feed conversion ratio, carcass gain, egg production, bone mineralization, or combinations thereof.

In certain embodiments, the poultry animal is selected from the group consisting of: a chicken, a goose, a duck, a quail, a turkey, or a pigeon.

In certain embodiments, the poultry animal is selected from the group consisting of: a broiler, a broiler breeder, and a layer.

In certain embodiments, the poultry animal is a chicken.

The present disclosure is directed to a method for treating or preventing a condition or disorder associated with lactic acid production in the gastrointestinal tract of an equine, comprising administering to the equine an effective amount of *M. elsdenii* cells.

In certain embodiments, the condition or disorder is acidosis.

In certain embodiments, the condition or disorder is respiratory disease.

In certain embodiments, the condition or disorder is laminitis.

In certain embodiments, the condition or disorder is an infection.

In certain embodiments, the infection is with *Salmonella* or *Campylobacter*.

The present disclosure is directed to a method for preventing or decreasing the growth of an opportunistic microorganism in the gastrointestinal tract of an equine, comprising administering to the equine an effective amount of *M. elsdenii* cells.

In certain embodiments, the opportunistic microorganism is pathogenic

In certain embodiments, the opportunistic microorganism is *Salmonella* or *Campylobacter*.

The present disclosure is directed to a method of improving the bioavailability of plant-derived phosphorous in the diet of an equine, comprising administering to the equine an effective amount of *M. elsdenii* cells.

The present disclosure is directed to a method of improving growth performance in an equine, comprising administering to the equine an effective amount of *M. elsdenii* cells, wherein the improved growth performance in the animal is an improvement in: feed intake, average daily gain, feed conversion ratio, carcass gain, milk production, bone mineralization, or combinations thereof.

In certain embodiments, the equine is a horse, a pony, a donkey, or a mule.

In certain embodiments, a feed additive comprises the *M. elsdenii* cells.

In certain embodiments, the feed additive is a powder, granulate, particulate, pellet, cake, liquid, gel, or combinations thereof.

In certain embodiments, a composition comprises the *M. elsdenii* cells or a feed additive comprising the cells.

In certain embodiments, the composition is a capsule.

In certain embodiments, the *M. elsdenii* cells are freeze-dried cells.

In certain embodiments, the *M. elsdenii* cells are administered in a liquid.

In certain embodiments, the method further comprises rehydrating a feed additive or freeze-dried cells to produce the liquid.

In certain embodiments, the liquid is administered by oral gavage or by spraying the animal with the liquid.

In certain embodiments, the *M. elsdenii* cells are administered prior to, concomitantly with, or after feeding the animal with a food In certain embodiments, the administering comprises a single administration of the *M. elsdenii* cells.

In certain embodiments, the administering comprises a daily administration of the *M. elsdenii* cells.

In certain embodiments, the administering comprises more than one administration of the *M. elsdenii* cells on a single day.

The present disclosure is directed to a method of producing encapsulated freeze-dried *Megasphaera* cells, comprising: (a) preparing a culture under anaerobic conditions comprising *Megasphaera* cells and a growth media comprising at least two carbon sources selected from the group consisting of: casein, lactate, dextrose, fructose, fructan, glucose, sucrose, lactose, maltose, acetate, glycerol, mannitol, sorbitol, saccharose, xylose, molasses, fucose, glucosamine, dextran, a fat, an oil, glycerol, sodium acetate, arabinose, soy protein, soluble protein, raffinose, amylose, starch, tryptone, yeast extract, and combinations thereof, (b) harvesting the cells under anaerobic conditions, (c) freezing the cells, (d) freeze-drying the cells, and (e) encapsulating the cells, wherein about $1 \times 10^3$ to about $1 \times 10^{12}$ CFU/g of encapsulated freeze-dried *Megasphaera* cells are produced.

In certain embodiments, the method comprises administering to the animal encapsulated freeze-dried *Megasphaera* cells.

In certain embodiments, the method of improving growth performance in an animal comprises administering to the animal an effective amount of encapsulated freeze-dried *Megasphaera* cells.

In certain embodiments, the improved growth performance in the animal is an improvement in: feed intake, average daily gain, feed conversion ratio, carcass gain, milk production in a milk-producing animal, egg production in poultry, bone mineralization, or combinations thereof.

In certain embodiments, the method for preventing or decreasing the growth of an opportunistic microorganism in the gastrointestinal tract of an animal, comprises administering to the animal an effective amount of encapsulated freeze-dried *Megasphaera* cells.

In certain embodiments, the composition comprises encapsulated freeze-dried *Megasphaera* cells.

The present disclosure is directed to a method of producing freeze-dried anaerobic bacterial cells, comprising: (a) preparing a culture under anaerobic conditions or partial anaerobic conditions comprising anaerobic bacterial cells and a growth media comprising at least two carbon sources selected from the group consisting of: casein, lactate, dextrose, fructose, fructan, glucose, sucrose, lactose, maltose, acetate, glycerol, mannitol, sorbitol, saccharose, xylose, molasses, fucose, glucosamine, dextran, a fat, an oil, glycerol, sodium acetate, arabinose, soy protein, soluble protein, raffinose, amylose, starch, tryptone, yeast extract, and combinations thereof, (b) harvesting the cells under anaerobic conditions or partial anaerobic conditions, (c) freezing the cells, and (d) freeze-drying the cells, wherein about $1 \times 10^3$ to about $1 \times 10^{12}$ CFU/g of freeze-dried anaerobic bacterial cells are produced.

In certain embodiments, the method comprises administering to the animal freeze-dried anaerobic bacterial cells.

In certain embodiments, the method of improving growth performance in an animal comprises administering to the animal an effective amount of freeze-dried anaerobic bacterial cells.

In certain embodiments, the improved growth performance in the animal is an improvement in: feed intake, average daily gain, feed conversion ratio, carcass gain, milk production in a milk-producing animal, egg production in poultry, bone mineralization, or combinations thereof.

In certain embodiments, the method for preventing or decreasing the growth of an opportunistic microorganism in the gastrointestinal tract of an animal comprises administering to the animal an effective amount of freeze-dried anaerobic bacterial cells.

In certain embodiments, the composition comprises freeze-dried anaerobic bacterial cells.

The present disclosure is directed to a method of producing encapsulated freeze-dried anaerobic bacterial cells, comprising: (a) preparing a culture under anaerobic conditions or partial anaerobic conditions comprising anaerobic bacterial cells and a growth media comprising at least two carbon sources selected from the group consisting of: casein, lactate, dextrose, fructose, fructan, glucose, sucrose, lactose, maltose, acetate, glycerol, mannitol, sorbitol, saccharose, xylose, molasses, fucose, glucosamine, dextran, a fat, an oil, glycerol, sodium acetate, arabinose, soy protein, soluble protein, raffinose, amylose, starch, tryptone, yeast extract, and combinations thereof, (b) harvesting the cells under anaerobic conditions or partial anaerobic conditions, (c) freezing the cells, (d) freeze-drying the cells, and (e) encapsulating the cells, wherein about $1 \times 10^3$ to about $1 \times 10^{12}$ CFU/g of encapsulated freeze-dried anaerobic bacterial cells are produced.

In certain embodiments, the method comprises administering to the animal encapsulated freeze-dried anaerobic bacterial cells.

In certain embodiments, the method of improving growth performance in an animal comprises administering to the animal an effective amount of encapsulated freeze-dried anaerobic bacterial cells.

In certain embodiments, the improved growth performance in the animal is an improvement in: feed intake, average daily gain, feed conversion ratio, carcass gain, milk production in a milk-producing animal, egg production in poultry, bone mineralization, or combinations thereof.

In certain embodiments, the method for preventing or decreasing the growth of an opportunistic microorganism in the gastrointestinal tract of an animal comprises administering to the animal an effective amount of encapsulated freeze-dried anaerobic bacterial cells.

In certain embodiments, the composition comprises encapsulated freeze-dried anaerobic bacterial cells.

The present disclosure is directed to a method of producing freeze-dried aerobic bacterial and/or yeast cells, comprising: (a) preparing a culture under aerobic conditions comprising aerobic bacterial cells and/or yeast cells and a growth media comprising at least two carbon sources selected from the group consisting of: casein, lactate, dextrose, fructose, fructan, glucose, sucrose, lactose, maltose, acetate, glycerol, mannitol, sorbitol, saccharose, xylose, molasses, fucose, glucosamine, dextran, a fat, an oil, glycerol, sodium acetate, arabinose, soy protein, soluble protein, raffinose, amylose, starch, tryptone, yeast extract, and combinations thereof, (b) harvesting the cells, (c) freezing the cells, and (d) freeze-drying the cells, wherein about $1 \times 10^3$ to about $1 \times 10^{12}$ CFU/g of freeze-dried aerobic bacterial and/or yeast cells are produced.

In certain embodiments, the method comprises administering to the animal freeze-dried aerobic bacterial cells and/or yeast cells.

In certain embodiments, the method of improving growth performance in an animal comprises administering to the animal an effective amount of freeze-dried aerobic bacterial cells and/or yeast cells.

In certain embodiments, the improved growth performance in the animal is an improvement in: feed intake, average daily gain, feed conversion ratio, carcass gain, milk production in a milk-producing animal, egg production in poultry, bone mineralization, or combinations thereof.

In certain embodiments, the method for preventing or decreasing the growth of an opportunistic microorganism in the gastrointestinal tract of an animal comprises administering to the animal an effective amount of freeze-dried aerobic bacterial cells and/or yeast cells.

In certain embodiments, the composition comprises freeze-dried aerobic bacterial cells and/or yeast cells.

The present disclosure is directed to a method of producing encapsulated freeze-dried aerobic bacterial cells and/or yeast cells, comprising: (a) preparing a culture under aerobic conditions comprising aerobic bacterial cells and/or yeast cells and a growth media comprising at least two carbon sources selected from the group consisting of: casein, lactate, dextrose, fructose, fructan, glucose, sucrose, lactose, maltose, acetate, glycerol, mannitol, sorbitol, saccharose, xylose, molasses, fucose, glucosamine, dextran, a fat, an oil, glycerol, sodium acetate, arabinose, soy protein, soluble protein, raffinose, amylose, starch, tryptone, yeast extract, and combinations thereof, (b) harvesting the cells under aerobic conditions, (c) freezing the cells, (d) freeze-drying the cells, and (e) encapsulating the cells, wherein about $1\times10^3$ to about $1\times10^{12}$ CFU/g of encapsulated freeze-dried aerobic bacterial cells and/or yeast cells are produced.

In certain embodiments, the method comprises administering to the animal encapsulated freeze-dried aerobic bacterial cells and/or yeast cells.

In certain embodiments, the method of improving growth performance in an animal comprises administering to the animal an effective amount of encapsulated freeze-dried aerobic bacterial cells and/or yeast cells.

In certain embodiments, the improved growth performance in the animal is an improvement in: feed intake, average daily gain, feed conversion ratio, carcass gain, milk production in a milk-producing animal, egg production in poultry, bone mineralization, or combinations thereof.

In certain embodiments, the method for preventing or decreasing the growth of an opportunistic microorganism in the gastrointestinal tract of an animal comprises administering to the animal an effective amount of encapsulated freeze-dried aerobic bacterial cells and/or yeast cells.

In certain embodiments, the composition comprises encapsulated freeze-dried aerobic bacterial cells and/or yeast cells.

BRIEF DESCRIPTION OF THE DRAWINGS/FIGURES

Figure 4:
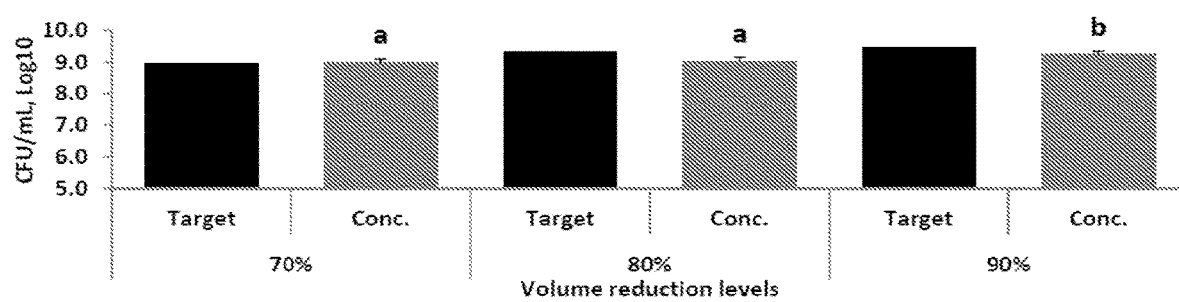

FIG. 4 shows yield of *M. elsdenii* cells in CFU/mL of retentate on the y-axis in Log 10 scale after processing through the TFF system. The x-axis indicates a 70/6, 80%, or 90% volume reduction by the system. "Target" refers to the theoretical recovery of *M. elsdenii* cells after TFF processing. "Conc." refers to the actual recovery of *M. elsdenii* cells in the retentate, which is the volume of concentrated cells remaining after the noted volume reductions.

Figure 5:
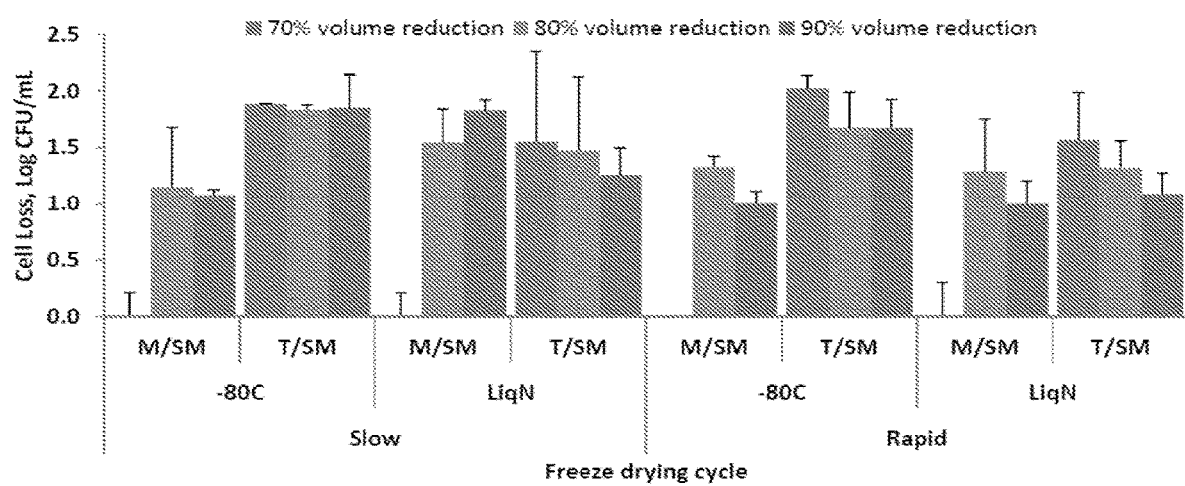

FIG. 5 shows cell loss following freezing of cells at $-80°$ C. or in liquid nitrogen (LiqN) and freeze-drying of cells using a slow (38 hours at 135 mTorr) or rapid (18.5 hours at 250 mTorr) cycle. The cells were from retentates after 70%, 80%, or 90% volume reduction with TFF of cultures having either 8% maltodextrin/15% skim milk (M/SM) or 8% trehalose/15% skim (T/SM) as cryoprotectants.

Figure 6:
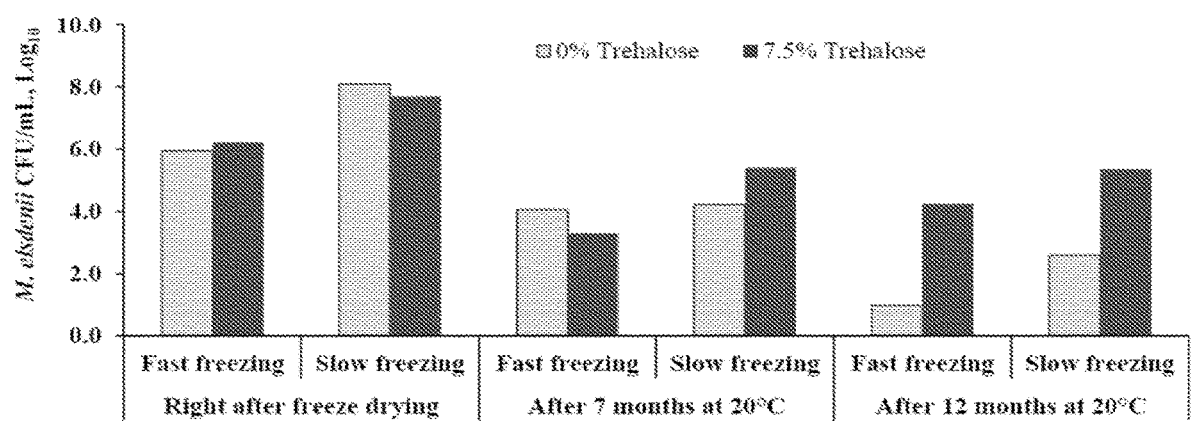

FIG. 6 shows yield of *M. elsdenii* NCIMB 41125 cells after an initial fast (liquid nitrogen) or slow ($-20°$ C.) freezing followed by freeze-drying (in the presence of 15% maltodextrin and 0% or 7.5% trehalose.

Figure 7:
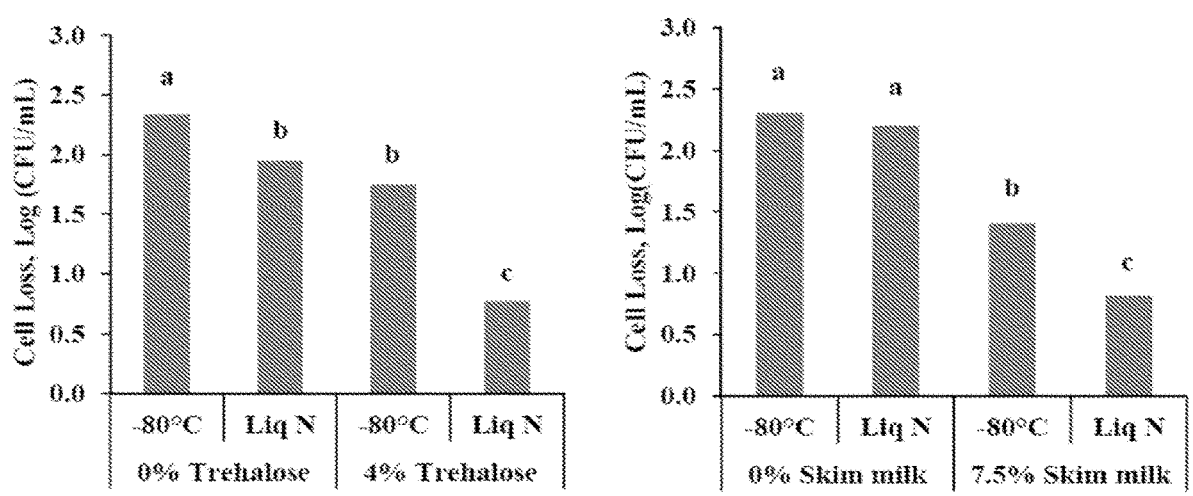

FIG. 7 shows cell loss observed in *M. elsdenii* NCIMB 41125 cells frozen with or without 4% trehalose or 7.5% skim milk at either $-80°$ C. or in liquid nitrogen (LiqN).

Figure 8:
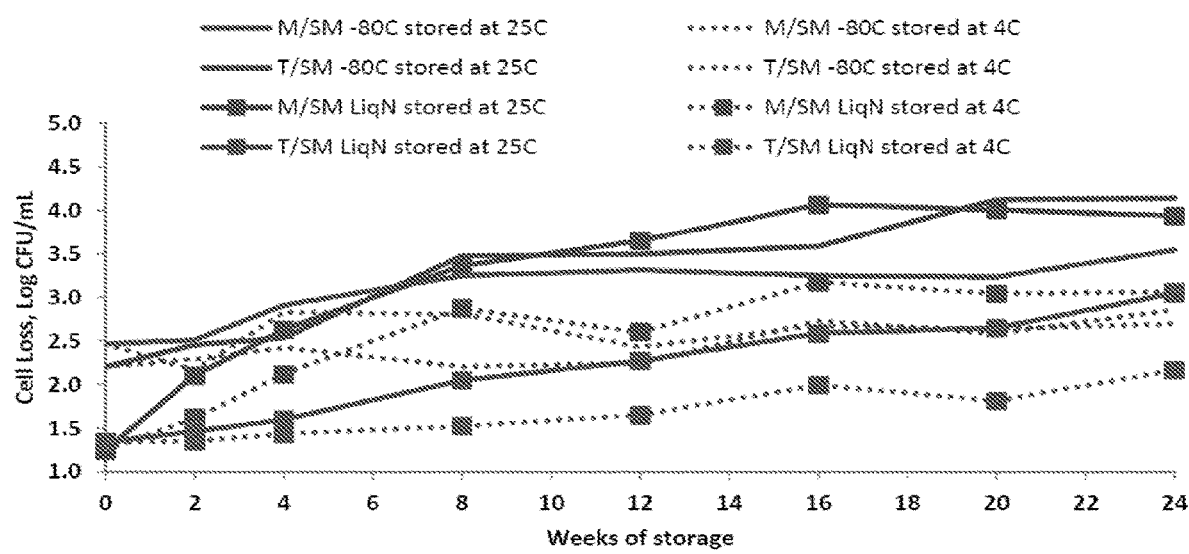

FIG. 8 shows cell loss observed on freeze-dried samples obtained from 90% volume reduction retentate, mixed with 8% trehalose/15% skim milk (T/SM) or 8% maltodextrin/15% skim milk (M/SM), frozen at $-80°$ C. or in liquid nitrogen (LiqN), and freeze-dried using the rapid cycle and stored at room temperature or 4° C. under anaerobic conditions for up to 24 weeks.

Figure 9:
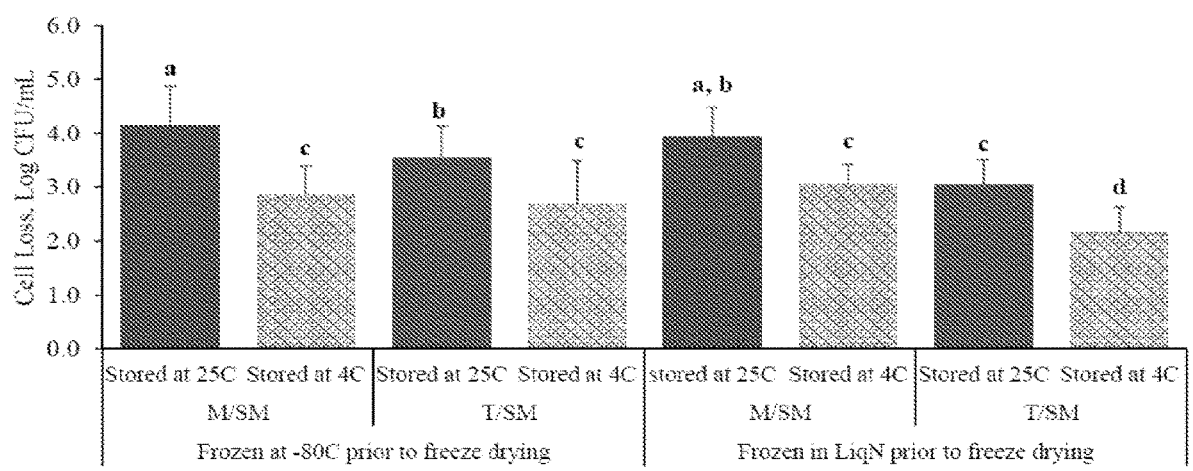

FIG. 9 shows cell loss observed on freeze-dried samples obtained from 90% volume reduction retentate, mixed with 8% trehalose/15% skim milk (T/SM) or 8% maltodextrin/15% skim milk (M/SM), frozen at $-80°$ C. or in liquid nitrogen (LiqN), and freeze-dried using the rapid cycle and stored at room temperature or 4° C. under anaerobic conditions for 24 weeks. Bars without a common superscript are statistically different, $P<0.02$.

Figure 10:
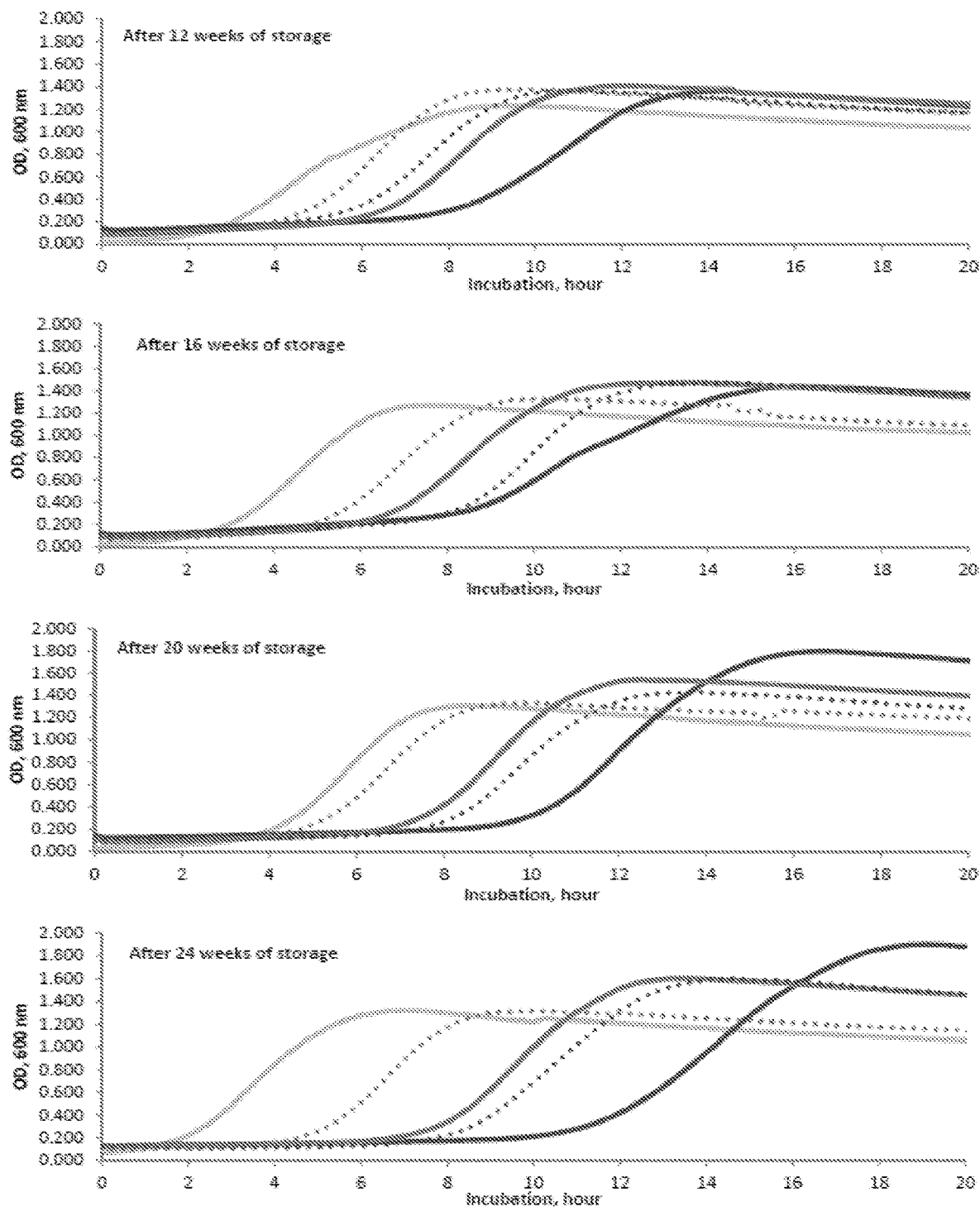

FIG. 10 shows growth curves performed on non-freeze-dried or rehydrated freeze-dried product obtained from 90% volume reduction retentate, mixed with 8% trehalose/15% skim milk (T/SM) or 8% maltodextrin/15% skim milk (M/SM), frozen in liquid nitrogen (LiqN), and freeze-dried using the rapid cycle after 12, 16, 20 or 24 weeks of storage under anaerobic conditions at 4 or 25° C. Optical density (OD) is shown at 600 nanometers (nm) as measured from 0 hours to 20 hours. Yellow lines=non-freeze-dried, Red lines=T/SM, Blue lines=M/SM, Dotted lines=stored at 4° C., and Full lines=stored at 25° C.

Figure 11:
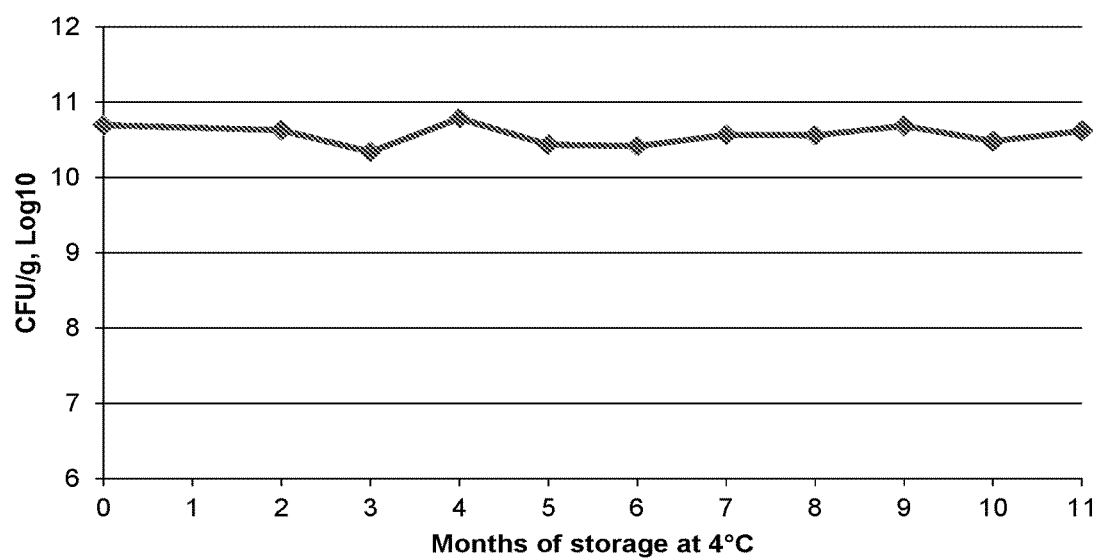

FIG. 11 shows *M. elsdenii* in CFU per gram ("CFU/g") in Log 10 scale from freeze-dried vials stored at 4° C. for up to 11 months. Each data point corresponds to the average yield of 3 vials from 2 different freeze drying runs (6 vials total).

Figure 12:
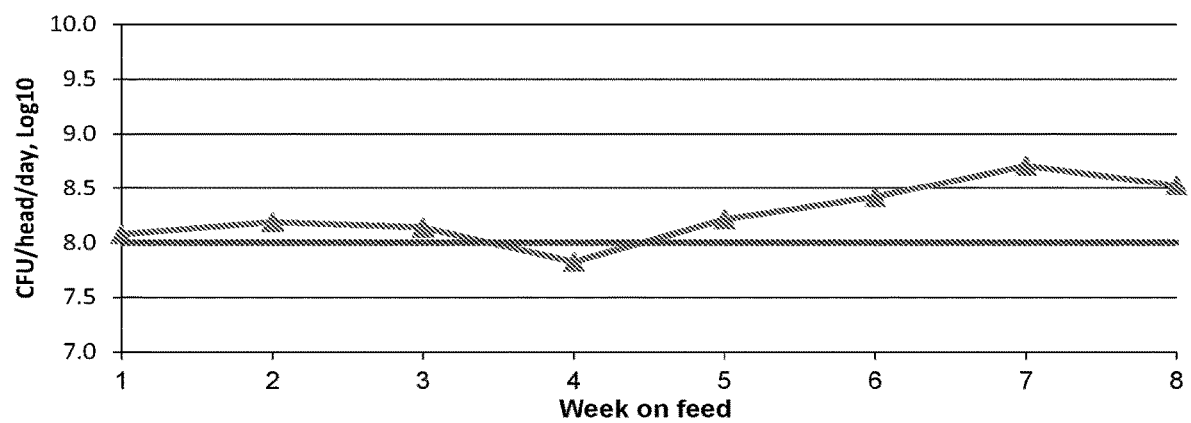

FIG. 12 shows *M. elsdenii* concentration (CFU/head/day) in freeze-dried product given daily as a top-dress treatment (i.e., a treatment added to an animal feed by mixing the treatment into the feed or placing the treatment on top of the feed). The week of sampling is shown on the x-axis, sampling effect, $P<0.0001$. The solid horizontal line represents the target *M. elsdenii* concentration (CFU/head/day) to be delivered daily.

Figure 13:
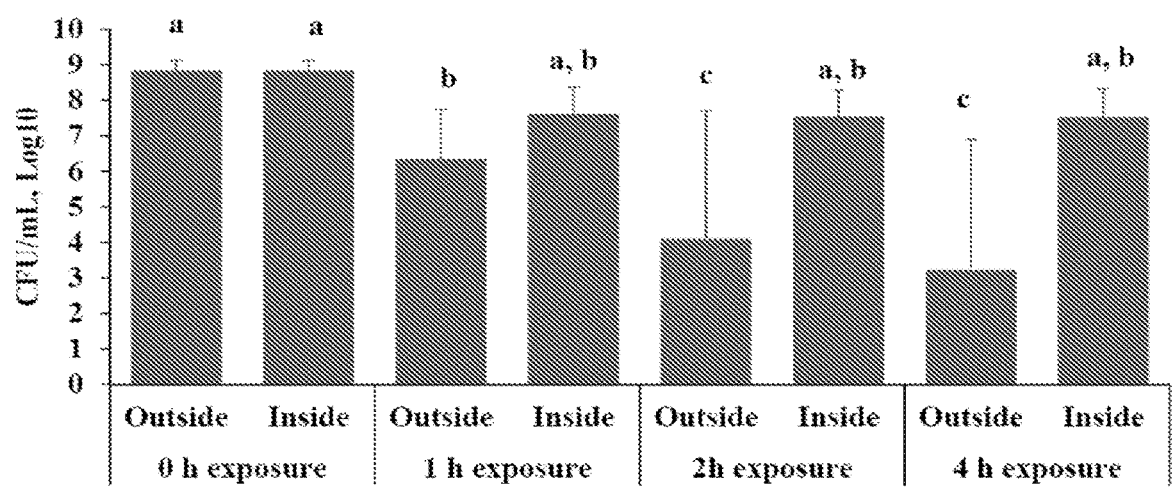

FIG. 13 shows *M. elsdenii* concentration in ground corn top-dressed with freeze-dried product and exposed for 0 to 4 hours to atmospheric conditions in the laboratory at room temperature without direct exposure to the sun (Inside) or outside in average daily temperatures of up to 95° F. with direct exposure to the sun (Outside). Combined effect of exposure time and storage conditions, $P=0.0007$; Exposure time effect, $P<0.0001$; Storage conditions effect, $P<0.0001$.

Figure 14:
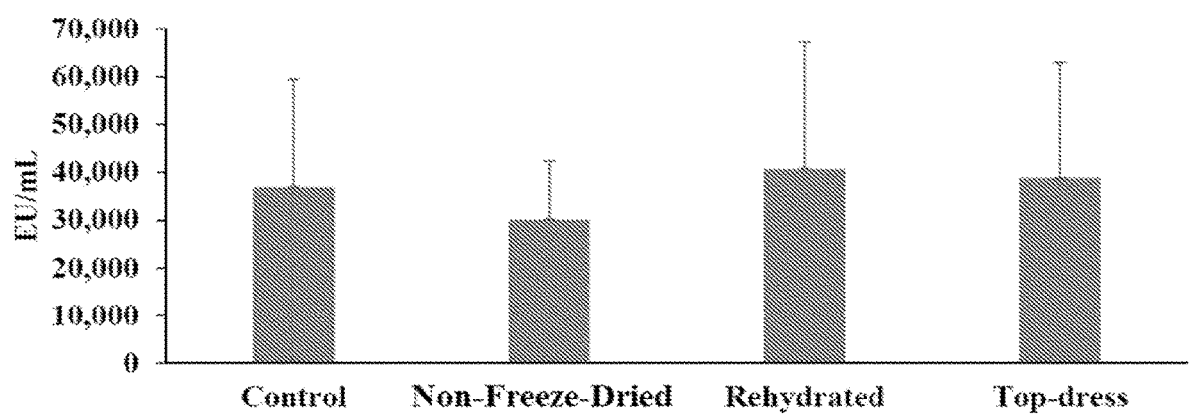

FIG. 14 shows endotoxin concentration (EU/mL) in rumen fluid samples (measured as an indicator of bacterial lysis in the rumen) obtained 26 hours after the first feeding for each group: Control group (received no *M. elsdenii*), Non-Freeze-Dried group (received 50 mL of *M. elsdenii* liquid culture containing $10^{10}$ CFU *M. elsdenii*), Rehydrated group (received lyophilized culture that was rehydrated immediately prior to administration, containing $10^{10}$ CFU of *M. elsdenii*), and Top-dress group (received lyophilized culture that was rehydrated immediately prior to administration, containing $10^{10}$ CFU of *M. elsdenii*, and also received lyophilized *M. elsdenii* product incorporated as a daily top-dress containing $10^8$ CFU of *M. elsdenii*). Effect of treatment, $P=0.3462$.

Figure 15:
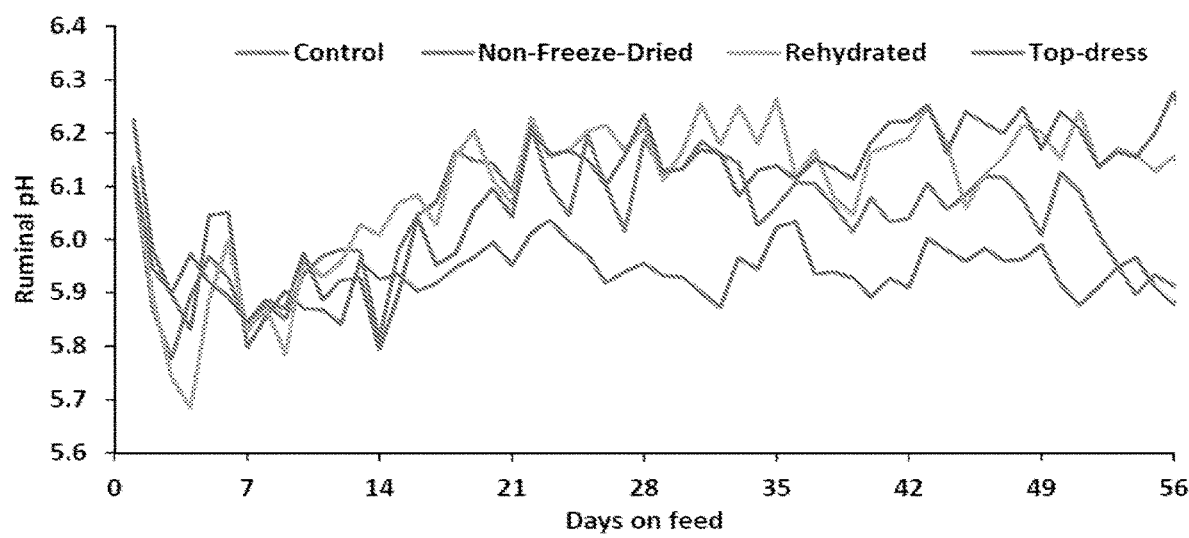

FIG. 15 shows ruminal pH measured at 1-hour intervals for each group: Control group (received no *M. elsdenii*), Non-Freeze-Dried group (received 50 mL of *M. elsdenii* liquid culture containing $10^{10}$ CFU *M. elsdenii*), Rehydrated group (received lyophilized culture that was rehydrated immediately prior to administration, containing $10^{10}$ CFU of

*M. elsdenii*), and Top-dress group (received lyophilized culture that was rehydrated immediately prior to administration, containing $10^{10}$ CFU of *M. elsdenii*, and received lyophilized *M. elsdenii* product incorporated as a daily top-dress containing $10^8$ CFU of *M. elsdenii*). Combined effect of treatment and day, P<0.001, Effect of treatment, P<0.001, Effect of day, P<0.001. Standard Error of the Mean (SEM)=0.041.

Figure 16:
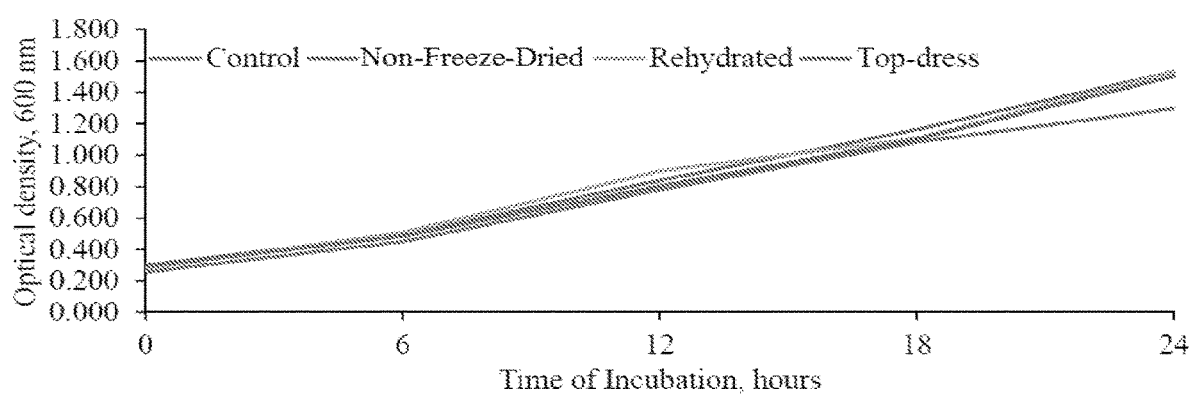

FIG. 16 shows changes in optical density at 600 nm of a semi-defined lactate medium inoculated with ruminal fluid for each group: Control group (received no *M. elsdenii*), Non-Freeze-Dried group (received 50 mL of *M. elsdenii* liquid culture containing $10^{10}$ CFU *M. elsdenii*), Rehydrated group (received lyophilized culture that was rehydrated immediately prior to administration, containing $10^{10}$ CFU of *M. elsdenii*), and Top-dress group (received lyophilized culture that was rehydrated immediately prior to administration, containing $10^{10}$ CFU of *M. elsdenii*, and also received lyophilized *M. elsdenii* product incorporated as a daily top-dress containing $10^8$ CFU of *M. elsdenii*). Combined effect of treatment and time, P<0.02; Effect of treatment, P<0.01; Effect of time, P<0.01. SEM=0.04.

Figure 17:
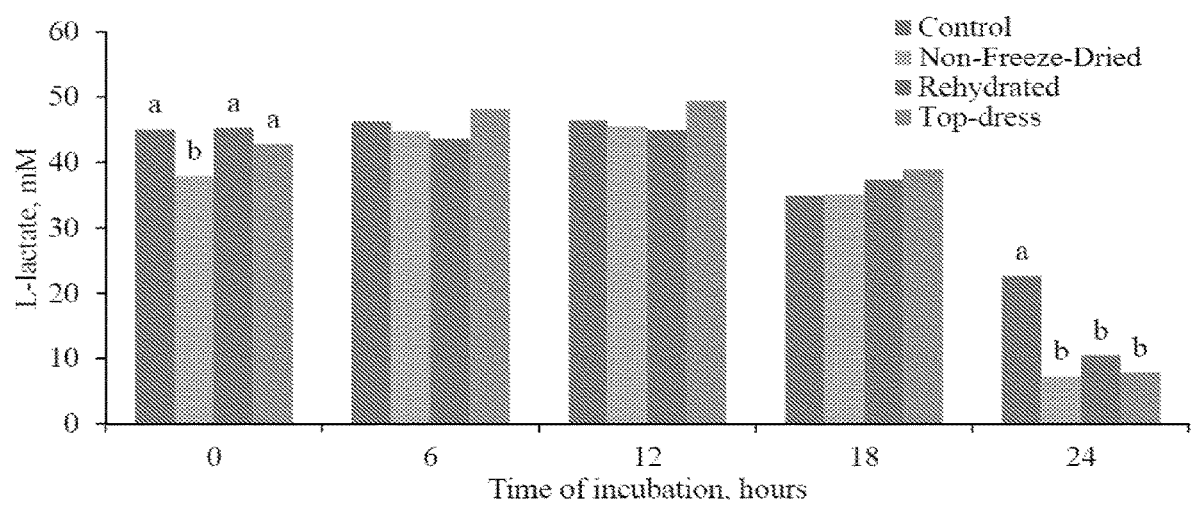

FIG. 17 shows changes in L-lactate concentration (mM) of a semi-defined lactate medium inoculated with mixed ruminal microbes for each group: Control group (received no *M. elsdenii*), Non-Freeze-Dried group (received 50 mL of *M. elsdenii* liquid culture containing $10^{10}$ CFU *M. elsdenii*), Rehydrated group (received lyophilized culture that was rehydrated immediately prior to administration, containing $10^{10}$ CFU of *M. elsdenii*), and Top-dress group (received lyophilized culture that was rehydrated immediately prior to administration, containing $10^{10}$ CFU of *M. elsdenii*, and also received lyophilized *M. elsdenii* product incorporated as a daily top-dress containing $10^8$ CFU of *M. elsdenii*).$^{a,b,c}$ bars with different superscripts are statistically different from one another, P<0.05.

Figure 18:
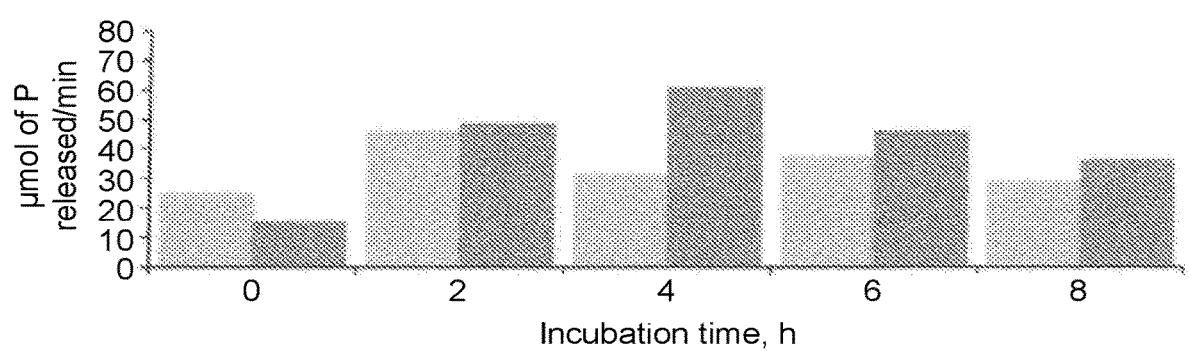

FIG. 18 shows phytase activity in *Megasphaera elsdenii* NCIMB 41125 cells. The x-axis indicates cell samples taken from cultures of *Megasphaera elsdenii* NCIMB 41125 cells from the start of culture ("0" hours) and at 2 hour intervals thereafter, i.e., at "2," "4," "6," and "8" hours after the start of culture. Phytase activity is shown on the y-axis as the amount of inorganic phosphorus released from cell pellets of the samples in micromoles per minute ("µmol of P released/min"). Phytase activity in cells cultured in media containing inorganic phosphate ($KH_2PO_4$) is shown in light grey, while phytase activity in cells cultured in media containing phytate is shown in dark grey.

Figure 19:
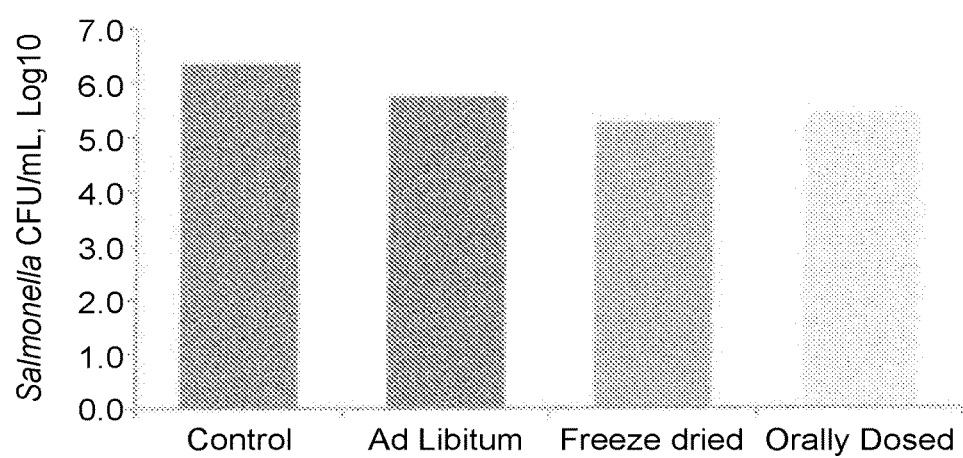

FIG. 19 shows the effect of *Megasphaera elsdenii* on *Salmonella* concentration in cecal samples from 15 day-old broiler chicks. The x-axis indicates treatment with no *Megasphaera elsdenii* ("Control"), ad libitum free access to bottle feeders containing liquid *Megasphaera elsdenii* ("Ad Libitum"), daily freeze-dried *Megasphaera elsdenii* ("Freeze-dried"), or an oral gavage of liquid *Megasphaera elsdenii* on day 0. The y-axis indicates the *Salmonella* concentration in colony forming units per milliliter (CFU/mL) in Log 10 scale for the treatment groups.

Figure 20:
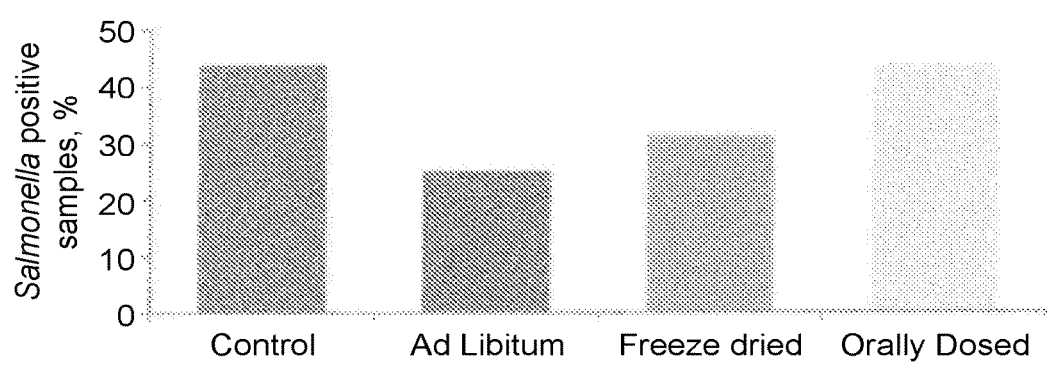

FIG. 20 shows the prevalence of *Salmonella* in cecal samples from 15 day-old broiler chicks. The x-axis shows the treatment groups. The y-axis indicates the percentage of cecal samples that were positive for *Salmonella*.

Figure 21:
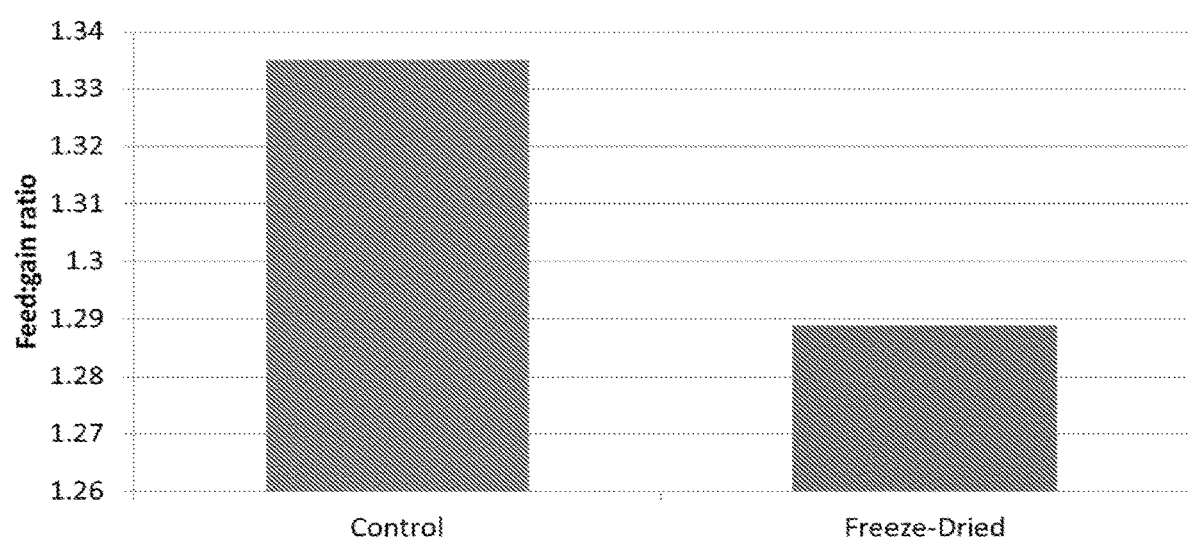

FIG. 21 shows the feed to gain ratio (y-axis) in 18 day-old broiler chicks treated with no *Megasphaera* ("Control") or with freeze-dried *Megasphaera elsdenii* ("Freeze-Dried"). The feed to gain ratio is a ratio of the total feed consumed to the total weight gained.

Figure 22:
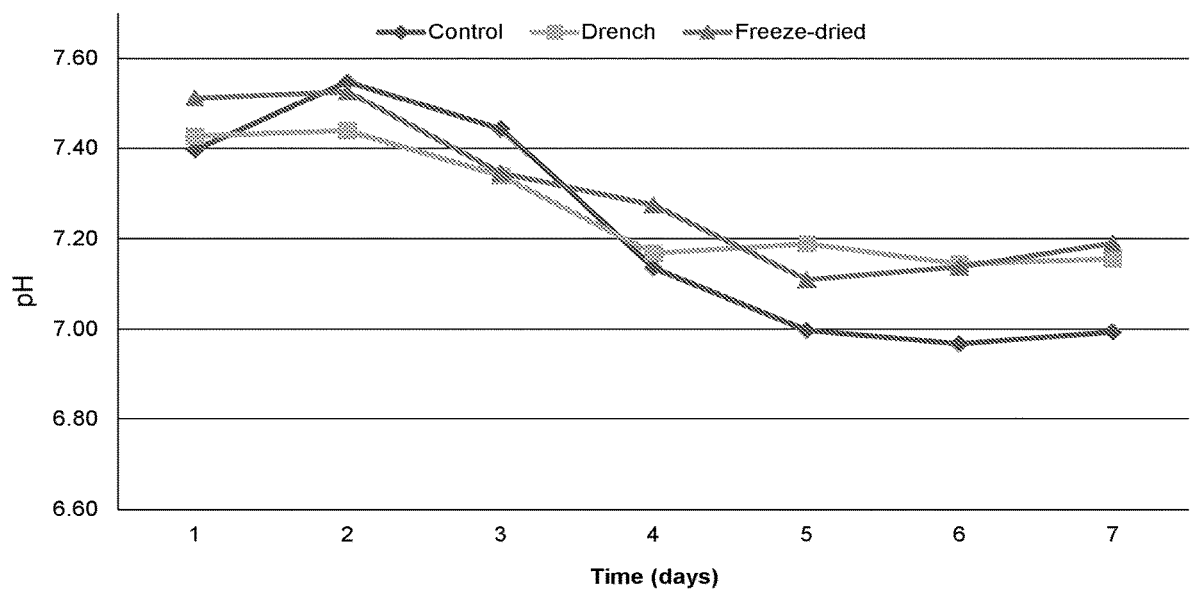

FIG. 22 shows the pH in cecal samples from horses treated with no *Megasphaera elsdenii* ("Control"), an oral drench of *Megasphaera elsdenii* ("Drench") on day 1 of each 7 day treatment period, or daily freeze-dried *Megasphaera elsdenii* ("Freeze-dried").

Figure 23:
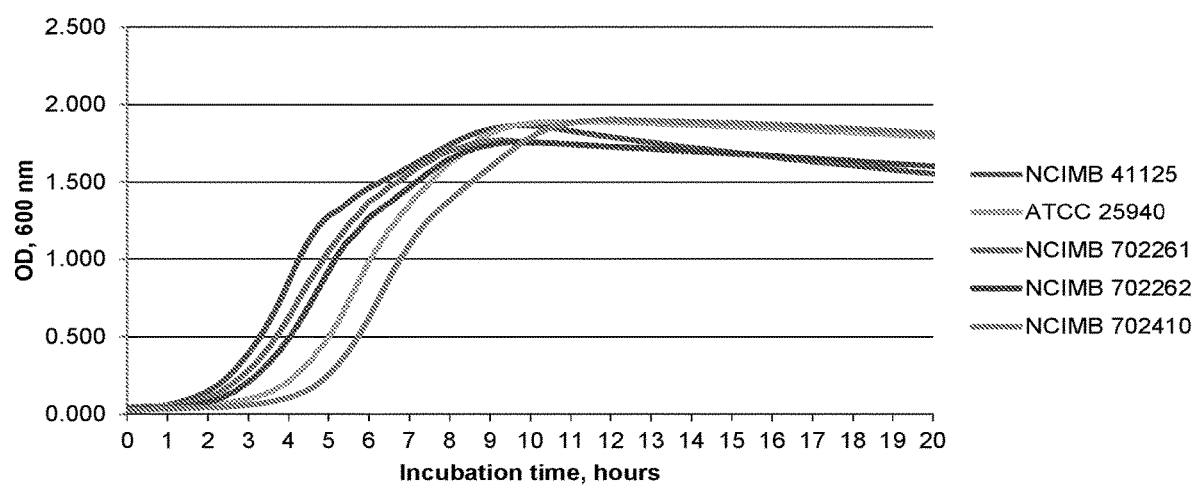

FIG. 23 shows the growth of *M. elsdenii* strains (NCIMB 41125, ATCC 25940, NCIMB 702261, NCIMB 702262, and NCIMB 702410) on semi-defined media containing 70% lactate and 30% glucose.

Figure 24:
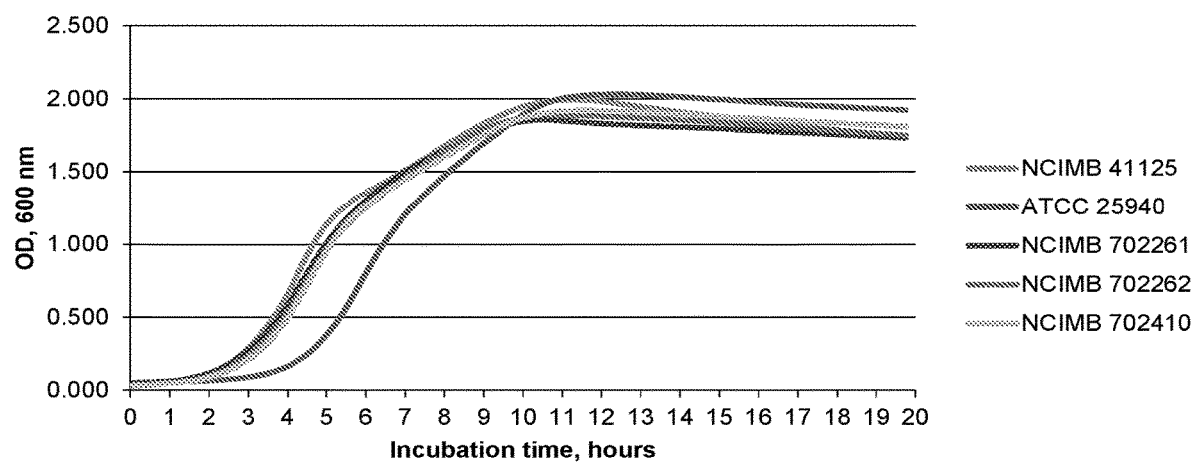

FIG. 24 shows the growth of *M. elsdenii* strains (NCIMB 41125, ATCC 25940, NCIMB 702261, NCIMB 702262, and NCIMB 702410) on semi-defined media containing 60% lactate and 40% glucose.

Figure 25:
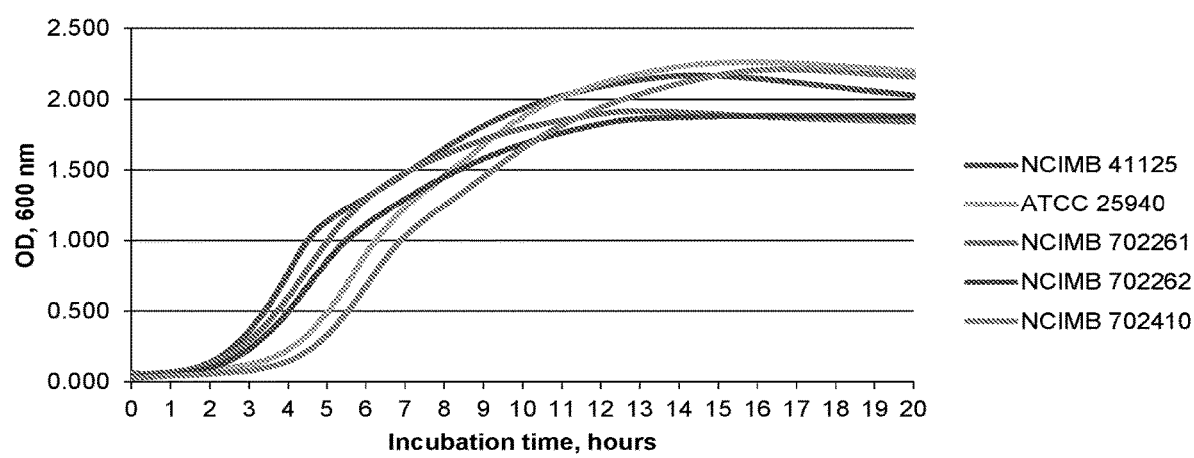

FIG. 25 shows the growth of *M. elsdenii* strains (NCIMB 41125, ATCC 25940, NCIMB 702261, NCIMB 702262, and NCIMB 702410) on semi-defined media containing 40% lactate and 60% glucose.

Figure 26:
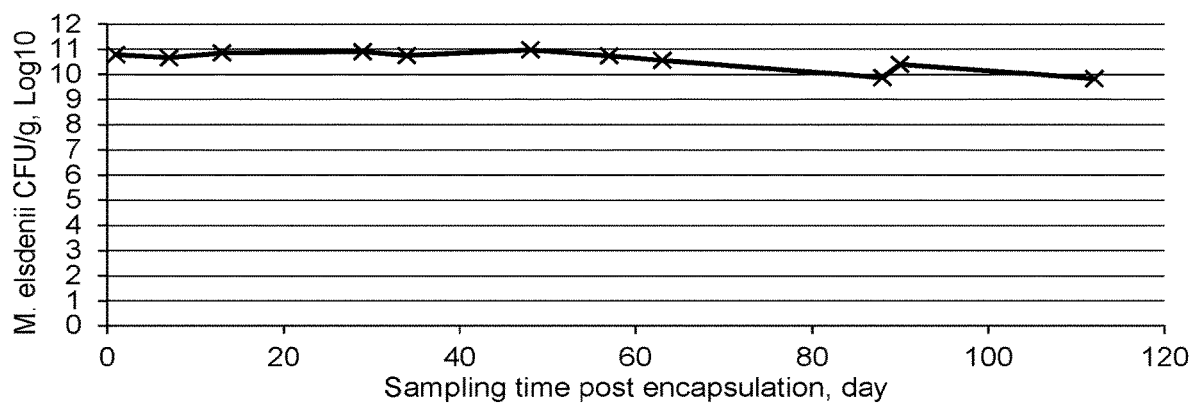

FIG. 26 shows the stability of freeze-dried *M. elsdenii* encapsulated using method 2 and stored at room temperature in an aerobic environment.

Figure 27:
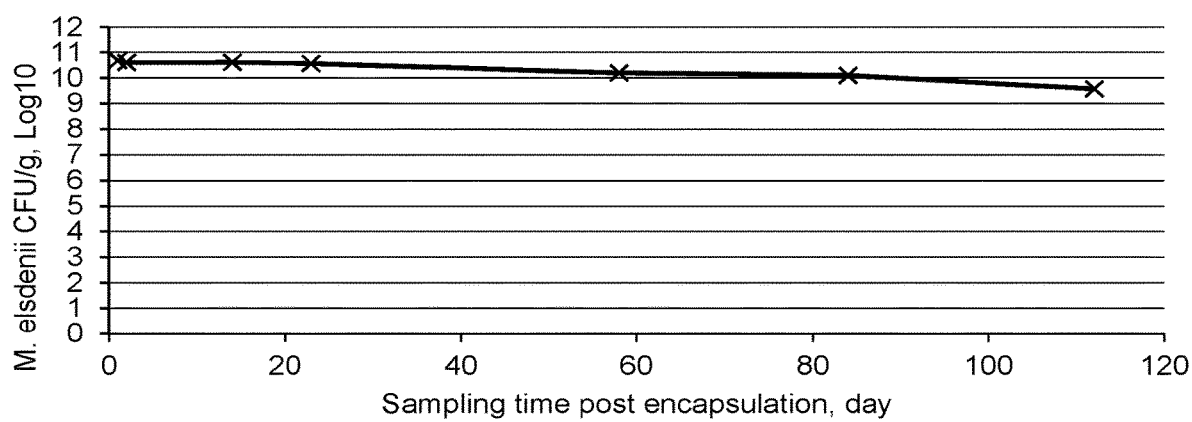

FIG. 27 shows the stability of freeze-dried *M. elsdenii* encapsulated using method 3 and stored at room temperature in an aerobic environment.

Figure 28:
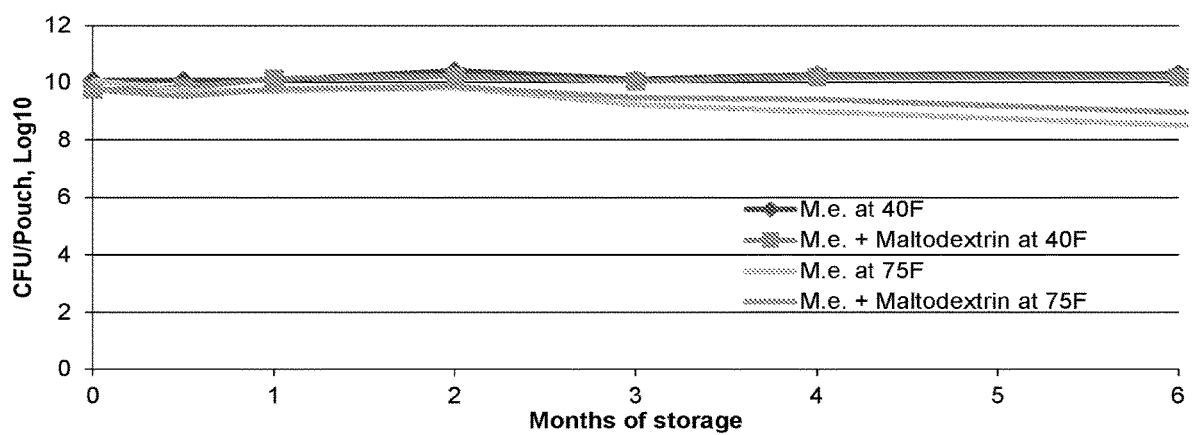

FIG. 28 shows *M. elsdenii* NCIMB 41125 concentration (Log 10 CFU/Pouch) in freeze dried product stored in Mylar pouch with (M.e.+Maltodextrin) or without maltodextrin (M.e.) at 40 or 75° F.

DETAILED DESCRIPTION OF THE INVENTION

The present invention relates to *Megasphaera elsdenii* cells, methods for producing *M. elsdenii* cells, feed additives and compositions comprising the cells, and uses involving administration of the cells to animals, including, e.g., for improved growth performance and/or health. The present invention also relates to microbial cells, including but not limited to aerobic bacteria, anaerobic bacteria, and yeast, and for example, *Bifidobacterium*, such as *B. breve*, *Lactobacillus*, such as *L. plantarum*, *Bifidobacterium*, such as *B. animalis* subsp. *lactis*, *Pediococcus*, such as *P. acidilactici*, *Lactobacillus*, such as *L. casei*, *Bacillus*, such as *B. subtilis*, *Saccharomyces*, such as *S. boulardii* and *S. cerevisiae*, and methods for producing microbial cells, feed additives and compositions comprising the microbial cells, and uses involving administration of the microbial cells to animals, including, e.g., for improved growth performance and/or health.

All publications, patents, and other references mentioned herein are incorporated by reference in their entireties for all purposes as if each individual publication or patent application were specifically and individually indicated to be incorporated by reference. In addition, citation or identification of any reference in this application shall not be construed as an admission that such reference is available as prior art to the present invention.

Terminology

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular.

To the extent that section headings are used, they should not be construed as necessarily limiting.

As used herein and in the appended claims, the singular forms "a," "an," and "the" include plural references unless the context clearly dictates otherwise. For example, the term "a compound" or "at least one compound" may include a plurality of compounds, including mixtures thereof. The terms "a", "an," "the," "one or more," and "at least one," for example, can be used interchangeably herein.

As used herein, the term "about," when used to modify an amount related to the invention, refers to variation in the numerical quantity that can occur, for example, through routine testing and handling; through inadvertent error in such testing and handling; through differences in the manufacture, source, or purity of ingredients employed in the invention; and the like. Whether or not modified by the term "about", the claims include equivalents of the recited quantities. In some embodiments, the term "about" means plus or minus 10% of the reported numerical value.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range, such as from 1 to 6 should be considered to have specifically disclosed subranges such as from 1 to 2, from 1 to 3, from 1 to 4, from 1 to 5, from 2 to 3, from 2 to 4, from 2 to 5, from 2 to 6, from 3 to 4, from 3 to 5, from 3 to 6, etc., as well as individual numbers within that range, for example, 1, 2, 3, 4, 5, and 6. This applies regardless of the breadth of the range.

The terms "comprises," "comprising," "includes," "including," "having," and their conjugates are interchangeable and mean "including but not limited to." It is understood that wherever aspects are described herein with the language "comprising," otherwise analogous aspects described in terms of "consisting of" and/or "consisting essentially of" are also provided.

The term "consisting of" means "including and limited to."

The term "consisting essentially of" means the specified material of a composition, or the specified steps of a method, and those additional materials or steps that do not materially affect the basic characteristics of the material or method.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "culture," "to culture," and "culturing," as used herein, means to incubate cells under in vitro conditions that allow for cell growth or division or to maintain cells in a living state. The term "a culture" can also be used herein to refer to cells incubated under in vitro conditions (e.g., cells incubated a liquid growth media).

The term "probiotic" as used herein refers to one or more live microorganisms (bacteria and/or yeast) and may or may not include other ingredients, which when administered in adequate amounts may confer a health, digestive, and/or performance benefit on the animal or subject.

The term "direct-fed microbial product" as used in herein refers to a product that contains one or more live microorganisms (bacteria and/or yeast) and may or may not include other ingredients, that can be administered to the animal or subject in feed mixtures, boluses, and/or oral pastes, and when administered in adequate amounts may confer a health benefit on the animal or subject.

The term "feed additive" as used herein refers to one or more ingredients, products, or substances (e.g., cells), used alone or together, in nutrition (e.g., to improve the quality of a food (e.g., an animal feed), to improve an animal's performance and health, and/or to enhance digestibility of a food or materials within a food). A feed additive can be, for example, a probiotic.

The terms "growth media" and "culture media" as used herein refer to a solid (e.g., agar), semi-solid (e.g., agar), or liquid (e.g., broth) composition that contains components to support the growth of cells.

The terms "harvest" and "harvesting" as used herein refer to collecting cells from a culture, e.g., collecting cells in growth media from the culture, collecting cells by removing an amount of the growth media from the cells (e.g., by concentrating the cells in a liquid culture or separating the cells from the growth media), or halting the culturing of the cells. The terms include collecting or removing a volume of liquid comprising the cells from a liquid culture, including a volume in which the cells have been concentrated.

The term "isolated" as used herein does not necessarily reflect the extent to which an isolate has been purified, but indicates isolation or separation from a native form or native environment. An isolate can include, but is not limited to, an isolated microorganism, an isolated biomass, or an isolated culture.

The term "effective amount" as used herein refers to an amount that achieves a desired result.

As used herein, a "therapeutically effective amount" or "clinically effective amount" refers to an amount, that achieves a desired therapeutic result, including, e.g., an amount whether used alone or in combination with other components. A therapeutic result can be, e.g., lessening of symptoms, prolonged survival, improved mobility, and the like. A therapeutic result need not be a "cure."

As used herein, "excipient" refers to a component, or mixture of components, that is used to give desirable characteristics to a feed additive, food, or composition as disclosed herein. An excipient of the present invention can be described as a "pharmaceutically acceptable" excipient when added to a pharmaceutical composition, meaning that the excipient is a compound, material, composition, salt, and/or dosage form which is, within the scope of sound medical judgment, suitable for contact with tissues of animals (i.e., humans and non-human animals) without excessive toxicity, irritation, allergic response, or other problematic complications over the desired duration of contact commensurate with a reasonable benefit/risk ratio.

The terms "treat," "treating," and "treatment" refer to both therapeutic treatment and prophylactic or preventative measures, wherein the object is to prevent or slow down (lessen) an undesired physiological condition, disease, or disorder, or to obtain beneficial or desired physiological results (e.g., clinical, medical, and/or veterinary results). For purposes of this invention, beneficial or desired results include, but are not limited to, alleviation or elimination of the symptoms or signs associated with a condition, disease, or disorder; diminishment of the extent of a condition, disease, or disorder; stabilization of a condition, disease, or disorder, (i.e., where the condition, disease, or disorder is not worsening); delay in onset or progression of the condition, disease, or disorder; amelioration of the condition, disease, or disorder; remission (whether partial or total and whether detectable or undetectable) of the condition, disease, or disorder; or enhancement or improvement of a condition, disease, or disorder. Treatment includes eliciting a physiologically significant response without excessive side effects. Treatment also includes prolonging survival as compared to expected survival if not receiving treatment.

As used herein, the terms "prevent" and "preventing" refer to partially or completely delaying onset of an infection, disease, disorder, and/or condition; partially or completely delaying onset of one or more signs, symptoms, features, or manifestations (e.g., clinical or physiological signs, symptoms, features, or manifestations) of a particular infection, disease, disorder, and/or condition; partially or completely delaying progression from an infection, a particular disease, disorder, and/or condition; and/or decreasing the risk of developing a pathology associated with the infection, the disease, disorder, and/or condition.

As used herein, the term "yield" refers to the amount of living, or viable, cells, including the amount in a particular volume (e.g., colony-forming units per milliliter ("CFU/mL")) or in a particular weight (e.g., CFU per gram ("CFU/g")).

As used herein, the term "viable" refers to a living organism or organisms (e.g., a microbial cell that is alive or microbial cells that are alive). "Viability" refers to the ability to live, especially under certain conditions.

As used herein, "purify," "purified," and "purification" mean to make substantially pure or clear from unwanted components, material defilement, admixture or imperfection.

The terms "invention" and "disclosure" can be used interchangeably when describing or used, for example, in the phrases "the present invention" or "the present disclosure."

The terms "animal" or "subject" refer to any organism belonging to the kingdom Animalia and includes, without limitation, aquatic animals and terrestrial animals such as fish; commercial fish; ornamental fish; fish larvae; bivalves; mollusks; crustaceans; shellfish; shrimp; larval shrimp; artemia; rotifers; brine shrimp; filter feeders; amphibians; reptiles; mammals; humans; non-human animals; domestic animals; farm animals; zoo animals; sport animals; breeding stock; racing animals; show animals; heirloom animals; rare or endangered animals; companion animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, ponies, donkeys, mules, and zebras; food animals such as cows, buffalo, cattle, pigs, poultry, and sheep; ungulates such as deer and giraffes; avians (i.e., birds); poultry such as chickens, geese, ducks, quails, turkeys, pigeons, emus, ostriches, and any other bird used as a food or farm animal, including broilers, broiler breeders, and a layers; rodents such as mice, rats, hamsters and guinea pigs; and so on. An animal feed includes, but is not limited to, an aquaculture feed, a domestic animal feed including a pet feed, a zoological animal feed, a work animal feed, a livestock feed, and combinations thereof. A food includes animal feed and human food.

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable subcombination or as suitable in any other described embodiment of the invention. Certain features described in the context of various embodiments are not to be considered essential features of those embodiments, unless the embodiment is inoperative without those elements.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

Megasphaera elsdenii

Megasphaera elsdenii cells from any strain or any combination of strains can be used in the invention described herein.

A M. elsdenii strain or strains can be selected from a stock culture collection (e.g., American Type Culture Collection ("ATCC®"), National Collection of Industrial, Food and Marine Bacteria ("NCIMB"), National Collection of Type Cultures ("NCTC"), American Research Service ("ARC") culture collection (i.e., "NRRL"), National Institute of Animal Health (NIAH) culture collection), or can be a strain that has been isolated from a natural source (e.g., from the gastrointestinal tract of a ruminant).

Examples of M. elsdenii strains that can be selected from a culture collection include, but are not limited to, the strains listed by deposit numbers in Table 1. Alternative designations of the deposit numbers are also indicated.

TABLE 1

Examples of M. elsdenii Strains and Source of Each Strain.

| Deposit Number | Alternative Designations | Source of Strain |
|---|---|---|
| ATCC ® 25940 | NCIMB 8927; BE2-2083 | Rumen of Sheep |
| ATCC ® 17752 | B159; NCIMB 702409; NCDO2409 | N/A |
| ATCC ® 17753 | T81; NCIMB 702410; NCDO2410 | N/A |
| NCIMB 702261 | A17-2; A12-2; NCDO2261 | Human Adult Faeces |
| NCIMB 702262 | S17-3; NCDO2262 | Juvenile Swine Faeces |
| NCIMB 702264 | LC1 | N/A |
| NCIMB 702331 | LC1; NCDO2263; NCDO2264; NCDO2331; | N/A |
| NCIMB 41125 | | Rumen of Dairy Cow |
| NCIMB 41787 | | Rumen of Dairy Cow |
| NCIMB 41788 | | Rumen of Dairy Cow |
| NRRL 18624 | | Rumen of Bovine |
| NIAH 1102 | | N/A |

In some embodiments, the M. elsdenii cells are from a strain having a deposit number selected from the group consisting of: ATCC® 25940, ATCC® 17752, ATCC® 17753, NCIMB 702261, NCIMB 702262, NCIMB 702264, NCIMB 702331, NCIMB 702409, NCIMB 702410, NCIMB 41125, NCIMB 41787, NCIMB 41788, NRRL 18624, NIAH 1102, and combinations thereof, including any of the alternative designations in Table 1.

In some embodiments, the M. elsdenii cells are from a strain isolated from a ruminant (e.g., a cow). See, e.g., U.S. Pat. No. 7,550,139.

In some embodiments, the *M. elsdenii* cells are from a strain isolated from a non-ruminant (e.g., a human).

In some embodiments, the *M. elsdenii* cells are from a strain selected for lactate utilization (e.g., a strain that utilizes lactate in the presence of sugars), resistance to ionophore antibiotics, relatively high growth rate, capability to produce predominantly acetate, capability to proliferate at pH values below 5.0 and as low as 4.5, production of volatile fatty acids (VFAs), phytase activity, and combinations thereof. See, e.g., U.S. Pat. No. 7,550,139.

In some embodiments, a strain selected for lactate utilization utilizes lactate as a preferred carbon source in the presence of a soluble carbohydrate (e.g., glucose and/or maltose). Lactate utilization can be determined, for example, based on growth in a medium containing lactate and lacking soluble carbohydrates as compared to the same medium supplemented with soluble carbohydrates.

In some embodiments, the *M. elsdenii* cells are from a strain with a high growth rate as compared to other strains. The growth rates of different strains can be determined, for example, by culturing the cells in a liquid medium and monitoring the increase in optical density overtime.

In some embodiments, the *M. elsdenii* cells are from a strain capable of producing VFAs, which can be determined, for example, by gas chromatography. In some embodiments, the VFA is a 6-carbon fatty acid that is capable of inhibiting growth of *Salmonella* and/or *Campylobacter*. In some embodiments, the VFA is caproic acid. In some embodiments, the *Salmonella* is *Salmonella enterica* and/or *Salmonella bongori*. In some embodiments, the *Salmonella* serotype is *Salmonella Typhimurium* and/or *Enteritidis*. In some embodiments, the *Campylobacter* is *Campylobacter jejuni* or *Campylobacter coli*.

In some embodiments, the *M. elsdenii* cells are from a strain with phytase activity.

In some embodiments, the *M. elsdenii* cells are from *Megasphaera elsdenii* strain NCIMB 41125. This strain of *Megasphaera elsdenii* has a high specific growth rate (0.94 generations/hour), is capable of growth in a pH range of 4.5 to 6.5 or more, uses D- and L-Lactate as its preferred substrate, but also has the ability to utilize glucose and other carbohydrates, and tolerates ionophores.

In some embodiments, the *M. elsdenii* cells are from *Megasphaera elsdenii* strain NCIMB 41787. In some embodiments, the *M. elsdenii* cells are from *Megasphaera elsdenii* strain NCIMB 41788.

In some embodiments, the *M. elsdenii* cells are from *Megasphaera elsdenii* strain ATCC® 25940.

In some embodiments, the *M. elsdenii* cells are derived from a strain selected from a stock culture collection or isolated from a natural source. Cells that are "derived" from a strain can be a natural or artificial derivative such as, for example, a sub isolate, a mutant, variant, or recombinant strain.

Preparing a Culture Comprising Anaerobic, Aerobic, and/or Yeast Cells

*M. elsdenii* is an anaerobic bacterium that must be cultured under strict anaerobic conditions in order to obtain maximum yield and viability.

In some embodiments, a culture comprises *M. elsdenii* cells and a growth media.

In some embodiments, the culture comprises one or more strains of *M. elsdenii* cells. In some embodiments, the culture comprises a single strain of *M. elsdenii* cells. In some embodiments, the culture consists of one or more strains of *M. elsdenii* cells (i.e., the cells in the culture consist of *M. elsdenii* cells, e.g., one or more strains of *M. elsdenii* cells). In some embodiments, the culture consists of a single strain of *M. elsdenii* cells.

In some embodiments, a culture comprises *Megasphaera* cells and a growth media.

In some embodiments, a culture comprises anaerobic bacterial cells and a growth media. In some embodiments, the culture comprises *Bifidobacterium* cells, such as *B. breve*, *Lactobacillus* cells, such as *L. plantarum*, *Bifidobacterium* cells, such as *B. animalis* subsp. *lactis*, *Pediococcus* cells, such as *P. acidilactici*, *Lactobacillus* cells, such as *L. casei* and a growth media.

In some embodiments, a culture comprises aerobic bacterial cells and a growth media. In some embodiments, a culture comprises *Bacillus* cells, such as *B. subtilis* and a growth media.

In some embodiments, a culture comprises yeast cells and a growth media. In some embodiments, a culture comprises *Saccharomyces* cells, such as *S. boulardi* and *S. cerevisiae*.

Various fermentation parameters for inoculating, growing, and harvesting microbial cells can be used, including continuous fermentation (i.e., continuous culture) or batch fermentation (i.e., batch culture). See, for example, U.S. Pat. No. 7,550,139.

Growth media for microbial cells can be a solid, semi-solid, or liquid. A medium can contain nutrients that provide essential elements and specific factors that enable growth. A variety of microbiological media and variations are well known in the art. Media can be added to a culture at any time, including the start of the culture, during the culture, or intermittently/continuously.

Examples of growth media include, but are not limited to: (1) semi-defined media, which contains peptone, 3 g/L; yeast, 3 g/L; vitamin solution, 2 mL/L; mineral solution, 25 mL/L; indigo carmine (0.5%), 1 g/L; 12.5% L-cysteine, 2 g/L; 12.5% sodium sulfide, 2 g/L; and supplemented with either Na-lactate (semi-defined lactate, SDL), glucose (semi-defined glucose, SDG), or maltose (semi-defined maltose, SDM); (2) Modified Reinforced Clostridial Agar/Broth Medium (pre-reduced), which contains peptone, 10 g/L; beef extract, 10 g/L; yeast extract, 3 g/L; dextrose 5 g/L; NaCl, 5 g/L; soluble starch, 1 g/L; L-cysteine HCl, 0.5 g/L; sodium acetate, 3 g/L; and resazurin (0.025%), 4 mL/L; (3) Trypticase soy agar/broth with defibrinated sheep blood; (4) semi-defined rumen fluid free medium, which contains Na-lactate (70%), 10 g/l; Peptone, 2 g/l; $KH_2PO_4$ 1 g/l; $(NH_4)_2SO_4$ 3 g/l; $MgSO_4$ $7H_2O$ 0.2 g/l; $CaCl_2 \cdot 2H_2O$ 0.06 g/l; Vitamins (Pyridoxolhydrochloride, 4 mg/l; Pyridoxamine, 4 mg/l; Riboflavin, 4 mg/l; Thiaminiumchloride, 4 mg/l; Nicotinamide, 4 mg/l; Ca-D-pantothenate, 4 mg/l; 4-Aminobenzoic acid, 0.2 mg/l, Biotin, 0.2 mg/l, Folic acid, 0.1 mg/l and Cyanocobalamin, 0.02 mg/l); $Na_2S \cdot 9H_2O$, 0.25 g/l; Cysteine, 0.25 g/l; Antifoam, 0.07 ml/l and Monensin, 10 mg/l; and which is prepared by adding the Na-lactate and mineral solution to a reservoir boffle and autoclaving for 60 minutes; dissolving the peptone in 300 ml distilled $H_2O$ and autoclaving separately; filter sterilizing the vitamin solution and two reducing agents beforehand; following autoclaving, gassing the reservoir bottle with anaerobic gas overnight; adding the other constituents separately after cooling; and adjusting the pH to the desired value with 5N HCl; and (5) incubated rumen fluid lactate ("IRFL") medium, which contains 400 ml incubated clarified rumen fluid from lucerne-fed sheep, 371 ml distilled water, 2 g peptone, 15 g agar, 100 ml 10% (w/v) sodium-D, L-lactate solution, 100 ml 0.04% (w/v) bromocresol purple solution, and 25 ml mineral solution containing 40 g/l $KH_2PO_4$; 120 g/l $(NH_4)_2$ SO$_4$; 8 g/l MgSO$_4$·7H$_2$O and 2.4 g/l CaCl$_2$·2H$_2$O, where lactic acid (90% w/v) is used to adjust the pH to 5.5 before autoclaving at 121° C. for 25 minutes, then cooling in a 50° C. water bath while being gassed with an anaerobic gas mixture, followed by adding two milliliters of each of Na$_2$S·9H$_2$O (12.5% w/v) and cysteine·HCl·H$_2$O (12.5% w/v).

In some embodiments, the culture comprises a growth media comprising at least one carbon source. In some embodiments, the at least one carbon source are selected from the group consisting of: casein, starch (e.g., gelatinized starch and/or soluble starch), lactate (i.e., lactic acid), dextrose, fructose, fructan, glucose, sucrose, lactose, maltose, acetate, glycerol, mannitol, sorbitol, saccharose, xylose, molasses, fucose, glucosamine, dextran, a fat, an oil, glycerol, sodium acetate, arabinose, soy protein, soluble protein, raffinose, amylose, starch, tryptone, yeast extract and combinations there.

In some embodiments, the culture comprises a growth media comprising at least two carbon sources. In some embodiments, the at least two carbon sources are selected from the group consisting of: casein, starch (e.g., gelatinized starch and/or soluble starch), lactate (i.e., lactic acid), dextrose, fructose, fructan, glucose, sucrose, lactose, maltose, acetate, glycerol, mannitol, sorbitol, saccharose, xylose, molasses, fucose, glucosamine, dextran, a fat, an oil, glycerol, sodium acetate, arabinose, soy protein, soluble protein, raffinose, amylose, starch, tryptone, yeast extract and combinations there.

In some embodiments, the at least two carbon sources consist of about 1-99% of a first carbon source (e.g., any carbon source described herein) and about 1-99% of a second carbon source (e.g., any carbon source described herein that is different from the first carbon source), wherein 100% of the at least two carbon sources consist of the first carbon source and the second carbon source. In some embodiments, the at least two carbon sources consist of about 50-60% of the first carbon source and about 40-50% of the second carbon source, about 50-70% of the first carbon source and about 30-50% of the second carbon source, about 50-80% of the first carbon source and about 20-50% of the second carbon source, or about 50-90% of the first carbon source and about 10-50% of the second carbon source. In other embodiments, the at least two carbon sources consist of about 65-75% of the first carbon source and about 25-35% of the second carbon source. In some embodiments, the first carbon source is lactate.

In some embodiments, the M. elsdenii cells are grown at about 39° C. to about 40° C., at about 35° C., at about 36° C., at about 37° C., at about 38° C., at about 39° C., or at about 40° C.

In some embodiments, the microbial cells are grown at about 15° C. to about 45° C., at about 20° C. to about 40° C., 25° C. to 35° C., 30° C. to 39° C. In some embodiments, the microbial cells are grown at about 30° C., about 31° C., about 32° C., about 33° C., about 34° C., about 35° C., at about 36° C., at about 37° C., at about 38° C., at about 39° C., or at about 40° C.

In some embodiments, the microbial cells are cooled to about 18° C. to about 25° C. for storage.

In some embodiments, the pH of the culture comprising the M. elsdenii cells (e.g., during the culturing and/or at the time of harvesting) is between about 4.5 to about 7.0, between about 4.5 to about 6.5, between about 4.5 to about 6.0, between about 4.5 to about 5.5, between about 4.5 to about 5.0, between about 4.6 to about 6.9, between about 4.7 to about 6.8, between about 4.8 to about 6.7, between about 4.9 to about 6.6, between about 5.0 to about 7.0, between about 5.0 to about 6.5, between about 5.0 to about 6.0, between about 5.0 to about 5.5, between about 5.1 to about 6.9, between about 5.2 to about 6.8, between about 5.3 to about 6.7, between about 5.4 to about 6.6, between about 5.5 to about 7.0, between about 5.5 to about 6.5, between about 5.1 to about 6.4, between about 5.2 to about 6.3, between about 5.3 to about 6.2, between about 5.4 to about 6.1, between about 5.5 to about 6.0, between about 5.0 to about 6.1, between about 5.0 to about 6.2, between about 5.0 to about 6.3, between about 5.0 to about 6.4, between about 5.1 to about 6.5, between about 5.2 to about 6.5, between about 5.3 to about 6.5, or between about 5.4 to about 6.5.

In some embodiments, the pH of the culture comprising the microbial cells (e.g., during the culturing and/or at the time of harvesting) is between about 4.0 to about 9.0, between about 4.5 to about 8.5, between about 5.0 to about 8.0, between about 5.5 to about 7.5, between about 6.0 to about 7.0.

To culture microbial cells, fermenters of different sizes and designs that maintain anaerobic conditions can be used. A fermenter can be capable, for example, of fermenting culture volumes sufficient for commercial production of M. elsdenii cells. In some embodiments, the culture volume is about 2 liters, about 10 liters, about 50 liters, about 100 liters, about 150 liters, about 200 liters, about 250 liters, about 300 liters, about 350 liters, about 400 liters, about 450 liters, about 500 liters, about 600 liters, about 800 liters, about 1,000 liters, about 1,200 liters, about 1,500 liters, about 1,800 liters, about 2,000 liters, about 2, 200 liters, about 2,500 liters, about 2,750 liters, about 3,000 liters, about 4,000 liters, about 5,000 liters, about 6,000 liters, about 7,000 liters, about 8,000 liters, about 9,000 liters, about 10,000 liters, at least about 20,000 liters, at least about 50,000 liters, or at least about 75,000 liters. In some embodiments, the fermentation volume is about 2 liters to about 75,000 liters, about 250 liters to about 750 liters, about 300 liters to about 800 liters, about 350 liters to about 850 liters, about 400 liters to about 900 liters, about 450 liters to about 950 liters, about 500 liters to about 1,000 liters, about 750 liters to about 1,250 liters, about 1,000 liters to about 2,000 liters, about 2,000 liters to about 4,000 liters, about 4,000 liters to about 8,000 liters, about 5,000 liters to about 10,000 liters, about 50 liters to about 75,000 liters, about 50 liters to about 50,000 liters, about 50 liters to about 25,000 liters, about 50 liters to about 20,000 liters, about 50 liters to about 15,000 liters, about 50 liters to about 10,000 liters, about 100 liters to about 10,000 liters, about 100 liters to about 5,000 liters, about 100 liters to about 4,000 liters, about 100 liters to about 3,000 liters, about 100 liters to about 2,900 liters, about 100 liters to about 2,850 liters, about 100 liters to about 2,800 liters, about 100 liters to about 2,750 liters, about 2 liters, about 10 liters, about 50 liters, about 100 liters, about 200 liters, about 500 liters, about 1,000 liters, about 1,500 liters, about 10,000 liters, about 20,000 liters, about 50,000 liters, or about 75,000 liters.

In some embodiments, a culture comprising M. elsdenii cells also comprises another microorganism (i.e., a microbial cell that is not a M. elsdenii cell). In some embodiments, a culture comprises M. elsdenii cells and another microorganism that is an obligate anaerobe. In some embodiments, the culture comprises M. elsdenii cells and another microorganism selected from the group consisting of: Lactobacillus, Megasphaera, Bifidobacterium, Escherichia, Enterococcus, Bacillus, Propionibacterium, Streptococcus, Candida, Clostridium, Pediococcus, Aspergillus, and Saccharomyces.

Freeze-Dried Aerobic, Anaerobic, and Yeast Cells

In one aspect, the present invention is directed to a method of producing freeze-dried *Megasphaera elsdenii* cells.

In another aspect, the present invention is directed to freeze-dried *M. elsdenii* cells.

In another aspect, the present invention is directed to freeze-dried *M. elsdenii* cells produced by a method disclosed herein.

In another aspect, the present invention is directed to a method of producing freeze-dried *Megasphaera* cells.

In another aspect, the present invention is directed to freeze-dried *Megasphaera* cells.

In another aspect, the present invention is directed to freeze-dried *Megasphaera* cells produced by a method disclosed herein.

In another aspect, the present invention is directed to a method of producing freeze-dried anaerobic bacterial cells.

In another aspect, the present invention is directed a method of producing freeze-dried *Bifidobacterium* cells, such as *B. breve*, *Lactobacillus* cells, such as *L. plantarum*, *Bifidobacterium* cells, such as *B. animalis* subsp. *lactis*, *Pediococcus* cells, such as *P. acidilactici*, *Lactobacillus* cells, such as *L. casei*.

In another aspect, the present invention is directed to freeze-dried anaerobic bacterial cells.

In another aspect, the present invention is directed to freeze-dried *Bifidobacterium* cells, such as *B. breve*, *Lactobacillus* cells, such as *L. plantarum*, *Bifidobacterium* cells, such as *B. animalis* subsp. *lactis*, *Pediococcus* cells, such as *P. acidilactici*, *Lactobacillus* cells, such as *L. casei*.

In another aspect, the present invention is directed to freeze-dried anaerobic anaerobic bacteria produced by a method disclosed herein.

In another aspect, the present invention is directed to freeze-dried *Bifidobacterium* cells, such as *B. breve*, *Lactobacillus* cells, such as *L. plantarum*, *Bifidobacterium* cells, such as *B. animalis* subsp. *lactis*, *Pediococcus* cells, such as *P. acidilactici*, *Lactobacillus* cells, such as *L. casei* produced by a method disclosed herein.

In another aspect, the present invention is directed to a method of producing freeze-dried aerobic bacterial cells.

In another aspect, the present invention is directed a method of producing freeze-dried *Bacillus* cells, such as *B. subtilis*.

In another aspect, the present invention is directed to freeze-dried aerobic bacterial cells.

In another aspect, the present invention is directed to freeze-dried *Bacillus* cells, such as *B. subtilis*.

In another aspect, the present invention is directed to freeze-dried aerobic bacterial cells produced by a method disclosed herein.

In another aspect, the present invention is directed to freeze-dried *Bacillus* cells, such as *B. subtilis* produced by a method disclosed herein.

In another aspect, the present invention is directed to a method of producing freeze-dried yeast cells.

In another aspect, the present invention is directed a method of producing freeze-dried *Saccharomyces* cells, such as *S. boulardii* and *S. cerevisiae*.

In another aspect, the present invention is directed to freeze-dried yeast cells.

In another aspect, the present invention is directed to freeze-dried *Saccharomyces*, such as *S. boulardii* and *S. cerevisiae*.

In another aspect, the present invention is directed to freeze-dried yeast cells produced by a method disclosed herein.

In another aspect, the present invention is directed to freeze-dried *Saccharomyces* cells, such as *S. boulardii* and *S. cerevisiae* produced by a method disclosed herein.

In another aspect, a method of producing freeze-dried *M. elsdenii* cells comprises: preparing a culture comprising *M. elsdenii* cells and a growth media; harvesting the cells; freezing the cells; and freeze-drying the cells, wherein freeze-dried *M. elsdenii* cells are produced. In some embodiments, the method is performed in the order of preparing the culture, then harvesting the cells (i.e., harvesting the cultured cells), then freezing the cells (i.e., freezing the harvested cells), and then freeze-drying the cells (i.e., freeze-drying the frozen cells).

In some embodiments, the method is performed under anaerobic conditions. In some embodiments, the method comprises preparing the culture, harvesting the cells, freezing the cells, freeze-drying the cells, or combinations thereof under anaerobic conditions.

The method can comprise any of the methods of preparing a culture as described herein. A culture of the method also can comprise any of the properties of a culture described herein.

In some embodiments, the cells in the culture comprise *M. elsdenii* cells. In some embodiments, the cells in the culture consist of *M. elsdenii* cells.

In some embodiments, the growth media comprises at least two carbon sources selected from the group consisting of: casein, lactate (i.e., lactic acid), dextrose, fructose, fructan, glucose, sucrose, lactose, maltose, acetate, glycerol, mannitol, saccharose, xylose, molasses, fucose, glucosamine, dextran, a fat, an oil, glycerol, sodium acetate, arabinose, soy protein, soluble protein, raffinose, amylose, starch, and combinations thereof.

In some embodiments, the method comprises harvesting the cells within 12 hours after the culture has ended its exponential growth phase and before the culture has begun its stationary growth phase. The culture can be cooled to room temperature to stop growth at the time of harvesting.

In some embodiments, the culture comprises a liquid, and the method comprises harvesting the *M. elsdenii* cells (e.g., concentrated *M. elsdenii* cells) with a percentage of the liquid. In some embodiments, the method comprises harvesting the cells with about 1% to about 40%, about 1% to about 35%, about 1% to about 30%, about 1% to about 25%, about 1% to about 20%, about 1% to about 15%, about 1% to about 10%, about 1% to about 5%, about 10%, about 9%, about 8%, about 7%, about 6%, about 5%, about 4%, about 3%, about 2%, or about 1% of the liquid. In some embodiments, the method comprises harvesting the cells with less that about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1% of the liquid.

In some embodiments, the culture comprises a liquid, and the method comprises harvesting the *M. elsdenii* cells (e.g., concentrated *M. elsdenii* cells) by removing a percentage of the liquid. In some embodiments, harvesting the cells comprises removing about 50% to about 100% of the liquid, about 55% to about 100%, about 60% to about 100%, about 65% to about 100%, about 70% to about 100%, about 75% to about 100%, about 80% to about 100%, about 85% to about 100%, about 90% to about 100%, or about 95% to about 100% of the liquid. In some embodiments, harvesting the cells comprises removing at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% of the liquid.

In some embodiments, the method comprises harvesting the *M. elsdenii* cells by concentrating the cells. In some embodiments, harvesting the cells comprises concentrating the cells by at least one technique selected from the group consisting of: centrifugation, filtration, dialysis, reverse osmosis, and combinations thereof. In some embodiments, the filtration comprises clay filtration. In some embodiments, the filtration comprises tangential flow filtration, also known as cross-flow filtration.

In some embodiments, the pH of the culture comprising the *M. elsdenii* cells at the time of harvesting is between about 4.5 to about 7.0, between about 4.5 to about 6.5, between about 4.5 to about 6.0, between about 4.5 to about 5.5, between about 4.5 to about 5.0, between about 4.6 to about 6.9, between about 4.7 to about 6.8, between about 4.8 to about 6.7, between about 4.9 to about 6.6, between about 5.0 to about 7.0, between about 5.0 to about 6.5, between about 5.0 to about 6.0, between about 5.0 to about 5.5, between about 5.1 to about 6.9, between about 5.2 to about 6.8, between about 5.3 to about 6.7, between about 5.4 to about 6.6, between about 5.5 to about 7.0, between about 5.5 to about 6.5, between about 5.1 to about 6.4, between about 5.2 to about 6.3, between about 5.3 to about 6.2, between about 5.4 to about 6.1, between about 5.5 to about 6.0, between about 5.0 to about 6.1, between about 5.0 to about 6.2, between about 5.0 to about 6.3, between about 5.0 to about 6.4, between about 5.1 to about 6.5, between about 5.2 to about 6.5, between about 5.3 to about 6.5, or between about 5.4 to about 6.5.

In some embodiments, the method comprises inoculating growth media in a fermenter with an inoculum comprising *M. elsdenii* cells to prepare a culture, and incubating the culture at a temperature of about 39° C. until the pH of the culture is about 6.0. In some embodiments, the inoculum comprising *M. elsdenii* cells is a flask culture of *M. elsdenii* cells or a portion thereof. In some embodiments, the method comprises inoculating growth media in a fermenter an inoculum to media ratio of 1/50 to 1/4,000. In some embodiments, the inoculum to media ration is 1/100.

In some embodiments, the culture further comprises at least one cryoprotectant. In some embodiments, the at least one cryoprotectant is selected from the group consisting of: fructose, glucose, sucrose, milk powder, infant formula, skim milk, trehalose, maltodextrin, betaine, and combinations thereof. In some embodiments, the at least one cryoprotectant is present in an amount of about 1% to about 50% (w/v) of the culture, about 1% to about 40% (w/v) of the culture, about 1% to about 30% (w/v) of the culture, about 1% to about 20% (w/v) of the culture, about 1% to about 10% (w/v) of the culture, about 1% to about 5% (w/v) of the culture, about 10% to about 20% (w/v) of the culture, about 15% to about 25% (w/v) of the culture, about 20% to about 30% (w/v) of the culture, about 30% to about 40% (w/v) of the culture, about 40% to about 50% (w/v) of the culture, about 60% to about 70% (w/v) of the culture, about 70% to about 80% (w/v) of the culture. In some embodiments, the cryoprotectant is added by adding powdered cryoprotectant directly to the concentrated *M. elsdenii* cells. In some embodiments, the cryoprotectant is added by adding a solution of cryoprotectant directly to the concentrated *M. elsdenii* cells at a ratio of 1/1, at a ratio of 1/5, or at a ratio of 1/10.

In some embodiments, freezing the cells comprises placing the cells in a freezer or contacting the cells with dry ice, liquid nitrogen, or a combination thereof. Freezing the cells includes freezing the cells while they are inside a container. Contacting the cells includes contacting a container comprising the cells with a medium for freezing the cells. A medium for freezing the cells includes, but is not limited to, a freezer, an acetone-dry ice bath, liquid nitrogen, or a combination thereof.

In some embodiments, the method comprises freezing the cells at a temperature of about −20° C. to about −210° C. In some embodiments, the method comprises freezing the cells at a temperature of about −20° C. to about −80° C. In some embodiments, the method comprises freezing the cells at a temperature of about −80° C. to about −210° C. In some embodiments, the method comprises freezing the cells at a temperature of about −20° C. to about −196° C. In some embodiments, the method comprises freezing the cells at a temperature of about −80° C. to about −196° C. In some embodiments, the method comprises freezing the cells at a temperature of about −20° C. In some embodiments, the method comprises freezing the cells at a temperature of about −80° C. In some embodiments, the method comprises freezing the cells at a temperature of about −196° C. In some embodiments, the method comprises freezing the cells by contacting the cells with liquid nitrogen.

In some embodiments, the method comprises freezing the cells under anaerobic conditions.

In some embodiments, the freezing produces frozen pellets comprising the cells. For example, the freezing can be achieved using a flash freezer (e.g., Model 250-S01 Crygran, IFQ Inc.).

In some embodiments, the diameter of the frozen pellets is about 0.001 to about 1.0 inches, about 0.01 to about 1.0 inches, about 0.1 to about 1.0 inches, about 0.2 to about 1.0 inches, about 0.3 to about 1.0 inches, about 0.4 to about 1.0 inches, about 0.5 to about 1.0 inches, about 0.6 to about 1.0 inches, about 0.7 to about 1.0 inches, about 0.8 to about 1.0 inches, about 0.9 to about 1.0 inches, about 0.001 to about 0.9 inches, about 0.01 to about 0.9 inches, about 0.1 to about 0.9 inches, about 0.2 to about 0.9 inches, about 0.3 to about 0.9 inches, about 0.4 to about 0.9 inches, about 0.5 to about 0.9 inches, about 0.6 to about 0.9 inches, about 0.7 to about 0.9 inches, about 0.8 to about 0.9 inches, about 0.001 to about 0.8 inches, about 0.01 to about 0.8 inches, about 0.1 to about 0.8 inches, about 0.2 to about 0.8 inches, about 0.3 to about 0.8 inches, about 0.4 to about 0.8 inches, about 0.5 to about 0.8 inches, about 0.6 to about 0.8 inches, about 0.7 to about 0.8 inches, about 0.001 to about 0.7 inches, about 0.01 to about 0.7 inches, about 0.1 to about 0.7 inches, about 0.2 to about 0.7 inches, about 0.3 to about 0.7 inches, about 0.4 to about 0.7 inches, about 0.5 to about 0.7 inches, about 0.6 to about 0.7 inches, about 0.001 to about 0.6 inches, about 0.01 to about 0.6 inches, about 0.1 to about 0.6 inches, about 0.2 to about 0.6 inches, about 0.3 to about 0.6 inches, about 0.4 to about 0.6 inches, about 0.5 to about 0.6 inches, about 0.001 to about 0.5 inches, about 0.01 to about 0.5 inches, about 0.05 to about 0.5 inches, about 0.1 to about 0.5 inches, about 0.15 to about 0.5 inches, about 0.2 to about 0.5 inches, about 0.3 to about 0.5 inches, or about 0.4 to about 0.5 inches.

The frozen *M. elsdenii* cells can be stored frozen (e.g., below 0° C.) before freeze-drying or can be immediately freeze-dried. In some embodiments, the frozen *M. elsdenii* cells are stored at a temperature below about 0° C., below about −10° C., below about −20° C., below about −50° C., below about −80° C., or below about −196° C. In some embodiments, the frozen *M. elsdenii* cells are stored at a temperature of about −20° C., about −30° C., about −40° C., about −50° C., about −60° C., about −70° C., about −80° C., about −90° C., about −100° C., about −150° C., about −196° C., or about −210° C.

In some embodiments, the frozen *M. elsdenii* cells are lyophilized. In some embodiments, the frozen *M. elsdenii* cells are freeze-dried. Freeze-drying involves, for example, the removal of liquid from frozen cells.

In some embodiments, freeze-drying the *M. elsdenii* cells comprises placing the frozen cells into a freeze-drier. In some embodiments, the freeze-drying comprises subjecting the frozen cells to reduced pressure, and gradually warming the cells to room temperature.

In some embodiments, the method comprises freeze-drying the cells under anaerobic conditions.

In some embodiments, the freeze-dried *M. elsdenii* is produced on a commercial scale.

In some embodiments, about $1 \times 10^3$ to $1 \times 10^{12}$ CFU/g of freeze-dried *M. elsdenii* cells are produced by a method disclosed herein. In some embodiments, about $1 \times 10^3$ to $1 \times 10^{12}$ CFU/g of *M. elsdenii* cells are viable after freeze-drying.

In one aspect, a method of producing freeze-dried *Megasphaera elsdenii* cells according to the present disclosure comprises: (a) preparing a culture under anaerobic conditions comprising *M. elsdenii* cells and a growth media comprising at least two carbon sources selected from the group consisting of: casein, lactate (i.e., lactic acid), dextrose, fructose, fructan, glucose, sucrose, lactose, maltose, acetate, glycerol, mannitol, sorbitol, saccharose, xylose, molasses, fucose, glucosamine, dextran, a fat, an oil, glycerol, sodium acetate, arabinose, soy protein, soluble protein, raffinose, amylose, starch, tryptone, yeast extract and combinations thereof, (b) harvesting the cells under anaerobic conditions, (c) freezing the cells, and (d) freeze-drying the cells, wherein about $1 \times 10^3$ to about $1 \times 10^{12}$ CFU/g of freeze-dried *M. elsdenii* cells are produced.

In another aspect, a method of producing freeze-dried *Megasphaera elsdenii* cells according to the present disclosure comprises: (a) preparing a culture comprising *M. elsdenii* cells and a growth media, (b) harvesting the cells under anaerobic conditions within 12 hours after the culture has ended its exponential growth phase and before the culture has begun its stationary growth phase, (c) freezing the cells, and (d) freeze-drying the cells, wherein freeze-dried *M. elsdenii* cells are produced.

In another aspect, a method of producing freeze-dried *Megasphaera elsdenii* cells according to the present disclosure comprises: (a) preparing a culture comprising *M. elsdenii* cells and a growth media, (b) harvesting the cells, (c) freezing the cells at a temperature of about −80° C. to about −210° C. within 5 hours of harvesting, and (d) freeze-drying the cells, wherein freeze-dried *M. elsdenii* cells are produced.

In some embodiments, the amount of freeze-dried *M. elsdenii* cells produced by a method disclosed herein and/or the amount of *M. elsdenii* cells that are viable after freeze-drying is about $1 \times 10^3$ CFU/g to about $1 \times 10^{12}$ CFU/g about $1 \times 10^3$ CFU/g to about $1 \times 10^{11}$ CFU/g, about $1 \times 10^3$ CFU/g to about $1 \times 10^{10}$ CFU/g, about $1 \times 10^3$ CFU/g to about $1 \times 10^9$ CFU/g, about $1 \times 10^3$ CFU/g to about $1 \times 10^8$ CFU/g, about $1 \times 10^3$ CFU/g to about $1 \times 10^7$ CFU/g, about $1 \times 10^3$ CFU/g to about $1 \times 10^6$ CFU/g, about $1 \times 10^3$ CFU/g to about $1 \times 10^5$ CFU/g, about $1 \times 10^4$ CFU/g to about $1 \times 10^{12}$ CFU/g, about $1 \times 10^5$ CFU/g to about $1 \times 10^{12}$ CFU/g, about $1 \times 10^6$ CFU/g to about $1 \times 10^{12}$ CFU/g, about $1 \times 10^7$ CFU/g to about $1 \times 10^{12}$ CFU/g, about $1 \times 10^8$ CFU/g to about $1 \times 10^{12}$ CFU/g, about $1 \times 10^9$ CFU/g to about $1 \times 10^{12}$ CFU/g, about $1 \times 10^{10}$ CFU/g to about $1 \times 10^{12}$ CFU/g, about $1 \times 10^3$ CFU/g to about $1 \times 10^5$ CFU/g, about $1 \times 10^4$ CFU/g to about $1 \times 10^6$ CFU/g, about $1 \times 10^5$ CFU/g to about $1 \times 10^7$ CFU/g, about $1 \times 10^6$ CFU/g to about $1 \times 10^8$ CFU/g, about $1 \times 10^7$ CFU/g to about $1 \times 10^9$ CFU/g, about $1 \times 10^8$ CFU/g to about $1 \times 10^{10}$ CFU/g, about $1 \times 10^9$ CFU/g to about $1 \times 10^{11}$ CFU/g, or about $1 \times 10^{10}$ CFU/g to about $1 \times 10^{12}$ CFU/g.

In some embodiments, the freeze-dried *M. elsdenii* cells are viable for about 14 days to about 24 months at about −80° C., about −20° C., about 4° C., about 25° C., or combinations thereof. In some embodiments, the freeze-dried *M. elsdenii* cells are viable for at least about 14 days, at least about 1 month, at least about 6 months, at least about 8 months, at least about 10 months, at least about 12 months, at least about 15 months, at least about 18 months, or at least about 24 months at about −80° C., about −20° C., about 4° C., about 25° C., or combinations thereof.

In some embodiments, about $1 \times 10^3$ CFU/g to about $1 \times 10^{12}$ CFU/g about $1 \times 10^3$ CFU/g to about $1 \times 10^{11}$ CFU/g, about $1 \times 10^3$ CFU/mL to about $1 \times 10^{10}$ CFU/g, about $1 \times 10^3$ CFU/g to about $1 \times 10^9$ CFU/g, about $1 \times 10^3$ CFU/g to about $1 \times 10^8$ CFU/g, about $1 \times 10^3$ CFU/g to about $1 \times 10^7$ CFU/g, about $1 \times 10^3$ CFU/g to about $1 \times 10^6$ CFU/g, about $1 \times 10^3$ CFU/g to about $1 \times 10^5$ CFU/g, about $1 \times 10^4$ CFU/g to about $1 \times 10^{12}$ CFU/g, about $1 \times 10^5$ CFU/g to about $1 \times 10^{12}$ CFU/g, about $1 \times 10^6$ CFU/g to about $1 \times 10^{12}$ CFU/g, about $1 \times 10^7$ CFU/g to about $1 \times 10^{12}$ CFU/g, about $1 \times 10^8$ CFU/g to about $1 \times 10^{12}$ CFU/g, about $1 \times 10^9$ CFU/g to about $1 \times 10^{12}$ CFU/g, about $1 \times 10^{10}$ CFU/g to about $1 \times 10^{12}$ CFU/g, about $1 \times 10^3$ CFU/g to about $1 \times 10^5$ CFU/g, about $1 \times 10^4$ CFU/g to about $1 \times 10^6$ CFU/g, about $1 \times 10^5$ CFU/g to about $1 \times 10^7$ CFU/g, about $1 \times 10^6$ CFU/g to about $1 \times 10^8$ CFU/g, about $1 \times 10^7$ CFU/g to about $1 \times 10^9$ CFU/g, about $1 \times 10^8$ CFU/g to about $1 \times 10^{10}$ CFU/g, about $1 \times 10^9$ CFU/g to about $1 \times 10^{11}$ CFU/g, or about $1 \times 10^{10}$ CFU/g to about $1 \times 10^{12}$ CFU/g of freeze-dried *M. elsdenii* cells are viable after storage at a temperature of about −80° C., about −20° C., about 4° C., or combinations thereof for at least about 14 days, at least about 1 month, at least about 6 months, at least about 8 months, at least about 10 months, at least about 12 months, at least about 15 months, at least about 18 months, or at least about 24 months.

In some embodiments, about $1 \times 10^3$ CFU/g to about $1 \times 10^{12}$ CFU/g about $1 \times 10^3$ CFU/g to about $1 \times 10^{11}$ CFU/g, about $1 \times 10^3$ CFU/g to about $1 \times 10^{10}$ CFU/g, about $1 \times 10^3$ CFU/g to about $1 \times 10^9$ CFU/g, about $1 \times 10^3$ CFU/g to about $1 \times 10^8$ CFU/g, about $1 \times 10^3$ CFU/g to about $1 \times 10^7$ CFU/g, about $1 \times 10^3$ CFU/g to about $1 \times 10^6$ CFU/g, about $1 \times 10^3$ CFU/g to about $1 \times 10^5$ CFU/g, about $1 \times 10^4$ CFU/g to about $1 \times 10^{12}$ CFU/g, about $1 \times 10^5$ CFU/g to about $1 \times 10^{12}$ CFU/g, about $1 \times 10^6$ CFU/g to about $1 \times 10^{12}$ CFU/g, about $1 \times 10^7$ CFU/g to about $1 \times 10^{12}$ CFU/g, about $1 \times 10^8$ CFU/g to about $1 \times 10^{12}$ CFU/g, about $1 \times 10^9$ CFU/g to about $1 \times 10^{12}$ CFU/g, about $1 \times 10^{10}$ CFU/g to about $1 \times 10^{12}$ CFU/g, about $1 \times 10^3$ CFU/g to about $1 \times 10^5$ CFU/g, about $1 \times 10^4$ CFU/g to about $1 \times 10^6$ CFU/g, about $1 \times 10^5$ CFU/g to about $1 \times 10^7$ CFU/g, about $1 \times 10^6$ CFU/g to about $1 \times 10^8$ CFU/g, about $1 \times 10^7$ CFU/g to about $1 \times 10^9$ CFU/g, about $1 \times 10^8$ CFU/g to about $1 \times 10^{10}$ CFU/g, about $1 \times 10^9$ CFU/g to about $1 \times 10^{11}$ CFU/g, or about $1 \times 10^{10}$ CFU/g to about $1 \times 10^{12}$ CFU/g of freeze-dried *M. elsdenii* cells are viable after storage at a temperature of about 25° C. for at least about 14 days, at least about 1 month, at least about 6 months, at least about 8 months, at least about 10 months, at least about 12 months, at least about 15 months, at least about 18 months, or at least about 24 months.

Feed Additives, Compositions, and Kits

In one aspect, a feed additive comprises *M. elsdenii* cells as disclosed herein.

In some embodiments, the feed additive comprises freeze-dried *M. elsdenii* cells as disclosed herein. In some embodiments, the feed additive comprises freeze-dried *M. elsdenii* cells produced by a method disclosed herein.

In one aspect, a feed additive comprises *Megasphaera* cells as disclosed herein.

In some embodiments, the feed additive comprises freeze-dried *Megasphaera* cells as disclosed herein. In some embodiments, the feed additive comprises freeze-dried *Megasphaera* cells produced by a method disclosed herein.

In one aspect, a feed additive comprises anaerobic bacterial cells as disclosed herein. In another aspect, a feed additive comprises *Bifidobacterium* cells, such as *B. breve, Lactobacillus* cells, such as *L. plantarum, Bifidobacterium* cells, such as *B. animalis* subsp. *lactis, Pediococcus* cells, such as *P. acidilactici, Lactobacillus* cells, such as *L. casei.*

In some embodiments, the feed additive comprises freeze-dried anaerobic bacterial cells as disclosed herein. In some embodiments, the feed additive comprises freeze-dried anaerobic bacterial cells produced by a method disclosed herein.

In some embodiments, the feed additive comprises freeze-dried *Bifidobacterium* cells, such as *B. breve, Lactobacillus* cells, such as *L. plantarum, Bifidobacterium* cells, such as *B. animalis* subsp. *lactis, Pediococcus* cells, such as *P. acidilactici, Lactobacillus* cells, such as *L. casei.* In some embodiments, the feed additive comprises freeze-dried *Bifidobacterium* cells, such as *B. breve, Lactobacillus* cells, such as *L. plantarum, Bifidobacterium* cells, such as *B. animalis* subsp. *lactis, Pediococcus* cells, such as *P. acidilactici, Lactobacillus* cells, such as *L. casei* produced by a method disclosed herein.

In one aspect, a feed additive comprises aerobic bacterial cells as disclosed herein. In another aspect, a feed additive comprises *Bacillus* cells, such as *B. subtilis.*

In some embodiments, the feed additive comprises freeze-dried aerobic bacterial cells as disclosed herein. In some embodiments, the feed additive comprises freeze-dried aerobic bacterial cells produced by a method disclosed herein.

In some embodiments, the feed additive comprises freeze-dried *Bacillus* cells, such as *B. subtilis.* In some embodiments, the feed additive comprises freeze-dried *Bacillus* cells, such as *B. subtilis* produced by a method disclosed herein.

In one aspect, a feed additive comprises yeast cells as disclosed herein. In another aspect, a feed additive comprises *Saccharomyces* cells, such as *S. boulardii* and *S. cerevisiae.*

In some embodiments, the feed additive comprises freeze-dried yeast cells as disclosed herein. In some embodiments, the feed additive comprises freeze-dried yeast cells produced by a method disclosed herein.

In some embodiments, the feed additive comprises freeze-dried *Saccharomyces* cells, such as *S. boulardii* and *S. cerevisiae.* In some embodiments, the feed additive comprises freeze-dried *Saccharomyces* cells, such as *S. boulardii* and *S. cerevisiae* produced by a method disclosed herein.

In some embodiments, the feed additive is a solid (i.e., "a solid feed additive") or a liquid (i.e., "a liquid feed additive"). In some embodiments, the feed additive is a semi-solid or a gel (i.e., "a semi-solid or a gel feed additive"). A gel feed additive can contain an oxygen scavenger (e.g., ascorbic acid).

In some embodiments, a solid feed additive is a powder (e.g., a flowable powder), granule (i.e., a granulate), particle (i.e., particulate), pellet, cake, water soluble concentrate, paste, bolus, tablet, dust, a component thereof, or combinations thereof.

In some embodiments, a liquid feed additive is a solution (e.g., an aqueous, organic, or aqueous-organic solution), suspension, emulsion, drench, spray, injectable, drink (e.g., a milk replacer), a component thereof, or combinations thereof.

In some embodiments, a gel feed additive is an organogel. In some embodiments, the gel feed additive is an oral gel (i.e., a gel for oral administration).

In some embodiments, the feed additive is for use as a top dress (i.e., for adding to the surface of a food or mixing with a food (e.g., an animal feed)). In some embodiments, the feed additive is for administration as a liquid.

In some embodiments, freeze-dried *M. elsdenii* cells as disclosed herein can be used as a liquid feed additive by rehydrating, dissolving, solubilizing, and/or suspending the freeze-dried cells in a liquid.

In some embodiments, the feed additive comprises a carrier (i.e., one or more carriers).

Examples of suitable carriers include, but are not limited to, plant materials (i.e., whole plants or plant parts (e.g., seeds, stems, leaves, flowers, and/or roots, for example), including dried or processed plants or plant parts), dried grains (e.g., distillers' dried grains), alfalfa, corn meal, citrus meal, fermentation residues, ground oyster shells, attapulgus clay, wheat shorts, molasses solubles, corn cob meal, edible vegetable substances, toasted dehulled soya flour, soybean mill feed, antibiotic mycelis, vermiculite, soya grits, whey, maltodextrin, sucrose, dextrose, limestone (calcium carbonate), rice hulls, yeast culture, dried starch, sodium silica aluminate, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like, and combinations thereof.

In some embodiments, the feed additive comprises an excipient (i.e., one or more excipients) including, but not limited to, microcrystalline cellulose; lactose; sodium citrate; calcium carbonate; dibasic calcium phosphate and glycine; disintegrants such as starch, sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin, and acacia; bulking agents such as maltodextrin; moisture scavengers such as silicon dioxide; oxygen scavengers such as ascorbic acid; and/or lubricating agents such as magnesium stearate, stearic acid, glyceryl behenate, and talc.

In some embodiments, the feed additive is a granule comprising: a core comprising the *M. elsdenii* cells and/or feed additive, and a coating over the core. In some embodiments, the coating is a hydrated barrier salt. The salt coating can provide improved thermo-tolerance, improved storage stability, and protection against other components in the granules that may otherwise have adverse effect (e.g., on stability) of the *M. elsdenii* cells and/or feed additive.

In some embodiments, the freeze-dried *M. elsdenii* is admixed with a dry formulation of additives including, but not limited to, growth substrates, enzymes, sugars, carbohydrates, extracts, and growth promoting micro-ingredients. The sugars can include, but are not limited to, lactose, maltose, dextrose, maltodextrin, glucose, fructose, mannose, tagatose, sorbose, raffinose, amylose, starch, and galactose. The sugars can range from 50-95%, either individually or in combination. The extracts can include, but are not limited to, yeast or dried yeast fermentation solubles ranging from 5-50%. The growth substrates can include, but are not limited to, trypticase, ranging from 5-25%; sodium lactate, ranging from 5-30%; and Tween 80, ranging from 1-5%. The carbohydrates can include, but are not limited to, mannitol, sorbitol, adonitol and arabitol. The carbohydrates can range from 5-50% individually or in combination. The micro-ingredients can include, but are not limited to, calcium carbonate, ranging from 0.5-5.0%; calcium chloride, ranging from 0.5-5.0%; dipotassium phosphate, ranging from 0.5-5.0%; calcium phosphate, ranging from 0.5-5.0%; manganese proteinate, ranging from 0.25-1.00%; and manganese, ranging from 0.25-1.00%.

In some embodiments, an *M. elsdenii* feed additive is prepared by mixing (e.g., with a mixer) *M. elsdenii* cells, including a culture comprising the cells and/or freeze-dried cells, with any additional components of the feed additive (e.g., a carrier and/or an excipient). In some embodiments, the components are mixed to obtain a uniform mixture.

In some embodiments, the feed additive is a top-dress animal feed additive comprising *M. elsdenii* cells as disclosed herein (e.g., freeze-dried cells) and a carrier. In some embodiments, the carrier is selected from the group consisting of: whey, maltodextrin, sucrose, dextrose, limestone (i.e., calcium carbonate), rice hulls, yeast culture, dried starch, and sodium silica aluminate, milk, water, and combinations thereof.

In some embodiments, the animal feed additive is a drench, spray, or supplement of a milk replacer comprising *M. elsdenii* cells as disclosed herein (e.g., freeze-dried cells) and a water soluble carrier. In some embodiments, the carrier is selected from the group consisting of: whey, maltodextrin, sucrose, dextrose, dried starch, sodium silica aluminate, milk, water, and combinations thereof.

In one aspect, the present invention is directed to a food (e.g., an animal feed) comprising *M. elsdenii* cells (e.g., freeze-dried cells as disclosed herein, e.g., freeze-dried cells produced by a method as disclosed herein) and/or a feed additive as disclosed herein. A food product is any food for animal consumption (i.e., non-human animals or humans), and includes both solid and liquid compositions. Foods include, but are not limited to, common foods; liquid products, including waters, milks, beverages, therapeutic drinks, and nutritional drinks; functional foods; supplements; nutraceuticals; infant (i.e., including non-human and human infants) formulas, including formulas for pre-mature infants; foods for pregnant or nursing animals; foods for adult animals; and geriatric foods. In some embodiments, the food includes a liquid (e.g., a drink, e.g., water, milk, or a milk replacer) comprising the feed additive.

In another aspect, the present invention is directed to a composition comprising *M. elsdenii* cells (e.g., freeze-dried cells) and/or a feed additive as disclosed herein. In some embodiments, the composition comprises freeze-dried *M. elsdenii* cells produced by a method disclosed herein.

In some embodiments, the *M. elsdenii* cells (e.g., freeze-dried cells) and/or a feed additive as disclosed herein can be further chemically or physically modified or processed based on the requirements of the composition by any known technique.

A composition of the invention can include one or more excipients. In some embodiments, the excipient can be, but is not limited to, an alkaline agent, a stabilizer, an antioxidant, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, *Remington: The Science and Practice of Pharmacy*, $21^{st}$ ed. (2005). Inclusion of an excipient in a particular classification herein (e.g., "solvent") is intended to illustrate rather than limit the role of the excipient. A particular excipient can fall within multiple classifications.

In some embodiments, the composition is a pharmaceutical composition (e.g., for treatment of non-human animals or humans). In some embodiments, the composition is a medical food (e.g., a veterinary food). A medical food includes a food that is in a composition to be consumed or administered externally under the supervision of a doctor (e.g., a veterinarian) and that is intended for the specific dietary management of a condition, for which distinctive nutritional requirements, based on recognized scientific principles, are established by medical evaluation. In some embodiments, the pharmaceutical composition comprises a pharmaceutically acceptable excipient. In some embodiments, the term "pharmaceutically acceptable" means approved by a regulatory agency of the Federal or a state government or listed in the U.S. Pharmacopeia or other generally recognized international pharmacopeia for use in animals, and more particularly in humans.

For oral administration of a composition, the *M. elsdenii* cells (e.g., freeze-dried cells) or feed additive can be combined with excipients well known in the art. Such carriers can, for example, allow the *M. elsdenii* cells or feed additive of the invention to be formulated as tablets, pills, dragees, capsules, liquids, gels, syrups, slurries, suspensions and the like, for oral ingestion by a subject to be treated. In some embodiments, the composition is a tablet, pill, caplet, or capsule. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl cellulose, sodium carboxymethyl cellulose, and polyvinylpyrrolidone (PVP). If desired, disintegrating agents can be added, such as, but not limited to, the cross-linked polyvinylpyrrolidone, agar, or alginic acid or a salt thereof such as sodium alginate. Compositions that can be used orally include, but are not limited to, capsules made of gelatin, as well as soft, sealed capsules made of gelatin and a plasticizer, such as glycerol or sorbitol. In some embodiments, the dosage form is a vegetarian dosage form, in which the dosage form is not formed from and does not contain any components from an animal source. In some embodiments, the vegetarian dosage form is a vegetarian capsule.

In one aspect, the present invention is directed to a capsule comprising *M. elsdenii* cells (e.g., freeze-dried cells) and/or a feed additive as disclosed herein. In some embodiments, the capsule is a gelatin capsule. In some embodiments, the capsule comprises freeze-dried *M. elsdenii* cells produced by a method as disclosed herein or a feed additive as disclosed herein. In some embodiments, the capsule is degradable. In some embodiments, the capsule is a degradable gelatin capsule.

In another aspect, the present invention is directed to an encapsulated freeze-dried composition comprising anaerobic bacterial cells, wherein the freeze-dried powder is encapsulated by dispensing the freeze-dried powder into heated oil. In another aspect, the present invention is directed to an encapsulated freeze-dried composition comprising *M. elsdenii* cells, wherein the freeze-dried powder is encapsulated by dispensing the freeze-dried powder into heated oil.

In another aspect, the present invention is directed to kits or packages comprising *M. elsdenii* cells, feed additives, foods, and/or compositions as disclosed herein. Kits or packages can include units of a feed additive, food, composition, or combinations thereof (e.g., one or more units). In some embodiments, the kit comprises freeze-dried cells produced by a method disclosed herein, a feed additive as disclosed herein, or a capsule as disclosed herein.

Methods of Administering Anaerobic Bacterial Cells, Aerobic Bacterial Cells and/or Yeast Cells to Animals In one aspect, the present invention is directed to a method of administering *M. elsdenii* cells to an animal.

In one aspect, the present invention is directed to a method of administering *Megasphaera* cells to an animal.

In one aspect, the present invention is directed to a method of administering anaerobic bacterial cells to an animal. In another aspect, the present invention is directed to a method of administering *Bifidobacterium* cells, such as *B. breve*, *Lactobacillus* cells, such as *L. plantarum*, *Bifidobacterium* cells, such as *B. animalis* subsp. *lactis*, *Pediococcus* cells, such as *P. acidilactici*, *Lactobacillus* cells, such as *L. casei* cells to an animal.

In one aspect, the present invention is directed to a method of administering aerobic bacterial cells to an animal. In another aspect, the present invention is directed to a method of administering *Bacillus* cells, such as *B. subtilis* cells to an animal.

In one aspect, the present invention is directed to a method of administering yeast cells to an animal. In another aspect, the present invention is directed to a method of administering *Saccharomyces* cells, such as *S. boulardii* and *S. cerevisiae* cells to an animal.

In some embodiments, the method comprises administering to the animal *M. elsdenii* cells, a feed additive, a food, or a composition (e.g., a capsule) as described herein.

The administration can be by any compatible route, including, for example, orally (i.e., an ingestible liquid or solid, an oral drench, a feed additive, a food, a composition, or a capsule), by spraying onto the body (i.e., by mist spraying), and/or injection.

In some embodiments, the method comprises administering a solid, a liquid, or a gel comprising the *M. elsdenii* cells.

In some embodiments, the method comprises administering a solid feed additive comprising the cells. In some embodiments, the solid feed additive is a powder (e.g., a flowable powder), granule (i.e., a granulate), particle (i.e., particulate), pellet, cake, water soluble concentrate, paste, bolus, tablet, dust, a component thereof, or combinations thereof.

In some embodiments, the method comprises administering a liquid feed additive comprising the cells. In some embodiments, the method comprises administering the cells in a liquid. In some embodiments, the liquid is a solution (e.g., an aqueous, organic, or aqueous-organic solution), suspension, emulsion, drench, spray, injectable, drink (e.g., a milk replacer), a component thereof, or combinations thereof. In some embodiments, the liquid is administered orally or by spraying the animal with the liquid.

In some embodiments, the method comprises combining the *M. elsdenii* cells or the feed additive comprising the cells with another animal feed additive to form a supplement or premix for adding to an animal feed. In some embodiments, the other feed additive comprises cells other than *M. elsdenii*.

In some embodiments, the *M. elsdenii* cells (e.g., freeze-dried cells) can be added to the feed additive as a liquid (e.g., in a broth or broth equivalent, including, e.g., rehydrated freeze-dried cells), reconstituted cell paste, or as lyophilized (e.g., freeze-dried) cells. The microorganisms, including freeze-dried *M. elsdenii* can also be encapsulated prior to addition to the feed additive. Dosage forms (e.g. drench of predetermined volume or capsules) can also be formed and, if desired, the microorganisms can be added directly to the animal feed, as by sprinkling a liquid broth and/or freeze-dried cells over the feed or mixing into the feed.

In some embodiments, the method comprises rehydrating a solid feed additive (e.g., a powder, granulate, particulate, pellet, cake, freeze-dried cells, or combinations thereof) to produce a liquid for administration.

In some embodiments, the method comprises applying *M. elsdenii* cells to animal feed through a delivery system that rehydrates a solid feed additive or freeze-dried cells, including on a batch to batch basis. For example, a freeze-dried powder can be augured from a polyvinyl hopper into a flushing system, which dilutes the powder and sprays it on the feed to be mixed.

In some embodiments, the method comprises applying *M. elsdenii* cells to animal feed using a volumetric metering device with a storage bin. For example, freeze-dried cells (e.g., a powder comprising the cells) can be stored in the storage bin and discharged into a water or aqueous bath just prior to being sprayed onto an animal feed.

In one aspect, the present invention is directed to a method for treating or preventing a condition or disorder associated with lactic acid production in the gastrointestinal tract of an animal, comprising administering to the animal an effective amount of *M. elsdenii* cells (e.g., freeze-dried cells) as disclosed herein, freeze-dried *M. elsdenii* cells produced by a method as disclosed herein, a feed additive as disclosed herein, or a composition (e.g., a capsule) as disclosed herein.

In some embodiments, the condition or disorder is acidosis. In some embodiments, the condition or disorder is ruminal acidosis. In some embodiments, the condition or disorder is respiratory disease. In some embodiments, the condition or disorder is laminitis. In some embodiments, the condition or disorder is an infection. In some embodiments, the infection is with *Salmonella* or *Campylobacter*. In some embodiments, the *Salmonella* is *Salmonella enterica* and/or *Salmonella bongori*. In some embodiments, the *Salmonella* serotype is *Salmonella* typhimurium and/or *Enteritidis*. In some embodiments, the *Campylobacter* is *Campylobacter jejuni* or *Campylobacter coli*.

In another aspect, the present invention is directed to a method for preventing or decreasing the growth of an opportunistic microorganism in the gastrointestinal tract of an animal, comprising administering to the animal an effective amount of *M. elsdenii* cells (e.g., freeze-dried cells) as disclosed herein, freeze-dried *M. elsdenii* cells produced by a method as disclosed herein, a feed additive as disclosed herein, or a composition as disclosed herein.

In some embodiments, the opportunistic microorganism is pathogenic. In some embodiments, the opportunistic microorganism is *Salmonella* or *Campylobacter*. In some embodiments, the *Salmonella* is *Salmonella enterica* and/or *Salmonella bongori*. In some embodiments, the *Salmonella* serotype is *Salmonella Typhimurium* and/or *Enteritidis*. In some embodiments, the *Campylobacter* is *Campylobacter jejuni* or *Campylobacter coli*.

In another aspect, the present invention is directed to a method of improving the bioavailability of plant-derived phosphorous in the diet of an animal, comprising administering to the animal an effective amount of *M. elsdenii* cells (e.g., freeze-dried cells) as disclosed herein, freeze-dried *M. elsdenii* cells produced by a method as disclosed herein, a feed additive as disclosed herein, or a composition as disclosed herein. In some embodiments, the *M. elsdenii* cells comprise a phytase activity. In some embodiments, the method reduces environmental phosphorous waste resulting from administration of an animal diet in the absence of *M. elsdenii* cells.

In another aspect, the present invention is directed to a method of improving growth performance in an animal, comprising administering to the animal an effective amount of *M. elsdenii* cells (e.g., freeze-dried cells) as disclosed herein, freeze-dried *M. elsdenii* cells produced by a method as disclosed herein, a feed additive as disclosed herein, or a composition as disclosed herein. In some embodiment, the improved growth performance in the animal is an improvement in: feed intake, average daily gain, feed conversion ratio, carcass gain, milk production in a milk-producing animal, egg production in poultry, bone mineralization, or combinations thereof.

In another aspect, the present invention is directed to a method of acidifying the lower gastrointestinal tract of an animal, comprising administering to the animal an effective amount of *M. elsdenii* cells (e.g., freeze-dried cells) as disclosed herein, freeze-dried *M. elsdenii* cells produced by a method as disclosed herein, a feed additive as disclosed herein, or a composition as disclosed herein. In some embodiments, the lower gastrointestinal tract is the ceca of a poultry animal.

In some embodiments, *M. elsdenii* cells (e.g., freeze-dried cells) as disclosed herein, freeze-dried *M. elsdenii* cells produced by a method as disclosed herein, a feed additive as disclosed herein, or a composition as disclosed herein is administered prior to, concomitantly with, or after feeding the animal with a food.

In some embodiments, the method further comprises mixing freeze-dried *M. elsdenii* cells as disclosed herein, the freeze-dried cells produced by a method as disclosed herein, or a solid feed additive as disclosed herein with a liquid prior to administration.

In some embodiments, a liquid is administered orally (e.g., an oral drench) or by spraying (e.g., mist spraying) the animal with the liquid.

In some embodiments, the method comprises a single administration of *M. elsdenii* cells (e.g., freeze-dried cells) as disclosed herein, freeze-dried *M. elsdenii* cells produced by a method as disclosed herein, a feed additive as disclosed herein, or a composition as disclosed herein.

In some embodiments, the method comprises a daily administration of *M. elsdenii* cells (e.g., freeze-dried cells) as disclosed herein, freeze-dried *M. elsdenii* cells produced by a method as disclosed herein, a feed additive as disclosed herein, or a composition as disclosed herein. In some embodiments, the administration is at least once daily, at least twice daily, at least three times daily, or more than three times daily. In some embodiments, the administration is ad libitum (e.g., self-administration by drinking an available liquid or eating an available food comprising the *M. elsdenii* cells (e.g., freeze-dried cells), the freeze-dried *M. elsdenii* cells produced by a method as disclosed herein, the feed additive, or the composition).

In some embodiments, the method comprises more than one administration on a single day of *M. elsdenii* cells (e.g., freeze-dried cells) as disclosed herein, freeze-dried *M. elsdenii* cells produced by a method as disclosed herein, a feed additive as disclosed herein, or a composition as disclosed herein. In some embodiments, the administration is two, three, four, five, six, or more administrations on a single day. In some embodiments, the method comprises more than one administration on a single day followed by one or more days without administration. In some embodiments, the one or more days without administration is one, two, three, four, five, or six days, one week, two weeks, three weeks, or four weeks, one month, two months, three months, four months, five months, or six months without administration.

In some embodiments, the animal is a ruminant. In some embodiments, the ruminant can be, but is not limited to, cattle, buffalo, sheep, goats, deer, reindeer, moose, giraffe, yaks, and elk. In some embodiments, the ruminant is selected from the group consisting of: cattle, buffalo, sheep, goats, deer, and reindeer.

In some embodiments, the animal is a non-ruminant. In some embodiments, the non-ruminant can be, but is not limited to, equines, poultry, swine, dogs, and cats. In some embodiments, the non-ruminant is selected from the group consisting of: equines, poultry, and swine.

In some embodiments, the animal is a zoo animal.

In some embodiments, the animal is a poultry animal. In some embodiments, the poultry animal is an avian (i.e., bird) that is used as a food animal including, but not limited to, a chicken, goose, duck, quail, turkey, pigeon, emu, or ostrich. In some embodiments, the poultry animal is selected from the group consisting of: a chicken, a goose, a duck, a quail, a turkey, or a pigeon. In some embodiments, the poultry animal is selected from the group consisting of: a broiler, a broiler breeder, and a layer. In some embodiments, the poultry animal is a chicken.

In some embodiments, the animal is an equine. In some embodiments, the equine is a horse, a pony, a donkey, or a mule.

EXAMPLES

Reference is now made to the following examples, which together with the above descriptions illustrate some embodiments of the invention in a non-limiting fashion.

Example 1

Effect of Temperature on Yield of Liquid Cultures of *M. elsdenii*

Figure 1:
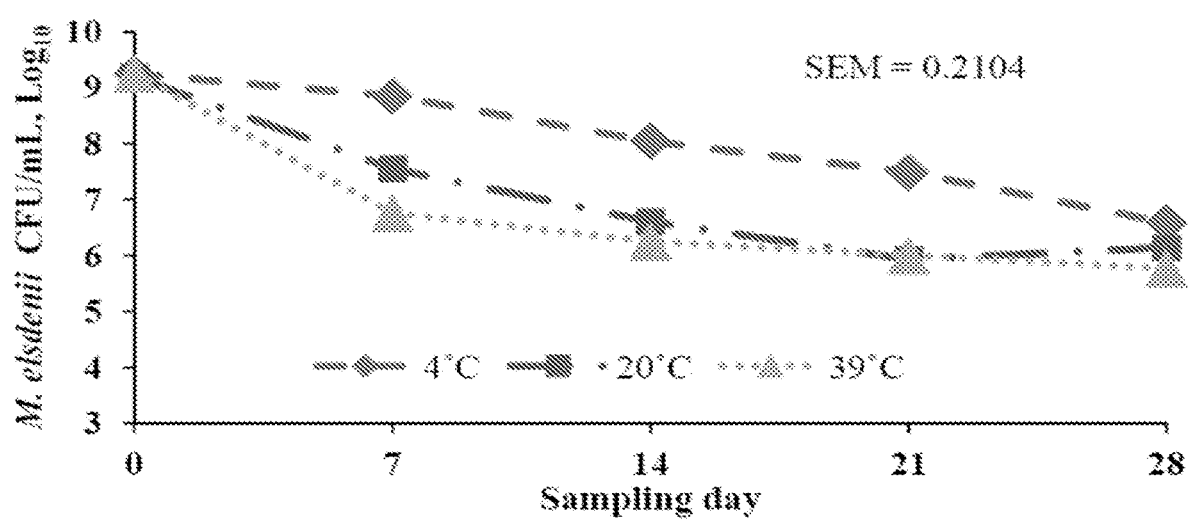
FIG. 1 shows the effect of storage temperature on viability of liquid cultures of *Megasphaera elsdenii* NCIMB 41125 over a 28-day period in terms of yield of *M. elsdenii* cells in colony forming units per milliliter ("CFU/mL") in logarithmic ("Log 10") scale.

Storage temperatures of 4° C., 20° C., and 39° C., were tested to assess viability of cells in liquid cultures of *M. elsdenii* NCIMB 41125 (Lactipro®) after 0, 7, 14, 21, and 28 days. Results revealed that storing the product at 4° C. significantly (P<0.001) improved viability of the culture compared to storage at 20° C. or 39° C., regardless of sampling day. After 28 days, product stored at 4° C. had $3.98 \times 10^6$ colony forming units per milliliter (CFU/mL) compared to $1.26 \times 10^6$ and $6.3 \times 10^5$ CFU/mL for product stored at 20° C. or 39° C., respectively (P<0.01; FIG. 1). Thus, the results show that a decreased storage temperature improves viability of liquid cultures of *M. elsdenii* NCIMB 41125.

Figure 2:
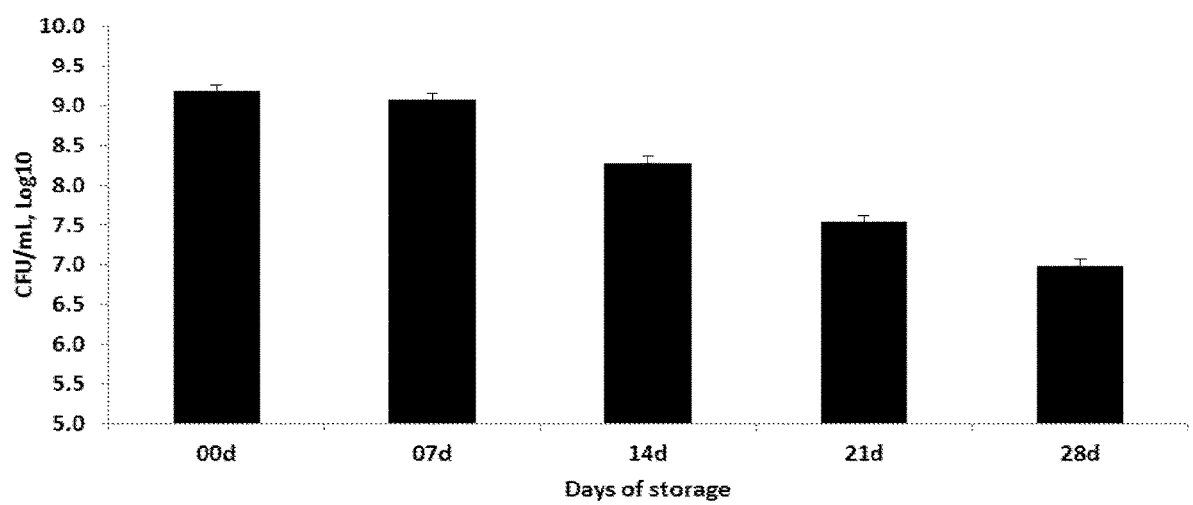
FIG. 2 shows the viability of liquid cultures of *M. elsdenii* NCIMB 41125 after 0, 7, 14, 21, and 28 days of storage at room temperature in terms of yield of *M. elsdenii* cells in CFU/mL in Log 10 scale.

Additional data from a separate study shows that *Megasphaera elsdenii* NCIMB 41125 yield in a liquid culture (Lactipro Advance®) decreases after 0, 7, 14, 21, and 28 days of storage at room temperature (FIG. 2).

Example 2

Use of Tangential Flow Filtration for Concentrating Cultures of *M. elsdenii*

Tangential flow filtration (TFF) was investigated as a method for concentrating large volumes of culture at high throughput.

Figure 3:
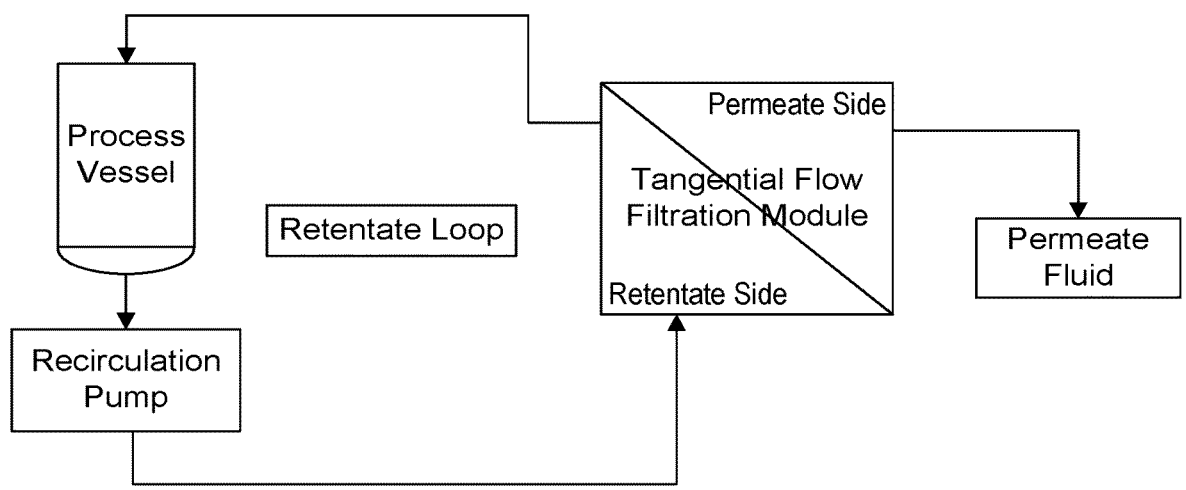
FIG. 3 shows a schematic of a tangential flow filtration ("TFF") system.

A pilot scale TFF system (see FIG. 3) was integrated into the production line for *M. elsdenii* and tested on 500-Liter (L) production runs to assess the pilot scale system at the volume reduction levels of 70%, 80%, and 90%. A TFF Module with one RC 100 kDa membrane (0.875 mm channel height) was used. Three production runs were performed for each reduction level for a total of nine runs. Samples were collected for each run and were analyzed for pH, optical density (OD), presence or absence of aerobic contaminants, volatile fatty acids profile, *M. elsdenii* concentration, osmolarity, and growth characteristics. The samples were collected from the nine *M. elsdenii* cultures ("Non-Freeze-Dried") before the start of filtration, from the permeate ("Permeate"), which is the volume removed by the system, and from the retentate ("Retentate"), which is the concentrated *M. elsdenii* culture volume comprising the cells that remains after the volume reductions.

Permeate samples collected at the beginning, middle, and end of the concentration process had consistent OD readings across volume reduction levels, all below 0.045 (data not shown). The amount of *M. elsdenii* recovered in the permeate increased over the course of the concentration process (P=0.0006), but was still negligible (less than $3 \times 10^4$ CFU/mL) in comparison to the amount of cells collected in the retentate (<0.002%). Volume reduction levels did not have an effect on *M. elsdenii* concentration recovered in permeate (P>0.9; Table 2).

TABLE 2

Average *M. elsdenii* yield in samples collected during the nine production runs performed to evaluate the pilot scale TFF system at 70%, 80%, and 90% volume reductions

| Samples | CFU/mL, Log10 | | | Standard Error | Trt effect, P-value |
|---|---|---|---|---|---|
| | 70% | 80% | 90% | | |
| Permeate | 1.19 | 1.07 | 1.12 | 0.40 | 0.958 |
| Retentate | 8.99 | 9.04 | 9.25 | 0.03 | <0.0001 |

*M. elsdenii* yield in the retentate was not different in bags collected at the beginning, middle, or end of each bagging process (P=0.6088; data not shown). Retentate yield was affected by volume reduction levels (P<0.0001; Table 2 and FIG. 4). The 90% volume reduction retentate had higher yield than the 70% and the 80% volume reduction retentate (P<0.0001). But, the 70% and the 80% retentate were not different from one another (P>0.09).

The filtration process did not affect the capacity of *M. elsdenii* cells to grow when inoculated back into SDL-20 media (Table 3). Slopes of the exponential phase were not affected by the volume reduction level (P>0.3), but were affected by the type of sample: "Retentate" versus "Non-Freeze-Dried" (P<0.001). Lag time was affected by both volume reduction level and sample type (P<0.001). Lag time for the retentate decreased with increasing volume reduction, which was representative of higher cell concentration.

TABLE 3

Comparison of slope and lag time between initial *M. elsdenii* (pre-filtration = Non-Freeze-Dried) and retentate (post-filtration) collected during the different volume reduction TFF runs

| | Sample type | | | | | | Effects, P-values | | |
|---|---|---|---|---|---|---|---|---|---|
| | Non-Freeze-Dried | | | Retentate | | | Sample type | Vol. red. | Interaction |
| | 70% | 80% | 90% | 70% | 80% | 90% | | | |
| Slope | 0.39 | 0.36 | 0.37 | 0.44 | 0.42 | 0.43 | <0.001 | 0.329 | 0.979 |
| Lag time, h | 1.42$^a$ | 1.10$^b$ | 1.07$^b$ | 0.32$^c$ | 0.29$^c$ | 0.24$^c$ | 0.001 | <0.001 | <0.001 |

Example 3

Freezing and Freeze-Drying Parameters for *M. elsdenii*

A. Freezing and Freeze-Drying of Retentates

Retentates obtained through TFF were used to test freezing protocols, cryoprotectant inclusion, and various freeze-drying parameters.

Retentates were transferred to sterile degassed serum bottles and aseptically mixed with the different cryoprotectant formulations (w/v): no cryoprotectant (Ctrl), skim milk (SM), trehalose (T), and betaine. Retentates mixed with the appropriate cryoprotectant were sampled to determine pre-freeze-drying *M. elsdenii* concentration (i.e., viability count). Mixtures were transferred into 10 mL vials (4 mL/vials) and snap frozen in liquid nitrogen or slowly frozen at −80° C. overnight. Vials were transferred to the freeze-dryer to be lyophilized using either a slow or a rapid cycle. Once freeze-drying was complete, survival of the bacteria was determined by resuspending the lyophilized product in the anaerobic chamber with anaerobic diluent, allowing it to rehydrate for 40 minutes at room temperature, and then plating onto SDL20 agar.

Cell loss was computed by subtracting the concentration of *M. elsdenii* recovered post freeze-drying from the initial concentration of *M. elsdenii* measured in the corresponding retentate mixed with cryoprotectants or not. SAS® software was used to compute cell-loss data by analyzing the interactions between volume reduction levels (70%, 80%, or 90%), freeze-drying cycle (Slow versus Rapid), freezing method (−80° C. versus Liquid Nitrogen), cryoprotectants (None, Betaine, Trehalose, Skim Milk, Maltodextrin, Trehalose/Skim Milk (T/SM), and Maltodextrin/Skim Milk (M/SM)).

Cell loss observed in the control treatment (no cryoprotectants) regardless of other criteria were 5 Log (CFU/mL) or higher. Likewise, cell loss observed in the betaine treatment regardless of other criteria was 3.96 Log CFU/mL or higher. Acceptable cell loss limit was set at 1.6 log CFU/mL. Retentates mixed with T/SM or M/SM were all below that threshold regardless of the freeze-drying cycle or the freezing method used with the exception of T/SM frozen at −80° C. and freeze-dried using the slow or rapid cycle (FIG. 5).

B. Effects of Freeze-Drying Conditions on Storage

*Megasphaera elsdenii* NCIMB 41125 was concentrated 10× using a filtration device, and freeze-drying assays were performed testing different characteristics: fast or slow initial freezing (liquid nitrogen versus −20° C.), with or without trehalose (0%, 4%, 7.5%, and 10%), and gentle or rapid freeze-drying cycles (38 h at $2\times10^{-6}$ Torr versus 16.5 h at $135\times10^{-6}$ Torr). All freeze-dried processes tested resulted in products able to retain sufficient viability to initiate growth of the culture after rehydration, even after prolonged storage of 4 to 12 months at room temperature. Differences in bacteria viability were, nevertheless, observed depending on the freeze-drying characteristics used (FIG. 6). Slow freezing, 7.5% trehalose incorporation, and gentle freeze-drying steps maintaining final water activity above 0.04 were associated with greater survival of *Megasphaera elsdenii*.

C. Effects of Cryoprotectants on Viability of Freeze-Dried *M. elsdenii*

Centrifuged *M. elsdenii* NCIMB 41125 cell concentrates were resuspended in infant milk formula prior to lyophilization, resulting in only a 1-log decrease in cell viability when cells were subsequently rehydrated. The addition of 4% trehalose and 7.5% skim milk to *M. elsdenii* concentrate was tested before slow freezing at −80° C. or snap freezing in liquid nitrogen to determine cell loss encountered during the initial freezing process. As shown in FIG. 7, snap freezing with 4% trehalose or 7.5% skim milk yielded the greatest recovery of viable cells (0.79 log reduction in viable cell count). Product without addition of cryoprotectants, regardless of the freezing technique used, lost between 2.34 and 1.95 log CFU/mL of *Megasphaera elsdenii*.

Example 4

Effects of Storage Conditions on Yield and Stability of Freeze-Dried *M. elsdenii*

To determine the effect of freeze-drying protocols and storage conditions on *Megasphaera elsdenii* NCIMB 41125 growth characteristics and shelf life, retentate obtained from 90% volume reduction was mixed with 8% trehalose/15% skim Milk (T/SM) or 8% maltodextrin/15% skim milk (M/SM), frozen at −80° C. or in liquid nitrogen (LiqN), and freeze-dried using the rapid cycle. Retentate samples were then tested for bacterial growth characteristics and cell survival during storage at 4° C. or 25° C. in aerobic or anaerobic conditions for 0, 2, 4, 8, 12, 16, 20, and 24 weeks using growth curve analysis and spread plating technique. Briefly, stored products were sampled, serially diluted, and plated onto a SDL agar plate. In addition, growth medium (SDL) was inoculated (1:100) with the rehydrated freeze-dried products and optical density (OD, 600 nm) recorded until the cultures reach stationary phase. The experiment was repeated on 3 different days and all treatments were performed in triplicate. The rehydrated freeze-dried samples were diluted in order to perform growth curves because without diluting, the absorbance was above the limit due to the presence of skim milk. In order to facilitate growth curves comparison, the same dilution was performed on the Non-freeze-dried samples used as control.

RESULTS: Samples were freeze-dried and stored at room temperature or 4° C. under aerobic or anaerobic conditions for 6 months. Samples stored in aerobic conditions regardless of the treatment rapidly decayed with an additional cell loss in comparison to their anaerobic counterpart ranging from 0.4 to 3.2 Log after only 2 weeks of storage. Based on those results and to improve figure clarity, only cell loss observed in freeze-dried products stored anaerobically are presented in FIG. 8. During storage in anaerobic conditions, samples stored at room temperature decayed faster than they counterpart stored at 4° C., with the exception of T/SM samples frozen in liquid nitrogen. T/SM samples frozen in liquid nitrogen and stored at room temperature post freeze-drying did not statistically lose more cells than their counterpart stored at 4° C. over the 16-week storage period (P>0.1). However, differences between samples became significant between the room temperature and 4° C. storage after 20 weeks of storage (P=0.0002), with a 0.84 log difference after 20 weeks and a 0.89 log difference after 24 weeks of storage. All M/SM samples decayed faster than their T/SM counterpart. After 24 weeks of storage (FIG. 9), cell loss in T/SM samples frozen in liquid nitrogen and stored at 4° C. under anaerobic conditions was significantly lower than any of the other treatments (P<0.02). T/SM samples frozen in liquid nitrogen and stored at 4° C. under anaerobic conditions had a 2.16 log loss compared to the *M. elsdenii* concentration observed prior to freeze-drying, with 0.82 log loss resulting from the 24-week storage period. On each sampling day, a growth curve experiment was performed to compare the growth characteristic of the freeze-dried products to the non-freeze-dried product. FIG. 10 shows the growth curves performed on samples frozen in liquid nitrogen, freeze-dried with the rapid cycle (18.5 hours at 250 mTorr), and stored anaerobically at 4° C. or room temperature. Non-freeze-dried samples used for each growth curve were "fresh" (no more than 2-days of age). Freeze-dried product stored at 4° C. had shorter lag time than the freeze-dried product stored at room temperature, which is consistent with the difference in *M. elsdenii* concentration observed in these samples (Table 4). After 16 weeks of storage T/SM samples regardless of the storage temperature had shorter lag time than the M/SM samples.

TABLE 4

Lag time observed on non-freeze-dried or rehydrated freeze-dried sample obtained from 90% volume reduction retentate, mixed with 8% trehalose/15% skim Milk (T/SM) or 8% maltodextrin/15% skim milk (M/SM), frozen in liquid nitrogen (LiqN), and freeze-dried using the rapid cycle after 12, 16, 20 or 24 weeks of storage under anaerobic conditions at 4 or 25° C.

| | Lag time (hour) after X weeks of storage | | | | | |
|---|---|---|---|---|---|---|
| | 12 | 16 | 20 | 24 | Average | Std. dev. |
| Lactipro | 2.50 | 2.75 | 3.75 | 1.75 | 2.69 | 0.72 |
| M/SM stored at 25° C. | 8.50 | 9.00 | 10.00 | 11.75 | 9.81 | 1.24 |
| T/SM stored at 25° C. | 6.50 | 6.75 | 7.25 | 8.00 | 7.13 | 0.57 |
| M/SM stored at 4° C. | 5.75 | 8.25 | 8.00 | 8.75 | 7.69 | 1.15 |
| T/SM stored at 4° C. | 4.25 | 5.25 | 5.00 | 4.75 | 4.81 | 0.37 |

Slopes for non-freeze-dried and MSM treatment stored at 25° C. for 12 weeks and MSM treatment stored at 20° C. for 16 weeks were abnormally low (Table 5). After 20 and 24 weeks of storage, exponential phase slopes of freeze-dried samples were not numerically different from the non-freeze-dried control.

TABLE 5

Slopes of exponential phase observed on non-freeze-dried or rehydrated freeze-dried sample obtained from 90% volume reduction retentate, mixed with 8% trehalose/15% skim Milk (T/SM) or 8% maltodextrin/15% skim milk (M/SM), frozen in liquid nitrogen (LiqN), and freeze-dried using the rapid cycle after 12, 16, 20 or 24 weeks of storage under anaerobic conditions at 4 or 25° C.

| | Exponential phase slopes after X weeks of storage | | | | | |
|---|---|---|---|---|---|---|
| | 12 | 16 | 20 | 24 | Average | Std. dev. |
| Lactipro | 0.22 | 0.31 | 0.34 | 0.31 | 0.30 | 0.04 |
| M/SM stored at 25° C. | 0.24 | 0.18 | 0.33 | 0.29 | 0.26 | 0.05 |

TABLE 5-continued

Slopes of exponential phase observed on non-freeze-dried or rehydrated freeze-dried sample obtained from 90% volume reduction retentate, mixed with 8% trehalose/15% skim Milk (T/SM) or 8% maltodextrin/15% skim milk (M/SM), frozen in liquid nitrogen (LiqN), and freeze-dried using the rapid cycle after 12, 16, 20 or 24 weeks of storage under anaerobic conditions at 4 or 25° C.

| | Exponential phase slopes after X weeks of storage | | | | | |
|---|---|---|---|---|---|---|
| | 12 | 16 | 20 | 24 | Average | Std. dev. |
| T/SM stored at 25° C. | 0.31 | 0.30 | 0.34 | 0.32 | 0.32 | 0.02 |
| M/SM stored at 4° C. | 0.30 | 0.33 | 0.30 | 0.30 | 0.31 | 0.01 |
| T/SM stored at 4° C. | 0.32 | 0.31 | 0.33 | 0.32 | 0.32 | 0.01 |

Example 5

Efficacy and Safety of Freeze-Dried *M. elsdenii* in Cattle

A. Freeze-Dried Product Preparation and Shelf Life.

Vials used in this trial as an upfront rehydrated *M. elsdenii* culture (for Rehydrated and Topdress treatments) were prepared 56 days before the start of the experiment and were stored in the fridge at 4° C. while awaiting use. Each vial contained the equivalent of 5 mL of freeze-dried product. Vials were freeze-dried in 6 different freeze-drying runs. For each run, 3 vials were rehydrated post freeze-drying and 3 additional vials were rehydrated on the day of the study to determine *M. elsdenii* concentration per vials (Table 6). Animals from Rehydrated and Top-dress group each received the content of a vial at drenching, equivalent to $1.84 \times 10^{10}$ CFU of *M. elsdenii*.

TABLE 6

*M. elsdenii* concentration post freeze-drying and on the day of the study after 56 days of storage at 4° C.

| Vial-freeze-drying-run | CFU per vial | |
|---|---|---|
| | Post-freeze-drying | On the day of the study |
| Run#1 | 2.37E+10 | 1.70E+10 |
| Run#2 | 2.37E+10 | 1.97E+10 |
| Run#3 | 3.31E+10 | 1.86E+10 |
| Run#4 | 3.41E+10 | 1.81E+10 |
| Run#5 | 1.98E+10 | 1.57E+10 |
| Run#6 | 2.34E+10 | 2.14E+10 |
| Average | 2.63E+10 | 1.84E+10 |

After the start of the experiment, extra vials from Run #5 and #6 were kept at 4° C. and 3 vials from each run of these runs were rehydrated each month (FIG. 11).

*M. elsdenii* concentration in the vials changed from $4.96 \times 10^{10}$ CFU/g to $4.17 \times 10^{10}$ CFU/g during the 11-month storage at 4° C., representing only a 0.07 log loss in yield.

Products used in this trial as a daily top-dress *M. elsdenii* culture (Top-dress treatment) were prepared about 30 days before the start of the experiment and were stored in the freezer in polyfoil bags. Top-dress products were freeze-dried in 6 different freeze-drying runs, packaged in 15 individual polyfoil bags (1 bag/day on feed), flushed with nitrogen, sealed, and stored at −80° C. until use. For each freeze-drying run, 3 packages were rehydrated post freeze-drying. Average *M. elsdenii* concentration was $4 \times 10^{10}$ CFU/package. Three additional packages were rehydrated at the beginning of each week and used to determine *M. elsdenii* concentration given to animals daily by adding rehydrating solution the *M. elsdenii* cells, allowing the cells to sit for 40 minutes, diluting the cells, and plating the cells (FIG. 12). Statistical analysis showed an increase in cell concentration over time. All product was prepared 30 days before the beginning of the study, and product used as top dress was about 80 days old at the end of the study. Animals received on average $2.19 \times 10^8$ CFU of *M. elsdenii* daily ($2.45 \times 10^{10}$ CFU/package).

B. Cattle Study

Steers (n=462; initial body weight 900 lbs) were blocked by weight and randomly assigned to one of four treatments, consisting of: a Control group receiving no *Megasphaera elsdenii* (17 pens; 7 head/pen)); a Non-Freeze-Dried group receiving 50 mL of *M. elsdenii* product containing $2 \times 10^8$ CFU/mL ($10^{10}$ CFU of *Megasphaera elsdenii* NCIMB 41125) upfront (16 pens; 7 head/pen); a Rehydrated group receiving a lyophilized culture that was rehydrated immediately prior to administration ($10^{10}$ CFU of *Megasphaera elsdenii* NCIMB 41125) upfront (16 pens; 7 head/pen); and a Top-dress group receiving a lyophilized culture that was rehydrated immediately prior to administration ($10^{10}$ CFU of *Megasphaera elsdenii* NCIMB 41125) upfront and a lyophilized product that was incorporated into the diet as a Top-dress daily for the duration of the study ($10^8$ CFU of *Megasphaera elsdenii* NCIMB 41125 daily; 17 pens; 7 head/pen). Non-freeze-dried, Rehydrated, and Top-dress groups of steers were placed on a 10-day step-up program after receiving their upfront drench of *Megasphaera elsdenii*, whereas the control group was placed on a 21-day step-up program. Ruminal fluid was extracted via rumenocentesis 26 hours after the first ration was fed. Ruminal fluid samples were analyzed for pH, volatile fatty acid concentrations, endotoxin levels, and capacity for utilization of lactic acid in an in vitro disappearance assay. For the lactate disappearance assay, ten 10-mL tubes containing semi-defined lactate medium were inoculated with 0.1 mL of ruminal fluid. Optical density was measured in duplicate every 6 hours for a 24-hour period to assess capacity for growth with lactic acid as the primary substrate. Tubes were placed in the freezer immediately after optical density was observed for subsequent determination of lactic acid concentration. One steer per pen was equipped with a continuous, radio frequency bolus to track pH measurements over the 56-day study. Steers were weighed on day 0, 28, and 56 to determine average daily gain, dry matter intake, and feed efficiency.

To assess viable *M. elsdenii* ingested by the animals, freeze-dried products were top-dressed onto sterilized ground corn in aluminum pans and collected samples after 0, 1, 2, and 4 hours of exposure to ambient atmosphere in the laboratory or outside in the sun. This experiment was repeated 4 times over the course of the months of July and August 2016 (FIG. 13). Statistical analysis revealed an exposure time by storage conditions interaction (P=0.0007), an exposure time effect (P<0.0001), and a storage conditions effect (P<0.0001). *M. elsdenii* concentration in freeze-dried product mixed with ground corn and exposed to atmosphere in the laboratory numerically decreased during the 4-hour exposure but were not significantly different from their initial concentration. *M. elsdenii* concentration in the samples exposed to outside conditions decreased much faster. After 1 hour of exposure, only 6.4% of the *M. elsdenii* initially present was recovered. *M. elsdenii* concentration in the samples exposed to outside conditions were significantly different from initial concentration and from their counterpart kept at room temperature after 2 and 4 hours exposure. *M. elsdenii* concentrations in these samples were very variable from one experiment to the other, as shown by the large standard deviation. This might be attributable to differences in outside conditions (heat and humidity), but also by differences in the freeze-dried product used which may have been more or less resistant to heat and humidity. During the animal study, freeze-dried product was mixed with ground corn just before feeding and was then promptly top-dressed as feed was placed into the bunk. Animals rushed for the ground corn and consequently freeze-dried product was likely ingested less than 1 hour post mixing. Assuming the product was ingested within an hour, animals should have received about $1.4 \times 10^7$ CFU/head/day of viable cells (6.4% of the average concentration in the top-dress product $2.2 \times 10^8$ CFU/head/day).

The accelerated step-up of the *M. elsdenii* treated steers resulted in similar 28-day body weight (P=0.53; Table 7), average daily gain (P=0.71), and feed efficiency (P=0.69). The Top-dress treatment had lower dry matter intake than the control (P=0.05). Feedlot performance over the first 56 days of feeding produced similar results among treatments (P>0.10). With the control receiving a conservative 21-day step-up period, these similarities among treatments indicate accelerated step-up programs can be implemented using any of the three forms of *M. elsdenii* treatments without adversely affecting cattle health or feedlot performance.

Ruminal fluid pH (extracted 26 hours after feeding the first diet) was similar among treatments (P>0.10; Table 8). There was a difference in Total VFA concentration with the Top-dress treatment being significantly higher than the other treatments (P<0.01). Top-dress treatment had higher acetate concentration than the Rehydrated treatment (P=0.02). Although there was a significant difference in acetate concentration, the acetate:proprionate ratio was similar among treatments (P=0.96). Other VFAs were similar among treatments (P>0.18).

Endotoxin concentration in ruminal fluid (extracted 26 hours after feeding the first diet) was similar among treatments (P=0.3462; FIG. 14). Endotoxin levels were measured as an indicator of bacterial lysis in the rumen. Animal suffering from acidosis have been reported to have endotoxin levels greater than 150,000 EU/mL. Endotoxin levels measured in this study were all below that threshold regardless of the treatment.

One steer in each of 32 pens was equipped with an indwelling ruminal pH probe (8 steers/treatment) that reported ruminal pH measurements hourly over the 56-day study (FIG. 15). Average ruminal pH measurements for each treatment are reported in 1-hour intervals in FIG. 15. A treatment by day interaction (P<0.01) was detected for ruminal pH. There also were effects of treatment (P<0.01) and day of feeding (P<0.01) on ruminal pH. The accelerated step up of the *M. elsdenii* treatments did not cause the average ruminal pH to decrease into a state of clinical acidosis. As days on feed increase, the lyophilized treatments (Rehydrated and Topdress) maintain a higher ruminal pH than that of the Control and Non-Freeze-Dried treatments.

TABLE 7

Feedlot performance

| Item | Control | Non-Freeze-Dried | Rehydrated | Top-dress | SEM | P-value |
|---|---|---|---|---|---|---|
| Initial body weight, lb | 902 | 898 | 900 | 900 | 12.2 | 0.69 |
| Days 1-28 | | | | | | |
| Average daily gain, lb | 5.59 | 5.49 | 5.32 | 5.38 | 0.18 | 0.71 |
| Dry matter intake, lb[1] | 21.94$^a$ | 21.53$^{a,\,b}$ | 21.30$^{a,\,b}$ | 20.66$^b$ | 0.39 | 0.05 |
| Gain: feed | 0.2559 | 0.2596 | 0.2489 | 0.2594 | 0.007 | 0.69 |
| Day 28 body weight, lb | 1059 | 1053 | 1050 | 1051 | 13.1 | 0.53 |
| Days 1-56 | | | | | | |
| Average daily gain, lb | 4.71 | 4.74 | 4.67 | 4.61 | 0.10 | 0.81 |
| Dry matter intake, lb | 22.84 | 23.22 | 22.75 | 23.05 | 0.35 | 0.64 |
| Gain: feed | 0.2076 | 0.2047 | 0.2061 | 0.2006 | 0.006 | 0.76 |
| Day 56 body weight, lb | 1178 | 1177 | 1175 | 1171 | 12.7 | 0.75 |

[1]Means within a row without a common superscript letter are different, P < 0.05

TABLE 8

Ruminal fluid characteristics 26 hours after feeding initial diets

| Item | Control | Non-Freeze-Dried | Rehydrated | Top-dress | SEM | P-value |
|---|---|---|---|---|---|---|
| pH | 6.21 | 6.03 | 6.13 | 6.00 | 0.13 | 0.33 |
| Volatility fatty acid, mM[1] | | | | | | |
| Total | 86.3$^a$ | 88.1$^a$ | 81.1$^a$ | 93.5$^b$ | 3.97 | <0.01 |
| Acetate | 54.1$^{a,\,b}$ | 54.9$^{a,\,b}$ | 50.8$^a$ | 58.4$^b$ | 2.40 | 0.02 |
| Propionate | 20.4 | 21.2 | 19.6 | 22.6 | 1.47 | 0.18 |
| Butyrate | 10.3 | 10.6 | 9.4 | 10.8 | 0.73 | 0.44 |
| Isobutyrate | 0.24 | 0.15 | 0.09 | 0.21 | 0.08 | 0.20 |
| Valerate | 0.58 | 0.67 | 0.64 | 0.64 | 0.10 | 0.93 |
| Isovalerate | 0.67 | 0.61 | 0.50 | 0.66 | 0.11 | 0.23 |
| Caproate | 0.00 | 0.05 | 0.00 | 0.02 | 0.02 | 0.28 |
| Acetate:propionate | 2.74 | 2.67 | 2.68 | 2.72 | 0.11 | 0.96 |

[1]Means within a row without a common superscript letter are different, P < 0.01

Optical density measurements were observed in 6-hour intervals over a 24-hour period to determine the growth curves of mixed ruminal microbes inoculated into a semi-defined lactate medium, these data are presented in FIG. 16. There was an interaction between treatment and time detected (P<0.02). Individual effects of treatment (P<0.01) and time (P<0.01) were also found. No differences among treatments were detected until hour 12, when the Rehydrated freeze-dried was higher than the freeze-dried daily (P<0.02) and control (P=0.007). At hour 24, there were no differences between the *M. elsdenii* treatments (P>0.10), but the control treatment had significantly less microbial growth than all *M. elsdenii* treatments (P<0.01).

FIG. 17 illustrates L-lactate disappearance of semi-defined lactate medium inoculated with mixed ruminal microbes and incubated for 0, 6, 12, 18, or 24 hours. An interaction between treatment and time was detected (P=0.007) along with effects of treatment (P=0.01) and time of incubation (P<0.0001). The Non-Freeze-Dried treatment contained less L-lactate than other treatments at hour 0 (P=0.04). Concentrations of L-lactate were analogous among treatments over the 6, 12, and 18-hour time points (P>0.10). Similar to the results of the optical density mentioned above, the ruminal microbes from control steers utilized less lactate (P<0.003) than the *M. elsdenii* treatments collectively at 24 hours of incubation while no differences were detected among *M. elsdenii* treatments (P>0.10). These data illustrate that ruminal microbes from steers treated with *M. elsdenii* grew more efficiently in a semi-defined lactate medium than those from control steers, suggesting greater capacity for lactic acid utilization in these treatments. Moreover, *Megasphaera* treatments were similar with respect to capacity for utilization of L-lactic acid.

VFA concentrations were measured on the samples used for the optical density and lactate disappearance assays and are presented in Table 9. There was a treatment by hour interaction detected for the concentrations of total VFA (P=0.002), acetate (P=0.0002), isobutyrate (P=0.04), butyrate (P<0.0001), isovalerate (P=0.0007), and valerate (P<0.0001), as well as for the acetate:propionate ratio (P=0.02). Effects of time were found for total VFA and all individual VFAs (P<0.0001). Differences among treatments were found for isobutyrate (P=0.02), butyrate (P=0.0004), and valerate (P=0.001). Concentrations of isobutyrate were lower at hour 18 for the Non-Freeze-Dried and Top-dress treatment groups (P<0.005 and P<0.004 respectively) when compared to the control and Rehydrated. At the 24-hour time point Top-dress had less isobutyrate (P=0.002) than the Non-Freeze-Dried and Rehydrated treatments but was similar to the control (P>0.10). Butyrate concentrations of the Rehydrated samples were higher than that of the Top-dress (P=0.02) after 18 hours of incubation. The control treatment produced less butyrate in 24 hours than the *M. elsdenii* treatments (P<0.0001). Differences in butyrate were also detected among the *Megasphaera* treatments at this time point with the Non-Freeze-Dried samples containing higher concentration than the Rehydrated treatment (P=0.01). Hour 18 revealed lower valerate concentration for the Rehydrated when compared to other treatments (P=0.01). Similar observations were made for valerate and butyrate concentration at 24 hours of incubation. Controls contained less valerate than all *M. elsdenii* treatments (P<0.0001), while concentrations were higher in Non-Freeze-Dried samples than in Rehydrated (P=0.03). No main effect of treatment was detected for other VFAs (P>0.05). Negligible concentrations of isocaproate, caproate, and heptanoate were measured. A treatment×time interaction (P=0.02) was found for the acetate:propionate ratio as well as an effect of time (P>0.0001), but was similar among treatments (P=0.57).

TABLE 9

Changes in VFA profile of a semi-defined lactate medium inoculated with mixed ruminal microbes

| | Treatments | | | | | P-values | | |
|---|---|---|---|---|---|---|---|---|
| Item | Control | Non-Freeze-Dried | Rehydrated | Top-dress | SEM | Trt | Hour | Trt × hour |
| Total VFA, mM | | | | | | 0.36 | <0.0001 | 0.002 |
| 0 h$^1$ | 3.61 | 3.35 | 3.52 | 3.55 | 5.16 | | | |
| 6 h$^1$ | 6.41 | 7.17 | 7.79 | 6.62 | 5.16 | | | |
| 12 h$^2$ | 7.64 | 8.58 | 17.27 | 7.80 | 5.16 | | | |
| 18 h$^3$ | 63.01 | 49.48 | 56.45 | 53.73 | 5.16 | | | |
| 24 h$^4$ | 46.23 | 78.35 | 67.22 | 74.77 | 5.16 | | | |
| Acetate, mM | | | | | | 0.98 | <0.0001 | 0.0002 |
| 0 h$^1$ | 3.07 | 3.02 | 3.07 | 2.92 | 2.15 | | | |
| 6 h$^{1, 2}$ | 4.92 | 5.56 | 5.78 | 5.13 | 2.15 | | | |
| 12 h$^2$ | 5.77 | 6.31 | 9.17 | 6.27 | 2.15 | | | |
| 18 h$^3$ | 33.47 | 21.96 | 22.75 | 23.97 | 2.15 | | | |
| 24 h$^4$ | 17.25 | 25.43 | 22.82 | 26.05 | 2.15 | | | |
| Propionate, mM | | | | | | 0.24 | <0.0001 | 0.08 |
| 0 h$^1$ | 0.01 | 0 | 0 | 0 | 2.44 | | | |
| 6 h$^{1, 2}$ | 1.21 | 1.29 | 1.69 | 1.21 | 2.44 | | | |
| 12 h$^2$ | 1.69 | 2.00 | 6.45 | 1.47 | 2.44 | | | |
| 18 h$^3$ | 23.29 | 20.84 | 23.53 | 24.00 | 2.44 | | | |
| 24 h$^4$ | 20.85 | 33.61 | 28.77 | 32.58 | 2.44 | | | |
| Isobutyrate, mM | | | | | | 0.02 | <0.0001 | 0.04 |
| 0 h$^1$ | 0.03 | Negligible | Negligible | Negligible | 0.03 | | | |
| 6 h$^1$ | 0.01 | Negligible | Negligible | Negligible | 0.03 | | | |
| 12 h$^1$ | Negligible | Negligible | 0.02 | 0.00 | 0.03 | | | |
| 18 h$^2$ | 0.14$^a$ | 0.01$^b$ | 0.15$^a$ | 0.01$^b$ | 0.03 | | | |
| 24 h$^3$ | 0.15$^{a,b}$ | 0.22$^a$ | 0.22$^a$ | 0.08$^b$ | 0.03 | | | |
| Butyrate, mM | | | | | | 0.0004 | <0.0001 | <0.0001 |
| 0 h$^1$ | 0.08 | 0.06 | 0.08 | 0.09 | 0.52 | | | |
| 6 h$^1$ | 0.15 | 0.20 | 0.19 | 0.16 | 0.52 | | | |
| 12 h$^1$ | 0.18 | 0.25 | 0.90 | 0.16 | 0.52 | | | |

TABLE 9-continued

Changes in VFA profile of a semi-defined lactate medium inoculated with mixed ruminal microbes

| | Treatments | | | | | P-values | | |
|---|---|---|---|---|---|---|---|---|
| Item | Control | Non-Freeze-Dried | Rehydrated | Top-dress | SEM | Trt | Hour | Trt × hour |
| 18 h$^2$ | 2.71$^{a,b}$ | 3.24$^{ab}$ | 4.36$^a$ | 2.75$^b$ | 0.52 | | | |
| 24 h$^3$ | 3.46$^a$ | 8.80$^b$ | 7.06$^c$ | 7.46$^{b,c}$ | 0.52 | | | |
| Isovalerate, mM | | | | | | 0.9 | <0.0001 | 0.0007 |
| 0 h$^1$ | 0.07 | 0.01 | 0.01 | 0.03 | 0.10 | | | |
| 6 h$^1$ | 0.03 | 0.01 | 0.02 | 0.03 | 0.10 | | | |
| 12 h$^1$ | Negligible | Negligible | 0.11 | Negligible | 0.10 | | | |
| 18 h$^2$ | 0.52 | 0.29 | 0.75 | 0.26 | 0.10 | | | |
| 24 h$^3$ | 0.72 | 1.24 | 1.06 | 0.93 | 0.10 | | | |
| Valerate, mM | | | | | | 0.001 | <0.0001 | <0.0001 |
| 0 h$^1$ | 0.14 | 0.10 | 0.16 | 0.17 | 0.54 | | | |
| 6 h$^1$ | 0.05 | 0.07 | 0.08 | 0.06 | 0.54 | | | |
| 12 h$^1$ | Negligible | 0.03 | 0.63 | Negligible | 0.54 | | | |
| 18 h$^2$ | 2.63$^a$ | 2.91$^a$ | 4.63$^b$ | 2.53$^a$ | 0.54 | | | |
| 24 h$^3$ | 3.75$^a$ | 8.12$^b$ | 7.23$^c$ | 7.56$^{b,c}$ | 0.54 | | | |
| Isocaproate, mM | | | | | | 0.26 | <0.0001 | .09 |
| 0 h$^1$ | 0.10 | 0.07 | 0.09 | 0.12 | 0.02 | | | |
| 12 h$^3$ | Negligible | Negligible | Negligible | Negligible | 0.02 | | | |
| 18 h$^4$ | 0.25 | 0.20 | 0.21 | 0.20 | 0.02 | | | |
| 24 h$^5$ | 0.03 | 0.01 | negligible | 0.01 | 0.02 | | | |
| Caproate, mM | | | | | | 0.07 | <0.0001 | 0.003 |
| 0 h | 0.09 | 0.09 | 0.11 | 0.14 | 0.02 | | | |
| 6 h | Negligible | Negligible | Negligible | Negligible | 0.02 | | | |
| 12 h | Negligible | 0.02 | Negligible | Negligible | 0.02 | | | |
| 18 h | Negligible | 0.14 | 0.08 | Negligible | 0.02 | | | |
| 24 h | 0.02 | 0.11 | 0.07 | 0.10 | 0.02 | | | |
| Heptanoate, mM | | | | | | 0.09 | <0.0001 | 0.01 |
| 0 h | 0.02 | 0.06 | 0.00 | 0.02 | 0.01 | | | |
| 6 h | Negligible | Negligible | Negligible | Negligible | | | | |
| 12 h | Negligible | Negligible | Negligible | Negligible | | | | |
| 18 h | Negligible | Negligible | Negligible | Negligible | | | | |
| 24 h | Negligible | Negligible | Negligible | Negligible | | | | |
| A:P | | | | | | 0.57 | <0.0001 | 0.02 |
| 0 h$^1$ | 0.06 | Negligible | Negligible | Negligible | 0.18 | | | |
| 6 h$^{1,2}$ | 4.01 | 4.44 | 4.24 | 4.00 | 0.18 | | | |
| 12 h$^2$ | 3.98 | 4.60 | 4.17 | 4.60 | 0.18 | | | |
| 18 h$^3$ | 2.14 | 1.91 | 1.77 | 1.91 | 0.18 | | | |
| 24 h$^4$ | 1.12 | 0.82 | 0.91 | 0.91 | 0.18 | | | |

$^{1, 2, 3, 4}$Time points without a common superscript number are different, P < 0.01

$^{a, b, c}$Means within a row without a common superscript letter are different, P < 0.05

Example 6

Phytase Activity of *Megasphaera elsdenii*

The in vitro phytase activity of *M. elsdenii* cells was assessed.

*Megasphaera elsdenii* NCIMB 41125 cells were cultured under anaerobic conditions as described herein in semi-defined lactate media containing either inorganic phosphate ($KH_2PO_4$) or phytate as a phosphorous source. At 2 hour intervals from the start of culture (0 hours) until 8 hours, 1 milliliter (mL) samples were removed from the culture and centrifuged to form a cell pellet. Phytase activity in the cell pellets was then determined using the Molybdate blue method. See Yanke et al., Microbiol. 144: 1565-1573 (1998). Briefly, inorganic phosphate released by enzymatic cleavage within 30 minutes of incubation at 37° C. at pH 5.0 was quantitated by spectrophotometry at 700 nanometers (nm) and compared to a standard curve. Phytase activity was determined as the amount of inorganic phosphorus released from the cell pellet per min under the test conditions.

FIG. 18 shows that growth of the *Megasphaera elsdenii* cells in either the presence or absence of phytate resulted in significant phytase activity, which confirms that: (1)*Megasphaera elsdenii* NCIMB 41125 cells produce phytase, (2) phytase production is not inhibited by the presence of phosphorus in the media, and (3) phytase production by *Megasphaera elsdenii* appears to be greater in presence of phytate in the media.

Example 7

Effect of *Megasphaera elsdenii* on *Salmonella* Concentration and Prevalence

Day-old broiler chicks (n=384) were randomly allocated to four different treatment groups: 1) a control group receiving no *Megasphaera,* 2) an ad libitum group having free access to bottle feeders containing liquid *Megasphaera elsdenii* NCIMB 41125, 3) a freeze-dried group receiving daily freeze-dried *Megasphaera elsdenii* NCIMB 41125 in their feed, and 4) an oral gavage group receiving liquid *Megasphaera elsdenii* NCIMB 41125 on day 0.

Each of the four treatments was represented by 16 cages containing 6 birds each. Animal weights, feed consumption, and feed conversion were recorded over the 15-day trial period. After a 15-day feeding period, 2 animals per cage were randomly selected, slaughtered, and ceca were recovered to determine *Salmonella* prevalence. Briefly, ceca were retrieved, placed in Ziploc bags, and stored on ice. Ceca were then washed with 70% ethanol and manually massaged to extract content. One milliliter of the recovered content was serially diluted in phosphate buffer saline solution (PBS) and plated onto brilliant green agar (BGA). BGA plates were incubated 24 h at 37° C. Presumptive *Salmonella* colonies (pink colonies) were counted and confirmed as *Salmonella* using the Oxoid *Salmonella* latex test FT0203 (Oxoid-Thermo Scientific, Hampshire, UK). Additionally, one milliliter of cecum content sample was added to 9 mL of Rappaport-Vassiliadis (RV) for selective enrichment. If no detectable *Salmonella* growth was observed on BGA plates, RV enrichment was plated onto BGA plates, incubated for 24 h at 37° C., and evaluated for the presence of *Salmonella*. Samples with no growth with direct plating, but positive growth with RV enrichment were given an arbitrary count of 9 (1 below the theoretical detection limit) and samples with no growth in either direct plating or RV enrichment were given a count of 0.

Results indicated that birds receiving freeze-dried material had lower cecal *Salmonella* concentration in the number of colony forming units per milliliter (CFU/mL) by a difference of −1 Log as compared to the control group. See FIG. 19. The prevalence of *Salmonella* in samples of the freeze-dried group was also decreased by 13% when compared to the control group. See FIG. 20.

Example 8

Effect of *Megasphaera elsdenii* on Growth Performance and Cecal Characteristics of Broiler Chickens
A. Experimental Design and Treatments Twenty-four replicates of three treatments in a randomized complete block design using day-old male were performed using Cobb 500 broiler chicks that were one day old at the start of treatment (Cobb-Vantress in Siloam Springs, Arkansas). Treatments were *M. elsdenii* strain NCIMB 41125 (MS-Biotec, Wamego, Kansas) administered as either an oral gavage or an aerosolized mist applied to the body surface of the birds, and a control (no *M. elsdenii*). The birds were housed in 72 pens, with each pen containing 35 birds at the onset of the experiment (2,520 birds total).

Prior to administration of *M. elsdenii*, 5 L foil bags of fresh culture were vigorously shaken to homogenize contents. Tygon tubing was used to connect a manually operated dosing device to the bag. The reservoir of the dosing device was repeatedly filled and dispensed several times to evacuate air. The contents were deemed free of ambient air when the culture, which contains an oxygen indicator, retained its normal color.

Chicks were allocated into groups of 35, and the weight of each group was recorded. Groups of birds were processed by block, with experimental treatments being assigned randomly within each block.

Twenty-four pens (35 birds/pen; 840 birds total) were dosed by oral gavage with 0.2 mL of a fresh culture containing $1.97 \times 10^9$ CFU/mL of *M. elsdenii* strain NCIMB 41125 using a Scorex Classic 173.05005 auto-filling syringe (Ecublens, Switzerland). Technicians restrained the birds by using the thumb and forefinger to hold the beak open while the contents of the syringe were discharged directly into the oral cavities of the birds.

Twenty-four pens (35 birds/pen; 840 birds total) were dosed by aerosolized mist of a fresh culture containing $1.97 \times 10^9$ CFU/mL of *M. elsdenii* strain NCIMB 41125 applied by pneumatic drenching device fitted with an atomizing tip. Birds were placed into a plastic tub (50 cm×35 cm×40 cm) and the culture was applied to their body surfaces as an atomized mist at a volume of 60 mL per pen (~1.7 mL/bird).

Twenty-four pens (35 birds/pen; 840 birds total) had no contact with *M. elsdenii* and served as controls. To prevent cross contamination with treated birds, control birds were handled only by designated personnel that had no contact with treated birds and placed in designated carriers to be weighed and transferred to pens. In one case the birds were miscounted and pen 51 received 33 birds rather than 35 birds due to technician error.

B. Feeding and Watering

Fresh water was offered ad libitum through sippers (6 sippers/pen) suspended from a water supply line. The sipper height was adjusted throughout the trial to accommodate growth of the birds. Table 10, below, shows the diets used in the experiment. All diets were fed in gravity feeders suspended in the center of the pen. Feed was added as needed to ensure ad libitum access throughout the duration of the study. Five kg of starter diet were placed in gravity feeders prior to the placement of birds in pens.

TABLE 10

Compositions of diets

| Ingredient | Dietary Phase[†] | | |
|---|---|---|---|
| | Starter | Grower | Finisher |
| Ground corn | 55.26 | 59.74 | 65.06 |
| Dehulled soybean meal | 37.15 | 32.60 | 27.90 |
| Soybean oil | 3.10 | 3.35 | 3.10 |
| Ground limestone | 1.45 | 1.40 | 1.25 |
| Salt | 0.37 | 0.37 | 0.37 |
| Biofos, 21% | 1.7 | 1.6 | 1.4 |
| Sodium bicarbonate | 0.22 | 0.19 | 0.17 |
| Nutrablend poultry VTM premix | 0.25 | 0.25 | 0.25 |
| L-lysine hydrochloride | 0.33 | 0.30 | 0.17 |
| L-Methionine | 0.13 | 0.15 | 0.28 |
| L-Threonine | 0.04 | 0.05 | 0.07 |

[†]Diets were pelleted through a 3-mm die, cooled, crumbled, and dispensed into paper sacks for storage until feeding.

The starter diet was removed from the pens on d 16 of the study. Residual feed was weighed, removed from each feeder, and placed into numbered bins that corresponded with pen number. Feeders were refilled with the grower diet. This process was repeated on day 30 of the study, this time replacing the grower diet with the finisher diet. On day 36 the experiment was terminated, and the residual finisher diet was weighed and recorded for each pen.

Total feed consumption per pen for each phase (starter, grower, and finisher) was calculated as: Feed added−feed recovered Intake per bird per day was calculated as: Total feed consumed÷[daily head count in pen×total days on feed]

C. Bird Weights

Pen weights were recorded at the end of each feeding period (Starter, Grower, Finisher). At the end of the starter period (day 16) all birds in each pen were placed into a tub (50 cm×35 cm×40 cm) and weighed. The weight of the tub was subtracted from total weight to determine the weight of the birds in the pen. At the end of the grower period (day 30) all birds in each pen were placed into 2 tubs of equal weight (each 103 cm×55 cm×41 cm), weighed, and the weights added together. The weight of each tub (taken prior to the birds being placed into them) was subtracted from total weight to determine the weight of the birds in the pen. At the end of the finisher period (day 36) all birds in each pen were placed into 2 tubs of equal weight (each 103 cm×55 cm×41 cm) and weighed. This time, the scale was tared with the tubs in place. The weight of the birds in each tub were then added to determine total pen weight. The scale was re-tared between pens to account for fecal accumulation. At each of the weighing periods, head count verification was performed as birds were placed into tubs.

D. Sampling Procedures

Each week (days 7, 14, 21, 28 and 35), 1 to 3 birds were randomly selected from each pen and euthanized by cervical dislocation. Cecal contents (0.5 g) were collected and mixed with deionized water (2 mL) in a 20 mL HDPE scintillation vial (Fisher Sci.; 03-337-23B) using a vortex mixer. A portable pH meter (Thermo Scientific Orion 3-star portable pH meter, Waltham, MA) was used to determine pH. Four parts of the cecal mixture were added to 1 part 25% w/v metaphosphoric acid solution and homogenized using a vortex mixer. The sample was then transferred into 2 microcentrifuge tubes in 1-mL aliquots and frozen at $-18°$ C. to await analysis of volatile fatty acids (VFAs).

On days 7 and 21, cecal contents were split into 2 aliquots. One aliquot was used for VFA analysis and prepared as explained above. The other (0.5 g) was placed directly into a separate 20-mL HDPE scintillation vial (Fisher Sci.; 03-337-23B) and frozen ($-80°$ C.) for quantification of bacterial numbers using quantitative, real-time PCR.

E. Analysis of Cecal pH and Volatile Fatty Acids

Previously diluted and acidified cecal samples were thawed, homogenized using a vortex mixer and centrifuged at 24×g for 18 min. The aqueous supernatant was transferred to gas chromatography vials. Volatile fatty acids were measured using an Agilent 7890 gas chromatograph (Agilent Technologies, Santa Clara, CA) equipped with a DB-WAX capillary column (30 m×0.53 mm×0.5 mm film thickness; Sigma Aldrich, St. Louis, MO) and flame ionization detector. Helium was used as a carrier gas at a flow rate of 22 cm/s, with a 1-µL split injection and a split flow of 50:1. Initial oven temperature was 80° C. and temperature was increased at 10° C./min to 220° C. Inlet and detector temperatures were 250° C. Volatile fatty acids were quantified by comparison to known standards (Supelco Volatile Fatty Acid Standard Mix; Sigma-Aldrich, St. Louis, MO) containing acetate, propionate, isobutyrate, butyrate, isovalerate, valerate, isocaproate, caproate and heptanoate.

F. Carcass Measurements

Birds were slaughtered at 5 wk of age to determine carcass measurements. Feed was withheld approximately 4 h prior to slaughter. Five average sized birds were selected from each pen and placed into catch boxes for transport to the processing area. The 5 birds were weighed by pen to determine live weight just prior to slaughter by stunning and exsanguination. The birds were bled for 2 min and then placed into a rotary scalder at 63° C. for approximately 30 s. The birds were transferred to a rotary drum mechanical plucker for 30 s for feather removal. The feet, head and shanks were removed and the carcasses eviscerated through an incision around the vent. The carcasses were then weighed by pen to determine hot carcass yield.

G. Statistical Analysis

Data were analyzed using the mixed procedure of SAS® software Version 9.4. The model included fixed effect of treatment, random effect of block, and pen as the experimental unit. Significance was declared at P<0.05. Differences among least-squares means were determined using the PDiff option of SAS® software.

H. Results

Broilers demonstrated similar feed intake, feed efficiency, and average daily gain across treatments. Bird weights and mortalities also were unaffected by treatment. However, dressed yield was less for birds that received M. elsdenii as an oral gavage compared to that of control birds or birds that received M. elsdenii as an aerosolized mist.

Cecal pH was less in birds that received M. elsdenii by either mist or oral application, compared to that of control birds (P<0.01; Table 11).

TABLE 11

Effect of Megasphaera elsdenii on cecal pH and VFA concentrations

| Item* | Day | Control[1] | Mist[2] | Oral[3] | SEM | P-value Treatment[τ] | Contrast[ττ] |
|---|---|---|---|---|---|---|---|
| pH | | | | | 0.103 | T, D | 0.01 |
| | 7 | 6.87$^{A\ a}$ | 6.85$^{A\ ac}$ | 6.81$^{A\ a}$ | | | |
| | 14 | 6.67$^{A\ b}$ | 6.25$^{B\ b}$ | 6.11$^{B\ b}$ | | | |
| | 21 | 6.15$^{A\ a}$ | 6.12$^{A\ b}$ | 6.25$^{A\ b}$ | | | |
| | 28 | 6.83$^{A\ ab}$ | 6.81$^{A\ a}$ | 6.67$^{A\ ac}$ | | | |
| | 35 | 7.26$^{A\ c}$ | 7.10$^{A\ c}$ | 7.15$^{A\ d}$ | | | |
| Acetate | | | | | 3.604 | D, I | 0.91 |
| | 7 | 53.53$^{A\ a}$ | 58.66$^{A\ a}$ | 58.42$^{A\ a}$ | | | |
| | 14 | 61.79$^{A\ a}$ | 66.20$^{AB\ a}$ | 74.00$^{B\ b}$ | | | |
| | 21 | 61.48$^{A\ b}$ | 47.66$^{B\ b}$ | 46.4$^{B\ c}$ | | | |
| | 28 | 40.42$^{A\ bc}$ | 38.83$^{A\ b}$ | 42.36$^{A\ cd}$ | | | |
| | 35 | 39.13$^{A\ bc}$ | 41.83$^{A\ b}$ | 36.22$^{A\ d}$ | | | |
| Propionate | | | | | 0.608 | D, I | 0.51 |
| | 7 | 1.82$^{A\ a}$ | 1.48$^{A\ a}$ | 1.52$^{A\ a}$ | | | |
| | 14 | 2.35$^{A\ ab}$ | 2.10$^{A\ a}$ | 2.69$^{A\ ab}$ | | | |
| | 21 | 6.36$^{A\ c}$ | 4.01$^{B\ b}$ | 3.63$^{B\ bc}$ | | | |
| | 28 | 3.73$^{A\ bd}$ | 4.08$^{A\ b}$ | 4.21$^{A\ c}$ | | | |
| | 35 | 4.58$^{A\ d}$ | 5.88$^{A\ c}$ | 5.96$^{A\ d}$ | | | |
| Acetate:propionate | | | | | 2.168 | T, D, I | 0.003 |
| | 7 | 31.96$^{A\ a}$ | 41.33$^{B\ a}$ | 42.03$^{B\ a}$ | | | |
| | 14 | 29.80$^{A\ a}$ | 40.44$^{B\ a}$ | 33.69$^{A\ b}$ | | | |
| | 21 | 12.36$^{A\ c}$ | 13.62$^{A\ bcd}$ | 13.57$^{A\ c}$ | | | |
| | 28 | 13.25$^{A\ c}$ | 12.96$^{A\ cd}$ | 14.30$^{A\ c}$ | | | |
| | 35 | 9.81$^{A\ c}$ | 8.33$^{A\ d}$ | 7.80$^{A\ d}$ | | | |
| Butyrate | | | | | 1.094 | D, I | 0.73 |
| | 7 | 5.60$^{A\ a}$ | 5.54$^{A\ a}$ | 5.73$^{A\ a}$ | | | |
| | 14 | 9.45$^{A\ b}$ | 10.95$^{AB\ b}$ | 13.40$^{B\ b}$ | | | |
| | 21 | 17.79$^{A\ c}$ | 11.77$^{B\ b}$ | 13.45$^{B\ b}$ | | | |

TABLE 11-continued

Effect of *Megasphaera elsdenii* on cecal pH and VFA concentrations

| Item* | Day | Control[1] | Mist[2] | Oral[3] | SEM | P-value Treatment[τ] | Contrast[ττ] |
|---|---|---|---|---|---|---|---|
|  | 28 | 6.67$^{A\ ab}$ | 7.02$^{A\ ac}$ | 7.35$^{A\ ac}$ |  |  |  |
|  | 35 | 8.15$^{A\ b}$ | 9.70$^{A\ ab}$ | 8.40$^{A\ ac}$ |  |  |  |
| Isobutyrate |  |  |  |  | 0.055 | D | 0.04 |
|  | 7 | 0.39$^{A\ a}$ | 0.36$^{A\ a}$ | 0.34$^{A\ a}$ |  |  |  |
|  | 14 | 0.37$^{A\ a}$ | 0.35$^{A\ a}$ | 0.45$^{A\ a}$ |  |  |  |
|  | 21 | 0.38$^{A\ a}$ | 0.17$^{B\ b}$ | 0.15$^{B\ b}$ |  |  |  |
|  | 28 | 0.05$^{A\ b}$ | 0.00$^{A\ c}$ | 0.00$^{A\ b}$ |  |  |  |
|  | 35 | 0.37$^{A\ a}$ | 0.37$^{A\ ad}$ | 0.34$^{A\ a}$ |  |  |  |
| Valrate |  |  |  |  | 0.078 | D | 0.89 |
|  | 7 | 0.29$^{A\ a}$ | 0.31$^{A\ a}$ | 0.29$^{A\ a}$ |  |  |  |
|  | 14 | 0.68$^{A\ bc}$ | 0.71$^{A\ b}$ | 0.90$^{B\ b}$ |  |  |  |
|  | 21 | 1.13$^{A\ c}$ | 0.91$^{B\ b}$ | 0.96$^{AB\ b}$ |  |  |  |
|  | 28 | 0.32$^{A\ ac}$ | 0.28$^{A\ c}$ | 0.34$^{A\ a}$ |  |  |  |
|  | 35 | 0.63$^{A\ b}$ | 0.79$^{A\ b}$ | 0.68$^{A\ c}$ |  |  |  |
| Isovalerate |  |  |  |  | 0.0592 | D | 0.96 |
|  | 7 | 0.317$^{A\ a}$ | 0.292$^{A\ a}$ | 0.314$^{A\ a}$ |  |  |  |
|  | 14 | 0.375$^{A\ a}$ | 0.357$^{A\ ab}$ | 0.505$^{A\ b}$ |  |  |  |
|  | 21 | 0.419$^{A\ a}$ | 0.396$^{AB\ b}$ | 0.257$^{AB\ a}$ |  |  |  |
|  | 28 | 0.038$^{A\ b}$ | 0.040$^{A\ c}$ | 0.050$^{A\ c}$ |  |  |  |
|  | 35 | 0.325$^{A\ a}$ | 0.396$^{A\ ab}$ | 0.355$^{A\ ab}$ |  |  |  |
| Caproate |  |  |  |  | 0.0208 | T, D, I | 0.13 |
|  | 7 | 0.150$^{A\ a}$ | 0.168$^{A\ a}$ | 0.144$^{A\ a}$ |  |  |  |
|  | 14 | 0.150$^{A\ a}$ | 0.161$^{A\ a}$ | 0.292$^{B\ b}$ |  |  |  |
|  | 21 | 0.000$^{A\ bc}$ | 0.000$^{A\ b}$ | 0.001$^{A\ c}$ |  |  |  |
|  | 28 | 0.000$^{A\ c}$ | 0.000$^{A\ b}$ | 0.001$^{A\ c}$ |  |  |  |
|  | 35 | 0.000$^{A\ c}$ | 0.000$^{A\ b}$ | 0.001$^{A\ c}$ |  |  |  |
| Isocaproate |  |  |  |  | 0.0148 | D | 0.79 |
|  | 7 | 0.125$^{A\ a}$ | 0.116$^{A\ a}$ | 0.142$^{A\ a}$ |  |  |  |
|  | 14 | 0.085$^{A\ b}$ | 0.101$^{A\ a}$ | 0.078$^{A\ b}$ |  |  |  |
|  | 21 | 0.000$^{A\ c}$ | 0.001$^{A\ b}$ | 0.001$^{A\ c}$ |  |  |  |
|  | 28 | 0.000$^{A\ c}$ | 0.001$^{A\ b}$ | 0.001$^{A\ c}$ |  |  |  |
|  | 35 | 0.000$^{A\ c}$ | 0.001$^{A\ b}$ | 0.001$^{A\ c}$ |  |  |  |
| Heptanoate |  |  |  |  | 0.0239 | D | 0.88 |
|  | 7 | 0.177$^{A\ a}$ | 0.186$^{A\ a}$ | 0.146$^{A}$ |  |  |  |
|  | 14 | 0.104$^{A\ b}$ | 0.082$^{B\ b}$ | 0.103$^{AB}$ |  |  |  |
|  | 21 | 0.000$^{A\ c}$ | 0.002$^{A\ c}$ | 0.003$^{A}$ |  |  |  |
|  | 28 | 0.000$^{A\ c}$ | 0.001$^{A\ c}$ | 0.003$^{A}$ |  |  |  |
|  | 35 | 0.000$^{A\ c}$ | 0.001$^{A\ c}$ | 0.053$^{A}$ |  |  |  |
| Total VFA |  |  |  |  | 4.806 | D, I | 0.79 |
|  | 7 | 62.40$^{A\ a}$ | 67.10$^{A\ a}$ | 67.01$^{A\ a}$ |  |  |  |
|  | 14 | 75.34$^{A\ b}$ | 81.00$^{AB\ b}$ | 92.39$^{B\ b}$ |  |  |  |
|  | 21 | 87.57$^{A\ b}$ | 64.90$^{B\ a}$ | 64.82$^{B\ ad}$ |  |  |  |
|  | 28 | 51.23$^{A\ a}$ | 50.25$^{A\ c}$ | 54.29$^{A\ ac}$ |  |  |  |
|  | 35 | 53.18$^{A\ a}$ | 58.98$^{A\ c}$ | 51.97$^{A\ d}$ |  |  |  |

*VFA concentration reported in mM
[1]Control birds had no contact with *M. elsdenii*
[2]Birds that received *M. elsdenii* as an aerosolized mist applied to their body surface at a rate of ~1.7 ml/bird
[3]Birds received 0.2 ml *M. elsdenii* as an oral gavage
[τ]T = Effect of treatment; D = Effect of day of sampling; I = Interaction between treatment and day of sampling; $P < 0.05$
[ττ]Contrast '*M. elsdenii* vs. Control'
[A, B]Means within a row without a common superscript are different at $P < 0.05$
[a, b]Means within a column without a common superscript are different at $P < 0.05$ The mean cecal pH for control, aerosolized mist, and oral gavage treatments were 6.76, 6.63, and 6.60, respectively. A treatment by day interaction was detected for cecal acetate (P<0.01), propionate (P=0.03), butyrate (P<0.01), acetate:propionate ratio (P=0.01; A:P ratio), caproate (P=0.002) and total VFA (P<0.01) concentrations (Table 4). Acetate increased from day 7 to 14, peaking on day 14. Cecal contents of birds that received *M. elsdenii* as an oral gavage contained greater acetate, butyrate, and caproate concentrations than those of control birds on day 14 (P<0.01). By day 21, acetate concentration decreased across all treatments; however, the concentration of acetate in the ceca was greater in control birds when compared to birds treated with either aerosolized mist or oral gavage (P<0.01). Propionate and butyrate concentrations were also greater in cecal contents of control birds than those of birds treated with *M. elsdenii* on day 21 (P<0.01). Propionate concentration peaked on day 21 in all treatments and remained elevated until day 35, but they did not differ across treatments from day 28 to day 35 (P>0.05). The A:P ratio was greater in the cecal contents of birds treated with *M. elsdenii* compared to controls on day 7 (P<0.01), with an A:P ratio of 31.96, 41.33 and 42.03 for the control, aerosolized mist and oral gavage, respectively. On day 14 the cecal A:P ratio of birds treated with an aerosolized mist of *M. elsdenii* (40.44 mM) was greater than that of control birds (29.80 mM) or those that received an oral gavage of *M. elsdenii* (33.69; P<0.03). Cecal A:P ratio was not different across treatments on day 21 to 35 (P>0.05). Isobutyrate, valerate, isovalerate, isocaproate and heptanoate concentrations in cecal contents were not affected by treatment (P>0.10). Total cecal VFA concentration was greater in orally gavaged birds compared to control birds on d 14 (P<0.001). However, total VFA concentration was less (P<0.05) in the cecal contents of birds that received *M. elsdenii* as an aerosolized mist or an oral gavage (64.90 mM and 64.82 mM, respectively) than that of controls (87.57 mM) on day 21. Total cecal VFA concentrations were similar across treatments for days 7, 28, and 35 (P>0.30).

Example 9

Effect of *Megasphaera elsdenii* on Growth Performance of Broiler Chickens

A. Experimental Design and Treatments—Study 1

Eighteen replicates of six treatments, blocked by battery and by tier were performed using Cobb 500 broiler chicks (Cobb-Vantress in Siloam Springs, Arkansas) that were one day old at the start of treatment. Treatments were a control (no probiotic), Lactipro Advance® (non-freeze-dried liquid culture of *Megasphaera elsdenii* strain NCIMB 41125, MS Biotec, Wamego, Kansas) administered as an oral gavage, *Megasphaera elsdenii* strain KS 249 culture administered as an oral gavage, *Megasphaera elsdenii* strain ATCC® 25940 administered as an oral gavage, Lactipro Advance® (non-freeze-dried liquid culture of *Megasphaera elsdenii* strain NCIMB 41125 MS Biotec, Wamego, Kansas) applied to the body surface of birds as an aerosol, and freeze-dried *Megasphaera elsdenii* strain NCIMB 41125 (MS Biotec, Wamego, Kansas). The birds were housed in 108 pens, and each pen contained 8 birds at initiation of the experiment (1,152 total birds).

Birds were counted into groups of 8, and the weight of each group was recorded. Groups of birds were processed as blocks, and experimental treatments were assigned randomly to pens within each block.

Eighteen pens (8 birds/pen; 144 total birds) were dosed orally (gavage) with 0.2 mL of Lactipro Advance® containing of $1.97 \times 10^9$ CFU/mL of non-freeze-dried liquid culture of *Megasphaera elsdenii* strain NCIMB 41125. Eighteen pens (8 birds/pen; 144 total birds) were dosed orally (gavage) with 0.2 mL of a fresh culture containing an unknown concentration of *Megasphaera elsdenii* strain KS 249. Attempts to assess the CFU/mL for this strain were unsuccessful. Eighteen pens (8 birds/pen; 144 total birds) were dosed orally (gavage) with 0.2 mL of a fresh culture containing $1.06 \times 10^9$ CFU/mL of *Megasphaera elsdenii* strain ATCC® 25940. Birds dosed with all oral treatments were restrained in the palm of a technician's hand, the beak was held open using the thumb and forefinger, and culture was discharged directly into the oral cavity using an Eppendorf® Reference repeater pipette (Hamburg, Germany).

Eighteen pens (8 birds/pen; 144 total birds) were misted with 15 mL per pen of Lactipro Advance® containing $1.97 \times 10^9$ CFU/mL of *Megasphaera elsdenii* strain NCIMB 41125 (~1.88 mL/bird). Birds were placed in a plastic tub (50 cm long×35 cm wide, ×40 cm deep), and culture was applied to the body surface of birds as an atomized mist using a pneumatic drenching device fitted with an atomizing tip. The misted birds were handled by designated personnel and placed in designated carriers for weighing, application and transfer to pens to minimize cross-contamination.

Eighteen pens (8 birds/pen; 144 total birds) were given a topdressing (mixture of diet and freeze-dried *Megasphaera elsdenii*) containing $1.18 \times 10^7$ CFU/g of *Megasphaera elsdenii* strain NCIMB 41125 at a rate of a quarter teaspoon per bird. Treatment was added directly into the trough feeders every day at 1300 h starting on d 10 of the study.

The remaining eighteen pens (8 birds/pen; total of 144 birds) served as controls and had no contact with the probiotic product. The control birds were handled by designated personnel and placed in designated carriers for weighing and transferring to pens to minimize cross-contamination by treated birds.

B. Experimental Design and Treatments—Study 2

Eighteen replicates of two treatments, blocked by battery and by tier were performed using day-old Cobb 500 broiler chicks (Cobb-Vantress in Siloam Springs, Arkansas). Treatments were a control (no probiotic) or freeze-dried *Megasphaera elsdenii* strain NCIMB 41125 (MS Biotec, Wamego, Kansas). The birds were housed in 108 pens, and each pen contained 8 birds at initiation of the experiment (1,152 total birds).

Birds were counted into groups of 8, and weight of each group was recorded. Birds were processed as blocks, and experimental treatments were assigned randomly to pens within each block. Eighteen pens (8 birds/pen; 144 total birds) were given a topdressing (mixture of diet and freeze-dried *Megasphaera elsdenii*) containing $1.18 \times 10^7$ CFU/g of *Megasphaera elsdenii* strain NCIMB 41125 at a rate of a quarter teaspoon per bird. Treatment was added directly into the trough feeders every day at 1300 hours starting on day 10 of the study.

The remaining 18 pens (8 birds/pen; total of 144 birds) served as controls, and had no contact with the probiotic product. The control birds were handled by designated personnel and placed in designated carriers for weighing and transferring to pens to minimize cross-contamination by treated birds.

C. Feeding and Watering—Studies 1 and 2

Fresh water was available ad libitum. Prior to placing the birds in pens, 9.5 kg of a common starter diet (Table 12) were placed into trough feeders alongside each pen.

TABLE 12

| Composition of experimental diet† | |
|---|---|
| Ingredient | |
| Ground corn | 55.26 |
| Soybean meal (47% CP) | 37.15 |
| Soybean oil | 3.10 |
| Ground limestone | 1.45 |
| Biofos 21% | 1.70 |
| Salt | 0.37 |
| Sodium bicarbonate | 0.22 |
| Poultry vitamin premix | 0.25 |
| L-lysine hydrochloride | 0.33 |
| L-Methionine | 0.13 |
| L-Threonine | 0.04 |

†Diets was pelleted through a 3-mm die, cooled, and crumbled

Feed was replenished as needed to ensure ad libitum access throughout the study. Upon termination (day 18) of the experiment, unconsumed feed was removed from each feeder, weighed, and recorded. Total feed consumed by the pen was calculated as the difference between amounts added to and recovered from feeders. Daily feed intake per bird was calculated as: Total feed consumed÷[daily head count in pen×total days on feed]

D. Bird Weights—Studies 1 and 2

At the conclusion of the study, all of the birds in the pen were placed into a tub (50 cm long×35 cm wide, ×40 cm deep) and weighed. The tub weight was taken prior to the birds being placed into it and was subtracted from the total weight to ascertain the weight of the birds in the pen. Head count verification was also performed at this time.

E. Statistical Analysis—Studies 1 and 2

Data were analyzed using the mixed procedure of SAS® software 9.4. The model included fixed effect of treatment, random effect of block, and pen as the experimental unit. Significance was declared at P<0.05. Differences among least square means were determined using the PDiff option of SAS® software.

F. Results—Studies 1 and 2

For Study 1, broilers across all treatment groups showed similar daily feed intake, average daily gain, gain:feed, and mortality.

However, as shown in Table 13, Study 2 showed that average daily gain (P=0.02) and gain:feed (P=0.04) were both greater in birds receiving the freeze-dried *Megasphaera elsdenii* when compared to the control birds. See also FIG. 21, showing Feed:Gain ratio. Feed intake and mortality were not different among the treatment groups.

TABLE 13

Effect of *Megasphaera elsdenii* on broiler performance (Study 2)

| Item | Control † | Freeze-Dried‡ | SEM² | P-Value ‡‡ |
|---|---|---|---|---|
| No. of pens | 18 | 18 | — | — |
| ADG¹, g | 27.6$^a$ | 29.0$^b$ | 0.43 | 0.02 |
| Feed intake, g/d | 36.2 | 36.5 | 0.54 | 0.70 |
| Gain:feed | 0.76$^a$ | 0.80$^b$ | 0.01 | 0.04 |
| Mortalities, % | 2.08 | 0.69 | 0.93 | 0.31 |

¹Average Daily Gain
²Standard Error of the Mean
† Control treatment, no probiotic
‡Freeze-dried *Megasphaera elsdenii* was administered daily in the form of a topdressing
‡‡ P-value for overall model F-test
$a, b$Means within a row with different superscripts are different at P < 0.05

Example 10

Effect of *Megasphaera elsdenii* on Equine Cecal Fermentation

A. Experimental Design and Treatments

Eight Quarter horses, 4 mares and 4 geldings (average body weight=540 kg; SEM=75 kg), previously fitted with cecal cannulae (Beard et al., JAS 89(8): 2425-2429 (2011)), were used in a 3×3 (treatment×horse) incomplete Latin Square replicated over 3 treatment periods. Each treatment period was separated by a 28-day washout period. Treatments were (1) a negative control (no *M. elsdenii*; Control), (2) a 50 mL of fresh culture containing $1.97 \times 10^9$ CFU/mL of *M. elsdenii* strain NCIMB 41125 (Lactipro Advance®, MS Biotec, Wamego, Kansas) administered via oral drench (Drench), and (3) a 0.40 g of a freeze-dried culture containing $7.02 \times 10^8$ CFU/mL of *M. elsdenii* strain NCIMB 41125 (MS Biotec, Wamego, Kansas) administered via 2 molasses-based horse treats (Freeze-dried). Horses were randomly assigned to treatments (Table 14).

TABLE 14

Treatment Allocations

| Horse ID | Period 1 TRT | Period 2 TRT | Period 3 TRT |
|---|---|---|---|
| 0 | Freeze-dried³ | Control¹ | Drench² |
| 1 | Control | Drench | Freeze-dried |
| 2 | Drench | Freeze-dried | Control |
| 3 | Control | Drench | Freeze-dried |
| 4 | Drench | Control | Freeze-dried |

TABLE 14-continued

Treatment Allocations

| Horse ID | Period 1 TRT | Period 2 TRT | Period 3 TRT |
|---|---|---|---|
| 6 | Drench | Freeze-dried | Control |
| 7 | Freeze-dried | Drench | Control |
| 10 | Freeze-dried | Control | Drench |

¹Control - not treated with *M. elsdenii*
²Drench - horses received 50 mL *M. elsdenii* as an oral gavage ($1.97 \times 10^9$ CFU/mL) at the onset of each treatment period
³Freeze-dried - horses received *M. elsdenii* daily as a freeze-dried powder averaging $7.02 \times 10^8$ CFU/mL within 2 molasses based treats Horses were housed in individual stalls (3.05×3.66 m) within a single barn and bedded with pine shavings. Horses were randomly assigned to different stalls for each treatment period to account for any possible variation in ventilation or temperature based on location in the barn. Horses were walked daily for exercise during treatment periods.

Horses receiving the oral drench were dosed just prior to feeding on day 1 of each treatment period with 50 mL of fresh culture containing $1.97 \times 10^9$ CFU/mL of *M. elsdenii* strain NCIMB 41125 using a manually operated dosing device (60 mL Variable Automatic Drencher MKIII, NJ Phillips, NSW, Australia). Prior to administration of the probiotic culture, a 5 L bag of fresh culture was shaken vigorously to homogenize contents. A manually operated dosing device was attached to the bag using Tygon tubing and the reservoir was filled. Approximately 100 to 200 mL of the culture was discarded into a waste container to ensure that both the tubing and the device would be devoid of oxygen.

Horses in the freeze-dried probiotic treatment group were offered 2 corn and molasses based treats containing the freeze-dried product prior to the morning feeding each day. *M. elsdenii* strain NCIMB 41125 was freeze-dried in advance of the study and packaged in vacuum sealed packets each containing about 0.40 g of the freeze-dried bacterium with an average of $7.02 \times 10^8$ CFU/mL of *M. elsdenii*. One sample was plated each day to ensure consistent bacterial viability through each treatment period. If the horse refused the treat, the freeze-dried product was administered by hand as a bolus.

Remaining horses had no exposure to the probiotic during the period in which they served as controls.

B. Feed and Watering

During treatment periods, horses were fed twice daily with hay and concentrate split equally between the two feedings. Each horse was fed 1% of its body weight as-fed in brome hay per day (Table 15).

TABLE 15

Dietary Nutrient Analysis

| Components Dry Matter (DM) Basis, % | Brome Hay 1$^a$ | Brome Hay 2$^b$ | Concentrate$^c$ |
|---|---|---|---|
| DM | 90.5 | 92 | 87.9 |
| Crude Protein (CP) | 8.2 | 8.4 | 14.5 |
| Acid Detergent Fiber (ADF) | 39.2 | 42.2 | 8.1 |
| Amylase Neutral Detergent Fiber (aNDF) | 63.9 | 68.9 | 15.8 |
| Crude Fat | 2.5 | 2.1 | — |
| Starch | 1.6 | 0.8 | — |
| Ash | 7.27 | 6.93 | — |
| Digestible Energy (DE) Mcal/kg | 2.05 | 0.87 | 1.6 |
| Calcium | 0.38 | 0.3 | .87 |
| Phosphorous | 0.15 | 0.22 | .74 |

TABLE 15-continued

Dietary Nutrient Analysis

| Components Dry Matter (DM) Basis, % | Brome Hay 1[a] | Brome Hay 2[b] | Concentrate[c] |
|---|---|---|---|
| Magnesium | 0.17 | 0.16 | .17 |
| Potassium | 1.50 | 1.74 | .88 |

[a] Fed at a rate of 1% body weight as-fed/day during treatment periods
[b] Fed ad libitum during washout
[c] Fed in increasing amounts of 0.2% body weight as-fed/day to a maxium of 1% body weight as-fed during treatment periods Each horse was stepped up to 1% of its body weight in textured concentrate (analysis in Table 15, above, composition in Table 16, below) at a rate of 0.2% of its body weight per day on day 1 through day 5 and then maintained at 1% BW AF in grain for day 5 through day 7. All refusals were weighed and recorded. Stalls were equipped with automatic waterers in order to offer fresh, ad libitum water. Waterers were cleaned and checked for proper function multiple times per day.

TABLE 16

Composition of Experimental Concentrate[a]

| Ingredient, % of diet | Inclusion Level |
|---|---|
| Corn | 20.00 |
| Oats | 61.67 |
| Molasses | 10.00 |
| Soybean Meal, 48% | 5.22 |
| Limestone | 1.25% |
| Salt | 0.50% |
| Mono Calcium | 1.02% |
| Vit A 30,000 | 0.01% |
| Vit D 30,000 | 0.00% |
| Vit E 20,000 | 0.25% |
| Cu Sulfate | 0.01% |
| Zn Oxide | 0.01% |
| Na Selenite | 0.06% |

[a] Fed during treatment periods in increasing amounts of 0.2% body weight as-fed/day to a maximum of 1% body weight as-fed During the washout periods horses were housed in a dry lot and maintained on an ad libitum brome hay diet (Table **). Horses were weighed at the termination of each washout period to ensure accurate calculation of the amount of feed offered during the treatment periods.

C. Sampling Procedures

Cecal samples were collected via cecal cannulae every 4 hours during each 7 day treatment period. Horses were fed at 1000 hours and 2200 hours each day and samples were collected at 4, 8 and 12 hours post-feeding prior to the following feeding. On day 0 of each treatment period, samples were collected prior to dosing or feeding to establish baseline values of pH, VFA and *M. elsdenii* populations in the hindgut.

Samples were collected by removing the cannulae caps and catching cecal contents as they flowed out of the cannulae. Cecal fluid was strained through four layers of cheesecloth, and then placed into a 100-mL specimen cup. If a sufficient sample was not collected via gravity flow, a handheld pump was used to extract cecal contents. At 1000 hours on days 0, 1, 3 and 7, additional cecal samples were collected for PCR analysis. During the first treatment period, unfiltered samples were collected in 20-mL HDPE scintillation vials (Fischer Sci.; 03-337-23B) These unfiltered samples posed a challenge in separating samples for DNA extraction, so for the remaining 2 treatment periods strained cecal fluid was collected in 50-mL Falcon conical centrifuge tubes (Corning Inc. 352070; Corning, NY) and immediately frozen at −80° C. to await PCR analysis. Technicians changed gloves between each horse.

D. Analysis of Cecal pH and Volatile Fatty Acids pH of the strained cecal fluid was measured immediately after collection using a portable pH meter (Thermo Scientific Orion 3 Star Portable pH Meter, Waltham, MA; Accumet probe). After pH was recorded, the sample was transferred in 1 mL aliquots into 2 microcentrifuge tubes and mixed with 0.25 mL of 25% meta-phosphoric acid for deproteinization. Samples were frozen at −18° C. for at least 24 hours prior to VFA analysis.

Acidified and frozen cecal samples were thawed and homogenized using a vortex mixer and centrifuged at 24×g for 18 minutes. The aqueous supernatant was then transferred to gas chromatography vials. Volatile fatty acids were measured using an Agilent 7890 gas chromatograph (Agilent Technologies, Santa Clara, CA) equipped with a DB-WAX capillary column (10 mm×0.10 mm×0.1 mm film thickness; Agilent and J&W columns, Santa Clara, CA) and flame ionization detector. Hydrogen was used as a carrier gas at a flow rate of 46 cm/second, with a 1-µL split injection and a split flow 50:1. Initial oven temperature was 70° C. and temperature was increased by 15° C./minute to 130° C., then increased at 60° C./minute to 220° C. and held for 2 minutes. Inlet and detector temperatures were 260° C. and 300° C. respectively. Volatile fatty acids were quantified by comparing to known standards (Supelco Volatile Fatty Acid Standard Mix; Sigma-Aldrich, St. Louis, MO) containing acetate, propionate, isobutyrate, butyrate, isovalerate, valerate, isocaproate, caproate and heptanoate.

E. Statistical Analysis

Data were analyzed using the Glimmix procedure of SAS® software Version 9.4. The model included the fixed effect of treatment and random effects of horse, period and treatment by period interaction. Horse served as the experimental unit. The treatment by hour within day effect was not significant for any parameter and was therefore excluded from the model. Significance was declared at P<0.05, and a tendency was considered to be 0.05<P<0.10. Differences among least-squares means were determined using the PDiff option of SAS® software.

F. Results

Cecal pH tended to be greater in horses treated with *M. elsdenii* compared to controls as the inclusion of grain in the diet increased. See FIG. 22. Cecal pH of horses administered *M. elsdenii* as an oral drench was elevated above controls on day 5 (7.00 and 7.19 respectively; P=0.09), the first day in which the full allotment of grain was fed. On day 7, horses receiving *M. elsdenii* as a freeze-dried treat tended to have greater cecal pH (7.19) than controls (6.99; P=0.09).

Table 17 shows the VFA profile of the treatment groups.

TABLE 17

Effect of *M. elsdenii* on Equine Cecal VFA Profile

| Item* | Day | Control[1] | Drench[2] | Freeze-dried[3] | SEM | P-value Treatment[τ] | P-value Contrast[ττ] |
|---|---|---|---|---|---|---|---|
| Acetate | | | | | 5.928 | D | 0.55 |
| | 0 | 47.02[A, a] | 43.03[A, ab] | 45.73[A, a] | | | |
| | 5 | 43.72[A, a] | 40.88[A, b] | 40.08[A, a] | | | |
| | 6 | 39.41[A, b] | 38.53[A, ab] | 35.54[A, b] | | | |
| | 7 | 38.36[A, b] | 36.63[A, a] | 36.39[A, b] | | | |
| Propionate | | | | | 3.078 | D | 0.54 |
| | 0 | 14.86[A, a] | 14.12[A, acd] | 15.81[A, abc] | | | |
| | 5 | 19.22[A, ab] | 18.80[A, bc] | 18.25[A, b] | | | |
| | 6 | 17.84[A, abc] | 17.67[A, c] | 15.08[A, c] | | | |
| | 7 | 16.78[A, c] | 15.24[A, d] | 14.54[A, c] | | | |
| Acetate:propionate | | | | | 0.252 | D | 0.55 |
| | 0 | 3.50[A, a] | 3.36[A, a] | 3.47[A, a] | | | |
| | 5 | 2.37[A, b] | 2.32[A, b] | 2.32[A, b] | | | |
| | 6 | 2.33[A, b] | 2.29[A, b] | 2.46[A, b] | | | |
| | 7 | 2.41[A, b] | 2.60[A, c] | 2.83[B, c] | | | |
| Butyrate | | | | | 0.900 | D | 0.45 |
| | 0 | 5.10[A, a] | 4.26[A, ab] | 4.58[A, ab] | | | |
| | 5 | 4.70[A, a] | 4.18[A, a] | 4.22[A, b] | | | |
| | 6 | 4.15[A, a] | 3.67[A, ab] | 3.81[A, ab] | | | |
| | 7 | 3.53[A, b] | 3.36[A, b] | 3.57[A, a] | | | |
| Isobutyrate | | | | | 0.051 | I | 0.25 |
| | 0 | −0.01[A, a] | −0.01[AB, ab] | 0.12[B, a] | | | |
| | 5 | 0.01[A, a] | 0.02[A, b] | 0.07[A, a] | | | |
| | 6 | 0.00[A, a] | 0.05[A, ab] | 0.03[A, b] | | | |
| | 7 | 0.00[A, a] | 0.05[A, a] | 0.04[A, b] | | | |
| Valerate | | | | | 0.096 | I | 0.31 |
| | 0 | 0.16[A, a] | 0.04[A, a] | 0.10[A, ab] | | | |
| | 5 | 0.14[A, a] | 0.05[B, a] | 0.08[A, b] | | | |
| | 6 | 0.12[A, a] | 0.07[A, a] | 0.13[A, ab] | | | |
| | 7 | 0.04[A, b] | 0.07[A, a] | 0.15[B, a] | | | |
| Caproate | | | | | 0.0120 | — | 0.57 |
| | 0 | 0.000 | 0.000 | 0.007 | | | |
| | 5 | 0.000 | 0.000 | 0.000 | | | |
| | 6 | 0.000 | 0.000 | 0.007 | | | |
| | 7 | 0.000 | 0.000 | 0.015 | | | |
| Total VFA | | | | | 9.487 | D | 0.54 |
| | 0 | 67.14[A, ab] | 61.46[A, ab] | 66.44[A, a] | | | |
| | 5 | 67.82[A, b] | 63.97[A, b] | 62.73[A, a] | | | |
| | 6 | 61.53[A, a] | 60.06[A, ab] | 54.60[A, b] | | | |
| | 7 | 58.73[A, a] | 55.43[A, a] | 54.69[A, b] | | | |

*VFA concentration reported in mM
[1]Control - not treated with *M. elsdenii*
[2]Drench - horses received 50 mL *M. elsdenii* as an oval gavage (1.97 × 10$^9$ CFU/mL) at the onset of each treatment period
[3]Freeze-dried - horses received *M. elsdenii* daily as a freeze-dried powder averaging 7.02 × 10$^8$ CFU/mL within 2 molasses based treats
[τ]T = Effect of treatment; D = Effect of day of sampling; I = Interaction between treatment and day of sampling; P< 0.05
[ττ]Contrast '*M. elsdenii* vs. Control'
[A, B]Means within a row without a common superscript are different at P < 0.05
[a, b]Means within a column without a common superscript are different at P < 0.05

*M. elsdenii* supplementation had no effect on acetate or propionate concentrations in the cecum (P>0.10; Table **). However, a treatment by day interaction was detected in the acetate:propionate (A:P) ratio (P<0.05). The cecal A:P ratio was greater on day 7 in horses that received freeze-dried *M. elsdenii* (2.83) than that of horses that did not receive *M. elsdenii* (2.41) or those that received *M. elsdenii* as an oral drench (2.60; P<0.05). Cecal valerate was greater on day 7 in horses that received freeze-dried *M. elsdenii* (0.15 mM) than in control animals (0.04 mM) or those that received an oral drench of *M. elsdenii* (0.07 mM; P<0.02). Cecal valerate was less in drenched horses on day 5 than the control animals (P<0.01); however, it was similar to that of horses treated with freeze-dried *M. elsdenii* (P>0.10). Heptanoate and isocaproate concentrations were negligible, and no treatment or interaction effect was detected, therefore these VFAs were excluded from Table **.

Cecal pH and fermentation products were most affected by supplementation with *M. elsdenii* from day 5 to day 7, the days in which the maximum amount of grain was consumed.

Example 11

Evaluation of Liquid Culture *Megasphaera elsdenii* NCIMB 41125 (Lactipro®) Application in Broiler Chickens A pilot broiler performance study was performed at the Virginia Diversified Research Corporation to evaluate the effects of *Megasphaera elsdenii* NCIMB 41125 misted or gavaged on growth performance of broiler chicks.

Day-old broiler chicks (n=720) spray vaccinated with Coccivac-B on day 0 were randomly allocated to 6 different treatments: (1) a negative control group receiving no *Megasphaera* (nCON), (2) a mist group receiving *M. elsdenii* NCIMB 41125 on day 0 by mist (1-2 mL/bird) when in their hatchery crates (d0 Mist), (3) a day 7 gavage group receiving 2 mL of *M. elsdenii* NCIMB 41125 on day 7 by oral gavage after a 2 h feed fast and a 1 h water fast (d7 GAV), (4) a day 14 gavage group receiving 5 mL of *M. elsdenii* NCIMB 41125 on day 14 by oral gavage after a 2 h feed fast and a 1 h water fast (d14 GAV), (5) a day 21 gavage group receiving 10 mL of *M. elsdenii* NCIMB 41125 on day 21 by oral gavage after a 2 h feed fast and a 1 h water fast (d21 GAV), and 6) a positive control group (pCON) receiving no *Megasphaera* but receiving starter and grower feeds treated with BMD (50 g/t) and finisher feed treated with Stafac (20 g/t).

Each treatment was represented by 4 cages containing 30 birds each. Diets provide to the birds were as follow: starter feed from day 0-18, grower feed from day 18-35d, and finisher feed from day 35-39. Animal weights, feed consumption, and feed conversion were recorded over the 39-day trial period.

TABLE 18

Broiler performance measured after 25 and 39 days on feed.

|  | nCON | pCON | d 0 Mist | d 7 GAV | d 14 GAV | d 21 GAV |
|---|---|---|---|---|---|---|
| Live weight day 25, lbs | $2.288^a$ | $2.288^a$ | $2.237^{ab}$ | $2.160^b$ | $2.212^{ab}$ | $2.188^b$ |
| FCR, day 1-25 | $1.531^a$ | $1.516^a$ | $1.430^b$ | $1.555^a$ | $1.531^a$ | $1.571^a$ |
| Mortality day 25, % | $0.00^a$ | $0.00^a$ | $0.00^a$ | $0.83^{ab}$ | $0.00^a$ | $1.67^b$ |
| Live weight day 39, lbs | $4.713^a$ | $5.100^a$ | $4.886^a$ | $4.880^a$ | $5.121^a$ | $4.907^a$ |
| FCR, day 1-39 | $1.814^b$ | $1.754^{ab}$ | $1.739^{ab}$ | $1.771^{ab}$ | $1.715^{ab}$ | $1.674^a$ |
| Mortality day 39, % | $0.017^a$ | $0.00^a$ | $0.83^a$ | $1.67^a$ | $1.67^a$ | $3.33^a$ |

$^{a, b}$Means within a row with different superscript are different at P < 0.05.

Results are presented in Table 18. Overall mortality was not different across treatments (Table 18). Feed conversion for the d0 Mist group was significantly lower than all other treatments on day 25 with a 5.3% improvement over the pCON and a 6.5% improvement over the nCON. After 39 days on feed, feed conversion of the *Megasphaera elsdenii* treated groups were not significantly different from the pCON but tended to be numerically lower at the exception of d7 GAV. Feed conversion for d21 GAV group was significantly lower than the nCON with a 7.7% improvement in feed conversion.

Example 12

Growing Different Strains of *M. elsdenii* on Semi-Defined Growth Media Supplemented with Two Carbons Sources A. Experimental Design The following bacterial strains were used in this Example: (1) *Megasphaera elsdenii* NCIMB 41125, (2) *Megasphaera elsdenii* ATCC 25940, (3) *Megasphaera elsdenii* NCIMB 702261, (4) *Megasphaera elsdenii* NCIMB 702262, and (5) *Megasphaera elsdenii* NCIMB 702410.

All strains were grown in serum bottles on semi-defined lactate growth media. Resulting cultures were then used to inoculate 96-well plates containing semi defined growth media supplemented with two carbon sources: Na-lactate and glucose consisting of 60% of lactate and 40% of glucose, 70% of lactate and 30% of glucose, or 40% of lactate and 60% of glucose.

96-well plates were then incubated at 39° C. under anaerobic conditions and optical density (600 nm) were automatically recorded at 15 minutes intervals.

B. Analysis of Growth Characteristics of *M. elsdenii* Strains on Various Two-Carbon Media The resulting growth curves on the different semi-defined media and with the different *M. elsdenii* strains were plotted, with incubation time on the x-axis and optical density reading on the y-axis, in order to compare growth characteristics (FIG. 23-25).

All strains of *M. elsdenii* tested in this experiment displayed similar growth characteristics when grown on semi-defined media consisting of 60% of lactate and 40% of glucose, 70% of lactate and 30% of glucose, or 40% of lactate and 60% of glucose.

Example 13

Growing Different Strains of *M. elsdenii* on Semi-Defined Growth Media Supplemented with Two Carbons Sources Followed by Freeze-Drying the Cells A. Experimental Design The following bacterial strains were used in this Example: (1) *Megasphaera elsdenii* NCIMB 41125, (2) *Megasphaera elsdenii* ATCC 25940, (3) *Megasphaera elsdenii* NCIMB 702261, (4) *Megasphaera elsdenii* NCIMB 702262, and (5) *Megasphaera elsdenii* NCIMB 702410.

All strains were grown in serum bottles on semi-defined lactate growth media. Resulting cultures were then used to inoculate 5-L fermentor vessels containing semi-defined growth media supplemented with two carbon sources: Na-lactate and glucose consisting of 60% of lactate and 40% of glucose or 70% of lactate and 30% of glucose.

A sample of the cultures were collected after 8, 10, 12, 14, and 16 hours of growth, cooled to room temperature and cells were aseptically and anaerobically harvested by removing 99% of the liquid. Retentates were mixed with a solution of cryoprotectant (sucrose) at a 1/5 ratio, under aseptic and anaerobic conditions, to obtained a final sucrose concentration of 5% w/v. The mixture was sampled to determine pre-freeze-drying *M. elsdenii* concentration (i.e., viability count).

Aliquots of the resulting mixture were transferred into 10 mL vials (4 mL/vial) and snap frozen in liquid nitrogen. Vials were transferred to the freeze-dryer to be lyophilized following a rapid cycle. Once freeze-drying was complete, survival of the bacteria was determined by resuspending the lyophilized product in the anaerobic chamber with anaerobic diluent, allowing it to rehydrate for 40 minutes at room temperature, and then plating onto semi-defined lactate agar (i.e., viability count).

Cell loss was computed by subtracting the concentration of *M. elsdenii* recovered post-freeze-drying from the initial (pre-freeze-drying) concentration of AI elsdenii.

B. Comparing Cell Loss Post-Freeze-Drying of Different *M. elsdenii* Strains Grown on Various Semi-Defined Media, Harvested and Freeze-Dried at Various Times During Growth.

All strains of *M. elsdenii* tested in this experiment resulted in viable cells post-freeze-drying. The acceptable cell loss limit was set at 1.6 log CFU/mL. Cell losses encountered during freeze drying of cells grown on semi defined media containing 70% of lactate and 30% of glucose (Table 19), regardless of the strain or harvest time were all below acceptable limit and ranged from 0.3 to 1.3 log.

TABLE 19

Cell loss (Log CFU/mL) observed post-freeze-drying on *M. elsdenii* strains grown on semi-defined media consisting of 70% of lactate and 30% of glucose, harvested and freeze-dried after 8, 10, 12, 14, or 16 hours of incubation.

| | Harvest time, hours | | | | |
|---|---|---|---|---|---|
| Strain | 8 | 10 | 12 | 14 | 16 |
| NCIMB 41125 | — | 0.41 | 0.46 | 0.60 | 0.42 |
| ATCC 25940 | 0.61 | 0.56 | 0.64 | 0.80 | 0.61 |
| NCIMB 702261 | 0.76 | 0.85 | 1.09 | 0.81 | 1.29 |
| NCIMB 702262 | 0.65 | 0.98 | 1.01 | 0.96 | 0.99 |
| NCIMB 702410 | 0.81 | 0.83 | 1.00 | 1.02 | 1.20 |

Cell losses encountered during freeze drying of cells grown on semi defined media containing 60% of lactate and 40% of glucose (Table 20), were more affected by harvest time, but all strains still resulted in cell loss that were below acceptable limit for at least three of the harvest times. Optimization of the harvest time pre-freeze drying can result in further improvement of the recovery post-freeze-drying.

TABLE 20

Cell loss (Log CFU/mL) observed post-freeze-drying on *M. elsdenii* strains grown on semi-defined media consisting of 60% of lactate and 40% of glucose, harvested and freeze-dried after 8, 10, 12, 14, or 16 hours of incubation.

| | Harvest time, hours | | | | |
|---|---|---|---|---|---|
| Strain | 8 | 10 | 12 | 14 | 16 |
| NCIMB 41125 | 0.34 | 0.28 | 0.34 | 0.37 | 0.33 |
| ATCC 25940 | 0.72 | 1.46 | 2.01 | 1.80 | 1.47 |
| NCIMB 02261 | 0.74 | 1.26 | 1.28 | 1.48 | 1.45 |
| NCIMB 02262 | 0.58 | 1.19 | 1.74 | 1.32 | 1.80 |
| NCIMB 02410 | — | 0.70 | 1.12 | 1.37 | 1.19 |

Overall the method described herein resulted in freeze dried product containing viable cells regardless of the *Megasphaera elsdenii* strain used.

Example 14

Encapsulating Freeze-Dried *M. elsdenii* and Determining Stability of Same

*M. elsdenii* NCIMB 41125 retentates obtained through TFF were aseptically mixed with cryoprotectant solution (sucrose) at a 1/5 ratio to obtain a final concentration of 5% sucrose (w/v). Mixture was snap frozen in liquid nitrogen and transferred to the freeze-dryer to be lyophilized using a rapid cycle. Once freeze-drying was complete, survival of the bacteria was determined by resuspending the lyophilized product in the anaerobic chamber with anaerobic diluent, allowing it to rehydrate for 40 minutes at room temperature, and then plating onto semi defined lactate agar.

Resulting freeze dried *M. elsdenii* powder was then mixed with a carrier (bulking agent) and encapsulated by dispensing the powder into heated palm oil distillate or stearic acid. The mixture was then rapidly cooled and resulting product sampled to determine survival of bacteria. Samples were resuspended in the anaerobic chamber with anaerobic diluent, blended for 15 seconds, and allowed to rehydrate for 40 minutes at room temperature before being plated onto semi defined lactate agar. This experiment was repeated three times using different heating temperature and different type of oil (method 1, 2, and 3). Method 1 uses a heating temperature of 110° C. and a palm oil distillate as the encapsulating material. Method 2 uses a heating temperature of 52° C. and a mixture of mono- and di-glycerides of palmitic, stearic, oleic, linoleic, and linolenic acids as the encapsulating material. Method 3 uses a heating temperature of 65° C. and a and a mixture of mono- and di-glycerides of palmitic, stearic, oleic, linoleic, and linolenic acids as the encapsulating material.

Percent loss was computed by subtracting the concentration of *M. elsdenii* recovered post-encapsulation from the concentration recovered post-freeze-drying and dividing it by the concentration recovered post-freeze-drying.

Additional samples were collected from product encapsulated, using method 2 and method 3, and stored at room temperature under aerobic conditions for a period of 4 months to assess stability of the product. Samples were resuspended in the anaerobic chamber with anaerobic diluent, mixed for 15 seconds, and allowed to rehydrate for 40 minutes at room temperature before being plated onto semi-defined lactate agar. FIGS. 26 and 27 show that stability of the encapsulated freeze-dried *M. elsdenii* using method 2 or 3 only lost approximately 1 log CFU/g.

TABLE 21

Percent loss observed post-encapsulation of freeze-dried *M. elsdenii* using method 1, 2, or 3.

| | Percent loss from encapsulation |
|---|---|
| Method 1 | 83.4% |
| Method 2 | 24.5% |
| Method 3 | 32.1% |

Method 2 and 3 used to encapsulate freeze-dried *M. elsdenii* resulted in a cell recovery greater than 67.9% (Table 21).

In addition, freeze dried samples encapsulated following method 2 or method 3 resulted in a 1 log reduction in cell viability during storage at room temperature under normal oxygen and humidity conditions for up to 4 months.

Encapsulation of freeze dried *M. elsdenii* following method 2 and 3 provided further protection to the bacteria from oxygen and moisture. This process would allow to store encapsulated freeze-dried *M. elsdenii* at room temperature without any specific packaging and would permit the addition of the product in feed.

Example 15

Shelf Life of Freeze-Dried *M. elsdenii* Produced on a Pilot Scale.

A. Experimental Design

A 600-liter batch of semi defined media consisting of 70% of lactate and 30% of glucose was used in this experiment to grow *M. elsdenii* NCIMB 41125. After 14 hours incubation at 39° C., resulting culture was cooled to room temperature and cells harvested using a tangential flow filtration system as described in Example 2. Ninety nine percent of the liquid volume was removed from the culture and retentate was then resuspended in a sucrose cryoprotectant solution at a 1:5 ratio to obtain a final sucrose concentration of 5% w/v.

The mixture was then frozen in liquid nitrogen, frozen pellets transferred to the freeze dryer and lyophilized following a rapid cycle. Once freeze drying was complete, lyophilized powder was collected and packaged (Table 22) under anaerobic conditions into Mylar pouch alone ("M.e.") or with maltodextrin as a bulking agent ("M.e.+Maltodextrin").

TABLE 22

| Mylar pouch filling | | | |
|---|---|---|---|
| | Freeze dried powder | Maltodextrin | Total weight in pouch |
| M.e. | 0.15 g | — | 0.15 g |
| M.e. + Maltodextrin | 0.15 g | 2.34 g | 2.50 g |

*M. elsdenii* concentration in the freeze-dried product (3 samples per treatment) was determined by resuspending the lyophilized product in the anaerobic chamber with anaerobic diluent, allowing it to rehydrate for 40 minutes at room temperature, and then plating onto semi defined lactate agar (i.e. viability count). *M. elsdenii* concentration was expressed as CFU/Pouch and log transformed.

B. Shelf Life Study

Mylar pouches containing the different treatments were stored either at room temperature (75° F.; 25° C.) or at 40° F. (4° C.). Additional samples were obtained after 0.5, 1, 2, 3, 4, and 6 months of storage and processed in the same way as previously described (3 samples per treatment per time point) to determine product shelf life. *M. elsdenii* concentration was expressed as CFU/Pouch and log transformed.

Shelf life data are presented in FIG. 28. *M. elsdenii* concentration over time was affected by storage temperature. After 6 months of storage, samples stored at 40° F. (4.4° C.) were stable regardless of the presence or absence of maltodextrin, whereas samples stored at 75° F. (23.9° C.) lost about 1.6 log for the "M.e." treatment and about 0.8 log for the "M.e.+Maltodextrin" treatment.

Example 16

Microbial Cell Growth, Medium, Temperature, and pH

Anaerobic bacteria can be divided into three categories, (1) obligate anaerobes; (2) aerotolerant anaerobes; and (3) facultative anaerobes. Obligate anaerobes are bacteria that do not survive in normal atmospheric concentrations of oxygen. Some obligate anaerobes can survive in up to 8% oxygen, while others cannot survive unless the oxygen concentration is less than 0.5%. Aerotolerant anaerobes can survive in the presence of oxygen, but do not utilize oxygen for growth. Facultative anaerobes are able to use oxygen for aerobic respiration, but can also use anaerobic respiration if no oxygen is present.

Similarly, aerobic bacteria can be divided into two categories: (1) obligate aerobes; and (2) microaerophiles. Obligate aerobes require oxygen to perform cellular respiration and can survive in normal atmospheric concentrations of oxygen. Microaerophiles require oxygen for cellular growth, but are harmed by normal atmospheric concentrations of oxygen.

Yeast are single-celled, eukaryotic microorganisms that are classified as a member of the fungus kingdom. Yeasts can be obligate aerobes or facultative anaerobes.

*Megasphaera*, such as *M. elsdenii* and *Bifidobacterium*, such as *B. breve* are representative species of obligate anaerobes. *Lactobacillus*, such as *L. plantarum* and *Bifidobacterium*, such as *B. animalis* subsp. *lactis* are representative species of aerotolerant anaerobes. *Pediococcus*, such as *P. acidilactici* and *Lactobacillus*, such as *L. casei* are representative species of facultative anaerobes. *Bacillus*, such as *B. subtilis* is a representative specie of an obligate aerobe. *Saccharomyces*, such as *S. boulardii* and *S. cerevisiae* are representative species of yeast.

Aerobic bacteria, anaerobic bacteria, and yeast are grown on a media comprising at least one carbon source selected from the group consisting of: casein, lactate, dextrose, fructose, fructan, glucose, sucrose, lactose, maltose, acetate, glycerol, mannitol, sorbitol, saccharose, xylose, molasses, fucose, glucosamine, dextran, a fat, an oil, sodium acetate, arabinose, soy protein, soluble protein, raffinose, amylose, starch, tryptone, yeast extract and combinations thereof. Also, aerobic bacteria, anaerobic bacteria, and yeast are grown on a media comprising at least two carbon sources selected from the group consisting of: casein, lactate, dextrose, fructose, fructan, glucose, sucrose, lactose, maltose, acetate, glycerol, mannitol, sorbitol, saccharose, xylose, molasses, fucose, glucosamine, dextran, a fat, an oil, sodium acetate, arabinose, soy protein, soluble protein, raffinose, amylose, starch, tryptone, yeast extract and combinations thereof. The anaerobic bacteria are grown under anaerobic conditions or with required oxygen conditions to facilitate anaerobic bacterial cell growth, and the aerobic bacteria and yeast are grown under appropriate oxygen conditions with a media comprising at least two carbon sources from above and at a temperature between 15° C. to 45° C. for *L. plantarum* and 20° C. to 45° C. for *B. breve, B. animalis* subsp. *lactis, P. acidilactici, L. casei, S. boulardii*, and *B. subtilis*. The optimum temperature for these strains is 37° C., except for *S. cerevisiae*, which prefers 30° C. The pH of the media is between 4.0 and 9, more specifically between pH 4.0 to 4.5, 4.5 to 5.5, 5.5 to 6.5, 6.5 to 7.5, 7.5 to 8.5, or 8.5 to 9.0. The microbes are grown until the exponential growth phase has ended, i.e., at least 1 hour to 6 hours, 6 hours to 12 hours, 12 hours to 24 hours, 24 hours to 36 hours, 36 hours to 48 hours, 48 hours to 72 hours, 72 hours to 96 hours, or 96 hours to 120 hours.

Once the media contain at least $1 \times 10^3$ CFU/g, the microbes are harvested under appropriate conditions and the microbes are freeze-dried and/or encapsulated for use in animal feed formulations.

Example 17

Use of Tangential Flow Filtration for Concentrating Cultures of Aerobic Bacteria, Anaerobic Bacteria, and Yeast Methods presented in Example 2 are used in this Example with the aerobic bacteria, anaerobic bacteria, and yeast disclosed in Example 16 and using the appropriate medium to allow for optimal microbial cell growth. Similar to *Megasphaera elsdenii*, using tangential flow filtration on aerobic bacteria (*Bacillus subtilis*), anaerobic bacteria (*Bifidobacterium breve, Lactobacillus plantarum, Bifidobacterium animalis* subsp. *lactis, Pediococcus acidilactici*, and *Lactobacillus casei*), and yeast (*Saccharomyces boulardii* and *cerevisiae*) yields similar results with regard to the amount of viable microbes recovered in the permeate and retentate over the course of the concentration process. Additionally, the filtration process does not have an effect on microbial survivability or on the ability of the microbe to grow after being filtered. Thus, microbes are grown in a liquid broth, filtered and are prepared for freezing, freeze-drying, and/or encapsulation.

Example 18

Freezing and Freeze-Drying Parameters for Aerobic Bacteria, Anaerobic Bacteria, and Yeast To determine the effect of various freezing and freeze-drying parameters on different types of aerobic bacteria, anaerobic bacteria, and yeast, an Example according to Example 17 is performed. Similar to Example 3, the acceptable cell loss limit is set at 1.6 log CFU/mL.

Retentates of *Bifidobacterium breve, Lactobacillus plantarum, Bifidobacterium animalis* subsp. *lactis, Pediococcus acidilactici, Lactobacillus casei, Bacillus subtilis, Saccharomyces boulardii,* and *Saccharomyces cerevisiae* are resuspended in cryoprotectant solutions containing no cryoprotectant, skim milk, trehalose, sucrose, or a combination thereof prior to lyophilization. Each mixture is then transferred to vials and slowly frozen at −80° C. or snap frozen in liquid nitrogen, before being placed in the freeze-dryer to be lyophilized using either a rapid or slow cycle.

Retentates not mixed with cryoprotectant all have cell loss greater than retentates mixed with cryoprotectant solutions and cell loss greater than threshold regardless of the freeze-drying cycle or the freezing method.

Additionally, all freeze-drying processes that are tested result in products that are able to retain sufficient viability to initiate growth of the culture after rehydration, even after prolonged storage of 4 to 12 months at room temperature or at least 4° C.

Example 19

Effects of Storage Conditions on Yield and Stability of Freeze-Dried Aerobic Bacteria, Anaerobic Bacteria, and Yeast Testing methods for cell survival and microbial growth characteristics presented in Example 4 are used in this Example with aerobic bacteria, anaerobic bacteria, and yeast disclosed in Example 16 and using the appropriate medium to allow for optimal microbial cell growth.

To determine the effect of freeze-drying protocols and storage conditions on the growth characteristics and shelf life of *Bifidobacterium breve, Lactobacillus plantarum, Bifidobacterium animalis* subsp. *lactis, Pediococcus acidilactici, Lactobacillus casei, Bacillus subtilis, Saccharomyces boulardii,* and *Saccharomyces cerevisiae,* freeze-dried cultures produced as in Example 18 are then tested for microbial growth characteristics and cell survival during storage at 4° C. or 25° C. in aerobic or anaerobic conditions for 0, 2, 4, 8, 12, 16, 20, and 24 weeks using growth curve analysis and spread plating technique.

The samples from freeze-dried anaerobic bacteria that are stored in aerobic conditions, regardless of the treatment, decay more rapidly with additional cell loss in comparison to their anaerobic-stored counterpart.

The samples that are stored at 25° C. decay faster than their counterpart stored at 4° C.

The samples that are frozen in liquid nitrogen and are stored at 25° C. post-freeze-drying do not lose more cells than their counterpart stored at 4° C. over the 16-week storage period; however, differences between samples are significant between the 25° C. and 4° C. storage after 20 and/or 24 weeks of storage.

On each sampling day, a growth curve experiment is performed to compare the growth characteristics of the freeze-dried product to the non-freeze-dried product. Non-freeze-dried samples that are used for each growth curve are "fresh" (no more than 2-days of age). Freeze-dried products stored at 4° C. have a shorter lag time than the freeze-dried products stored at 25° C. After 16 weeks of storage, all samples from anaerobic bacteria containing a cryoprotectant, frozen in liquid nitrogen, freeze-dried, and stored under anaerobic conditions that are revived and are viable again. Similarly, all samples from aerobic bacteria and yeast containing a cryoprotectant, frozen in liquid nitrogen, and freeze-dried that are revived are also viable again.

Example 20

Effects of Storage Conditions on Yield and Stability of Encapsulated Freeze-Dried Aerobic, Anaerobic Bacteria, and Yeast Freezing and freeze-drying retentates of various aerobic bacteria, anaerobic bacteria, and yeast are performed as described in Examples 16-19. After freeze-drying, the anaerobic bacteria are mixed with a carrier (bulking agent) and are encapsulated by dispensing the freeze-dried powder into heated oil as described in Example 14. The mixture is then rapidly cooled and the resulting product is sampled to determine survival of the microbes. Anaerobic microbial samples are resuspended in the anaerobic chamber with anaerobic diluent, are mixed for 15 seconds, and are allowed to rehydrate for 40 minutes at room temperature before being plated onto semi-defined lactate agar. Aerobic microbial samples are resuspended in the in normal atmospheric concentrations of oxygen with a diluent, are mixed for 15 seconds, and are allowed to rehydrate for 40 minutes at room temperature before being plated onto semi-defined lactate agar. This experiment is repeated three times using different heating temperatures and different types of oils (method 1, 2, and 3). Method 1 uses a heating temperature of 110° C. and a palm oil distillate as the encapsulating material. Method 2 uses a heating temperature of 52° C. and a mixture of mono- and di-glycerides of palmitic, stearic, oleic, linoleic, and linolenic acids as the encapsulating material. Method 3 uses a heating temperature of 65° C. and a and a mixture of mono- and di-glycerides of palmitic, stearic, oleic, linoleic, and linolenic acids as the encapsulating material.

The percent cell loss from encapsulation is less than 40% using method 2 or 3. After encapsulation of the various aerobic bacteria, anaerobic bacteria, and yeast, the encapsulated microbes that are stored at room temperature under normal atmospheric oxygen conditions have only a slight reduction in cell viability over the course of storage (e.g., 0.5 to 2-log decrease in cell viability).

What is claimed is:

1. A method for treating or preventing a condition or disorder associated with lactic acid production in the gastrointestinal tract of a non-ruminant animal, comprising administering to the non-ruminant animal about 0.4 g of freeze-dried *Megasphaera elsdenii* (*M. elsdenii*) NCIMB 41125 cells, wherein the 0.4 g of freeze-dried *M. elsdenii* NCIMB 41125 cells contain about $7.02 \times 10^8$ CFU/mL of *M. elsdenii* NCIMB 41125 cells.

2. The method of claim 1, wherein the condition or disorder is acidosis.

3. The method of claim 1, wherein the non-ruminant animal is selected from the group consisting of: swine, chicken, goose, duck, quail, turkey, pigeon, horse, pony, donkey, and mule.

4. The method of claim 1, wherein the *M. elsdenii* NCIMB 41125 cells are administered in a feed mixture or a liquid.

5. The method of claim 1, wherein the *M. elsdenii* NCIMB 41125 cells are administered prior to, concomitantly with, or after feeding the non-ruminant animal with a food.

6. The method of claim 1, comprising a single administration of the *M. elsdenii* NCIMB 41125 cells, a daily administration of the *M. elsdenii* NCIMB 41125 cells or more than one administration of the *M. elsdenii* NCIMB 41125 cells on a single day.

7. The method of claim 1, wherein the freeze dried *M. elsdenii* NCIMB 41125 cells are administered via a treat.

8. The method of claim 4, wherein the liquid is administered by oral gavage or by spraying the non-ruminant animal with the liquid.

* * * * *